US009542597B2

(12) United States Patent
Chung et al.

(10) Patent No.: US 9,542,597 B2
(45) Date of Patent: *Jan. 10, 2017

(54) EVENT REGISTRATION AND MANAGEMENT SYSTEM AND METHOD FOR A MASS GATHERING EVENT

(71) Applicant: Amerasia International Technology, Inc., Princeton Junction, NJ (US)

(72) Inventors: Kevin Kwong-Tai Chung, Princeton, NJ (US); Albert Han-Ping Chung, New York, NY (US)

(73) Assignee: Amerasia International Technology, Inc., Princeton Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/066,004

(22) Filed: Mar. 10, 2016

(65) Prior Publication Data
US 2016/0188969 A1 Jun. 30, 2016

Related U.S. Application Data

(62) Division of application No. 14/159,573, filed on Jan. 21, 2014, now Pat. No. 9,286,511.
(Continued)

(51) Int. Cl.
G06K 9/00 (2006.01)
G06Q 10/10 (2012.01)
G06Q 50/26 (2012.01)

(52) U.S. Cl.
CPC ............. *G06K 9/00362* (2013.01); *G06K 9/00* (2013.01); *G06Q 10/10* (2013.01); *G06Q 50/26* (2013.01)

(58) Field of Classification Search
CPC .... G06Q 10/10; G06Q 10/0838; G06Q 50/26; G06Q 10/00; G06Q 10/06; G06Q 10/109; G06Q 30/02; G06Q 50/265; G08B 29/185; G08B 25/016; H04L 63/0861; H04L 63/107; H04L 63/12; H04L 51/32; H04L 67/02; H04L 67/306; H04L 9/3263; A61B 5/0002; A61B 5/1112; A63B 2225/685; G02B 2027/0112; G06F 3/011; G06F 2221/2111; G06F 17/30023; G06F 19/3493; G06F 9/542; G01S 13/87; G01S 2013/9346; G01S 19/14; G01S 17/66; G08G 1/20; G08G 1/054; G01C 15/04; G06K 9/00362; G06K 2017/0045; G06K 17/0032; G06K 17/00; G06K 19/06046; G06K 9/00; H01Q 1/2208; H01Q 1/2225; H01Q 1/22; A63F 3/064; A63F 13/573; B64C 39/024; A01K 29/005; B41J 2/17556; G07F 7/12; H04N 13/0468; H04N 1/23; H04N 2201/3243; C08F 220/24; A61L 2202/24; A62D 3/30
(Continued)

(56) References Cited

U.S. PATENT DOCUMENTS 6,027,026 A 2/2000 Husain et al.
6,223,122 B1 * 4/2001 Hancock ................ G01C 21/20
701/400
(Continued)

OTHER PUBLICATIONS

International Searching Authority, "PCT International Search Report and Written Opinion", International Application No. PCT/US14/12256, Jun. 16, 2014, 9 pages.

*Primary Examiner* — Vu Le
*Assistant Examiner* — Aklilu Woldemariam
(74) *Attorney, Agent, or Firm* — Clement A. Berard, Esq.; Dann, Dorfman, Herrell & Skillman, PC

(57) ABSTRACT

A system and method employing geo-tagging and/or biometric identification is employed for registration and man-
(Continued)

agement of a mass gathering event. Electronic devices are configured for capturing data and geo-tagging the captured data using the geographic position of the electronic device. Data relating thereto and related data concerning persons and/or locations and/or other things are associated with a unique identifier and are stored in a relational database from when they may be retrieved and processed for generating a response or other follow up which can be communicated to an electronic device. Responses are communicated to the electronic device that captured the data relating to the particular group of registrants or to an electronic device using its geographic location.

42 Claims, 18 Drawing Sheets

Related U.S. Application Data

(60) Provisional application No. 61/962,608, filed on Nov. 12, 2013, provisional application No. 61/849,697, filed on Feb. 1, 2013, provisional application No. 61/849,145, filed on Jan. 22, 2013.

(58) Field of Classification Search
USPC .......... 340/51, 386, 572, 573, 575; 382/115, 382/187, 188, 306, 314
See application file for complete search history.

(56) References Cited

U.S. PATENT DOCUMENTS

| | | |
|---|---|---|
| 6,657,543 B1 | 12/2003 | Chung |
| 6,696,954 B2 | 2/2004 | Chung |
| 6,703,935 B1 | 3/2004 | Chung |
| 6,883,710 B2 | 4/2005 | Chung |
| 6,943,688 B2 | 9/2005 | Chung |
| 6,961,000 B2 | 11/2005 | Chung |
| 7,036,729 B2 | 5/2006 | Chung |
| 7,077,313 B2 | 7/2006 | Chung |
| 7,098,793 B2 | 8/2006 | Chung |
| 7,158,030 B2 | 1/2007 | Chung |
| 7,173,722 B1 * | 2/2007 | Lapstun ............... B41J 2/16511 270/52.01 |
| 7,221,269 B2 | 5/2007 | Onderko |
| 7,319,397 B2 | 1/2008 | Chung |
| 7,342,497 B2 | 3/2008 | Chung |
| 7,382,255 B2 | 6/2008 | Chung |
| 7,423,535 B2 | 9/2008 | Chung |
| 7,456,748 B2 | 11/2008 | Cheng |
| 7,501,954 B1 | 3/2009 | Chung |
| 7,508,308 B2 | 3/2009 | Chung |
| 7,513,425 B2 | 4/2009 | Chung |
| 7,609,168 B2 * | 10/2009 | Boverie ................ A61B 5/11 180/273 |
| 7,614,553 B2 | 11/2009 | Chung |
| 7,623,036 B2 | 11/2009 | Onderko |
| 7,635,087 B1 | 12/2009 | Chung |
| 7,635,088 B2 | 12/2009 | Chung |
| 7,813,934 B1 | 10/2010 | Chung |
| 7,828,215 B2 | 11/2010 | Chung |
| 7,828,654 B2 * | 11/2010 | Carter, Sr. .......... G07F 17/3223 463/16 |
| 7,839,289 B2 | 11/2010 | Chung |
| 7,975,920 B2 | 7/2011 | Chung |
| 7,988,047 B2 | 8/2011 | Chung |
| 8,066,184 B2 | 11/2011 | Chung |
| 8,174,383 B1 | 5/2012 | Chung |
| 8,261,985 B2 | 9/2012 | Chung |
| 8,261,986 B2 | 9/2012 | Chung |
| 8,301,108 B2 * | 10/2012 | Naboulsi ............... G08B 21/06 340/575 |
| 8,630,513 B2 * | 1/2014 | Gokturk ........... G06F 17/30253 340/5.81 |
| 9,286,511 B2 | 3/2016 | Chung et al. |
| 2004/0208343 A1 * | 10/2004 | Golden ............... A01K 11/008 382/110 |
| 2004/0233040 A1 * | 11/2004 | Lane .................... G06K 19/025 340/5.86 |
| 2005/0181765 A1 * | 8/2005 | Mark .................... G06Q 10/10 455/411 |
| 2007/0017985 A1 * | 1/2007 | Lapstun .............. G06F 3/03545 235/435 |
| 2007/0071206 A1 * | 3/2007 | Gainsboro .......... H04M 3/2281 379/168 |
| 2009/0324211 A1 | 12/2009 | Strandell et al. |
| 2010/0141385 A1 | 6/2010 | Shiau et al. |
| 2010/0145947 A1 | 6/2010 | Kolman et al. |
| 2010/0223663 A1 * | 9/2010 | Morimoto ............... G06F 21/32 726/7 |
| 2010/0333194 A1 | 12/2010 | Ricordi et al. |
| 2011/0130636 A1 | 6/2011 | Daniel et al. |
| 2011/0282631 A1 * | 11/2011 | Poling .................. G06Q 10/10 702/188 |
| 2012/0190386 A1 * | 7/2012 | Anderson ............. G01C 15/04 455/456.3 |
| 2012/0206485 A1 * | 8/2012 | Osterhout .......... G02B 27/0093 345/633 |
| 2012/0212406 A1 * | 8/2012 | Osterhout ............ G02B 27/017 345/156 |
| 2013/0251214 A1 * | 9/2013 | Chung .................. G06Q 10/00 382/116 |

* cited by examiner

EVENT REGISTRATION AND MANAGEMENT SYSTEM AND METHOD FOR A MASS GATHERING EVENT

This Application is a division of U.S. patent application Ser. No. 14/159,573 entitled "EVENT REGISTRATION AND MANAGEMENT SYSTEM AND METHOD EMPLOYING GEO-TAGGING AND BIOMETRICS" which was filed on Jan. 21, 2014, and which claims the benefit of U.S. Provisional Application Ser. No. 61/962,608, the title beginning "National Census and National Citizen Registration Applications Based on Event Management System . . . " filed Nov. 12, 2013, of U.S. Provisional Application Ser. No. 61/849,697, the title beginning "National Emergency and Disaster Management System . . . " filed Feb. 1, 2013, and of U.S. Provisional Application Ser. No. 61/849,145, the title beginning "Avante Vaccination Registration and Management System . . . " filed Jan. 22, 2013, each of which is hereby incorporated herein by reference in its entirety.

The present invention relates to a registration and management system and method and, in particular, to a registration and management system and method relating to a mass gathering event. The method and system may employ biometric identifiers and/or geographical identifiers.

Everyday events, whether they may be thought of as "normal" events or as "unusual" events or as "catastrophic" or "disaster" events, can typically involve volumes of data that relate to multiple people and/or multiple geographic locations and/or to multiple physical items. One example of such an event may include a vaccination program, e.g., against malaria, polio or another disease, wherein vaccines and supplies, personnel, persons vaccinated, and the locations thereof are desired to be registered, monitored, tracked and managed. Another example of such an event may include an emergency and/or disaster event, e.g., an earthquake or a hurricane or a tsunami or terrorist attack, wherein sites, buildings, facilities, damage conditions, supplies, personnel, persons located, persons evacuated, persons injured and/or killed, medical and security resources, and the locations thereof, are desired to be registered, monitored, tracked and managed. Yet another example of such an event may include a large crowd event, e.g., a pilgrimage or a convention or a gathering on the Washington, D.C. National Mall, or New Year's eve in Times Square, N.Y., or a US Presidential inauguration, wherein visitors, pilgrims, groups thereof, persons arriving and departing, sites, included events, supplies, personnel, medical and security resources, and the locations thereof, are desired to be registered, monitored, tracked and managed. An event may also include a census wherein data for a very large number of people may need to be gathered, checked, verified and followed up on, e.g., where the data is incomplete and/or inconsistent, or where another question arises, and the census area may not be one that is well mapped or politically organized and/or the people may not already be registered and identified, and/or may not have an address or even a permanent or fixed location or living site.

Acquiring all of the data associated with such events reliably and accurately, accumulating the acquired data in a form usable and useful for responding and/or managing personnel, and processing the accumulated data for conducting, monitoring and/or managing the event or the response to an event can present an extremely difficult or intractable data collection and/or data processing problem.

Some conventional systems provide RFID tags that can be attached to various items so that the RFID tags can be interrogated so as to be tracked and/or monitored. While helpful, RFID tags alone cannot track other than their physical location, and if a sensor is associated with the RFID tag, then the sensed parameter, e.g., temperature, humidity, location or other parameter sensed by the sensor. But typical RFID tag reading systems require discrete readers from which data may be difficult to acquire, particularly in uncontrolled environments and situations. In the case of a disaster or emergency, any in place RFID readers may be rendered wholly or partially inoperative.

Video surveillance systems may similarly be able to acquire image data in their field of view, but that data is limited by the generally fixed locations where the video cameras were placed, and often by the poor reliability thereof and/or poor or otherwise inadequate image quality. In the case of a disaster or emergency, any in place imagers and/or video cameras may be rendered wholly or partially inoperative.

The following US Patents and Patent Publications of the present inventor that relate to registration, election and voting systems and methods, and to tracking systems and methods, are identified as background information:

U.S. Pat. No. 7,561,724 entitled "Registration Method, as for Voting."

U.S. Pat. No. 7,635,088 entitled "Electronic Voting Method and System Employing a Printed Machine Readable Ballot."

U.S. Pat. No. 7,635,087 entitled "Method for Processing a Machine Readable Ballot and Ballot Therefor."

U.S. Pat. No. 7,614,553 entitled "Method for Reading an Optically Readable Sheet."

U.S. Pat. No. 7,461,787 entitled "Electronic Voting Apparatus, System and Method."

U.S. Pat. No. 7,436,989 entitled "Generation, Verification and Reproduction of a Digitized Writing."

U.S. Pat. No. 7,431,209 entitled "Electronic Voting Apparatus, System and Method."

U.S. Pat. No. 7,422,150 entitled "Electronic Voting Apparatus, System and Method."

U.S. Pat. No. 7,197,167 entitled "Registration Apparatus and Method, as for Voting."

U.S. Pat. No. 7,077,313 entitled "Electronic Voting Method for Optically Scanned Ballot."

U.S. Pat. No. 7,036,730 entitled "Electronic Voting Apparatus, System and Method."

U.S. Pat. No. 6,973,581 entitled "Packet-based Internet Voting Transactions with Biometric Authentication."

U.S. Pat. No. 6,892,944 entitled "Electronic Voting Apparatus and Method for Optically Scanned Ballot."

U.S. Pat. No. 8,214,913 entitled "Physically Secure Computing System and Device, and Physically Secure Container Therefor."

U.S. Pat. No. 8,066,184 entitled "Optically Readable Marking Sheet and Reading Apparatus and Method Therefor."

U.S. Pat. No. 7,988,047 entitled "Method for Decoding an Optically Readable Sheet."

U.S. Pat. No. 7,975,920 entitled "Electronic Voting Method and System Employing a Machine Readable Ballot Envelope."

U.S. Pat. No. 7,894,634 entitled "Generation and Authentication of Digitized Biometric Data for Conducting a Transaction."

U.S. Pat. No. 7,828,215 entitled "Reader for an Optically Readable Ballot."

US Patent Publication 2011/0089236 entitled "System and Method for Decoding an Optically Readable Markable Sheet and Markable Sheet therefor."

US Patent Publication 2010/0252628 entitled "Manual Recount Process Using Digitally Imaged Ballots."
US Patent Publication 2010/0170948 entitled "Method for Decoding an Optically Readable Sheet."
U.S. Pat. No. 7,513,425 entitled "Article Tracking System and Method."
U.S. Pat. No. 7,423,535 entitled "Object Monitoring, Locating, and Tracking Method Employing RFID Devices."
U.S. Pat. No. 7,342,497 entitled "Object Monitoring, Locating, and Tracking System Employing RFID Devices."
U.S. Pat. No. 7,319,397 entitled "RFID Device for Object Monitoring, Locating, and Tracking."
U.S. Pat. No. 7,098,793 entitled "Tracking System and Method Employing Plural Smart Tags."
U.S. Pat. No. 7,036,729 entitled "Article Tracking Method and System."
U.S. Pat. No. 6,961,000 entitled "Smart Tag Data Encoding Method."
U.S. Pat. No. 6,883,710 entitled "Article Tracking System and Method."
U.S. Pat. No. 7,197,167 entitled "Registration Apparatus and Method, as for Voting."
U.S. Pat. No. 7,561,724 entitled "Registration Method, as for Voting."
U.S. Pat. No. 7,894,634 entitled "Generation and Authentication of Digitized Biometric Data for Conducting a Transaction."

Applicant believes there may be a need for a registration and management system and method that employs electronic devices to acquire data and to relate that data to the location and date and time of its being acquired, as well as to generate one or more relational databases to store such data, make it available for review, monitoring and management, and to provide plans for action and follow up of such action.

Accordingly, a method for operating a registration and management system may comprise: configuring an electronic device having a device identifier and including an imager and a geographic position locator, the configuring including configuring the electronic device for geo-tagging the captured images using the determined geographic location, and for receiving a unique identifier; causing the geo-tagged captured images to be associated with the unique identifier; receiving registration data, associating the unique identifier with the received registration data; storing data including the unique identifier, the geo-tagged captured images, the received registration data, and the device identifier, in a relational data base that is separate from the electronic device, repeating the foregoing steps for a number of registrants; retrieving from the relational database stored data relating to a particular registrant using the unique identifier, or using a location of a geo-tagged captured image, or using the received registration data, or using the device identifier, or using a combination thereof; generating from the retrieved data a response relating to the particular registrant; and communicating the response to the electronic device that captured data relating to the particular registrant.

A registration and management system may comprise: an electronic device having a device identifier and including an imager for capturing images and a geographic position locator, the electronic device being configured for geo-tagging the captured images, and for receiving a unique identifier; a computer processor receiving captured images associated with the unique identifier, registration data relating to a registrant, and associating the unique identifier with the received registration data, a relational database storing data including the unique identifier, the captured images, the received registration data, and the device identifier, wherein the relational data base may be separate from the electronic device; wherein the foregoing is repeated for a number of registrants; the computer processor retrieving from the relational database stored data using the unique identifier, or using a captured image, or using the received registration data, or using the device identifier, or using a combination thereof; the computer processor generating from the retrieved data a response, and a communication link communicating the response to the electronic device.

A method for operating a registration and management system may comprise: configuring an electronic device having a device identifier and including an imager and a geographic position locator, including configuring the electronic device for capturing a biometric identifier, for geo-tagging the captured images, for geo-tagging the captured biometric identifier, and for receiving a unique identifier; causing the geo-tagged captured images and geo-tagged captured biometric identifier to be associated with the unique identifier; receiving registration data; associating the unique identifier with the received registration data; storing data including the unique identifier, the geo-tagged captured images, the geo-tagged captured biometric identifier, the received registration data, and the device identifier, in a relational data base that is separate from the electronic device; repeating the foregoing steps for a number of registrants; retrieving from the relational database stored data using the unique identifier, or using a location, or using the captured biometric identifier, or using the received registration data, or using the device identifier, or using a combination thereof; generating from the retrieved data a response and communicating the response to the electronic device.

A method for operating a registration and management system for a mass gathering event may comprise: configuring an electronic device having a device identifier and including a device for capturing data, including a communication device, and a combination thereof, and including a geographic position locator for determining geographic location, including configuring the electronic device for geo-tagging captured data and for receiving a unique identifier; receiving or providing a unique identifier associated with a group of registrants and a mass gathering event; causing the captured data to be associated with the unique identifier; receiving registration data relating to the group of registrants; associating the unique identifier with the received registration data relating to the group of registrants; storing data including the unique identifier, the captured data associated with the unique identifier, the received registration data relating to the group of registrants associated with the unique identifier, and the device identifier, in a relational data base; repeating the foregoing steps for a number of groups of registrants; retrieving from the relational database stored data relating to a particular group of registrants using the unique identifier, or using a location of geo-tagged captured data, or using the received registration data relating to the particular group of registrants, or using the device identifier, or using a combination thereof; generating from the retrieved data relating to the particular group of registrants a response relating to the particular group of registrants; and communicating the response relating to the particular group of registrants to the electronic device that captured data relating to the particular group of registrants or to an electronic device using the geographic location thereof, or to both.

A registration and management system for a mass gathering event may comprise: an electronic device having a device identifier and including a device for capturing data, including a communication device, and a combination thereof, and including a geographic position locator, the electronic device being configured for geo-tagging the captured data and for receiving a unique identifier; a computer processor receiving or providing a unique identifier relating to a group of registrants and a mass gathering event, captured data associated with the unique identifier, registration data relating to the group of registrants, and associating the unique identifier with the received registration data relating to the group of registrants; a relational database storing data including the unique identifier, the captured data, the received registration data, and the device identifier; wherein the foregoing is repeated for a number of groups of registrants; the computer processor retrieving from the relational database stored data relating to a particular group of registrants using the unique identifier, or using captured data, or using the received registration data, or using the device identifier, or using a combination thereof; the computer processor generating from the retrieved data a response relating to the particular group of registrants; and a communication link communicating the response to the electronic device that captured data using the device identifier of the electronic device or to an electronic device using the geographic location thereof, or to both.

In summarizing the arrangements described and/or claimed herein, a selection of concepts and/or elements and/or steps that are described in the detailed description herein may be made or simplified. Any summary is not intended to identify key features, elements and/or steps, or essential features, elements and/or steps, relating to the claimed subject matter, and so are not intended to be limiting and should not be construed to be limiting of or defining of the scope and breadth of the claimed subject matter.

BRIEF DESCRIPTION OF THE DRAWING

The detailed description of the preferred embodiment(s) will be more easily and better understood when read in conjunction with the FIGURES of the Drawing which include:

FIG. 10 is an illustration of an example of a data entry form suitable for use with the present arrangement and includes FIGS. 10A, 10B and 10C illustrating three sheets thereof;

Figure 1:
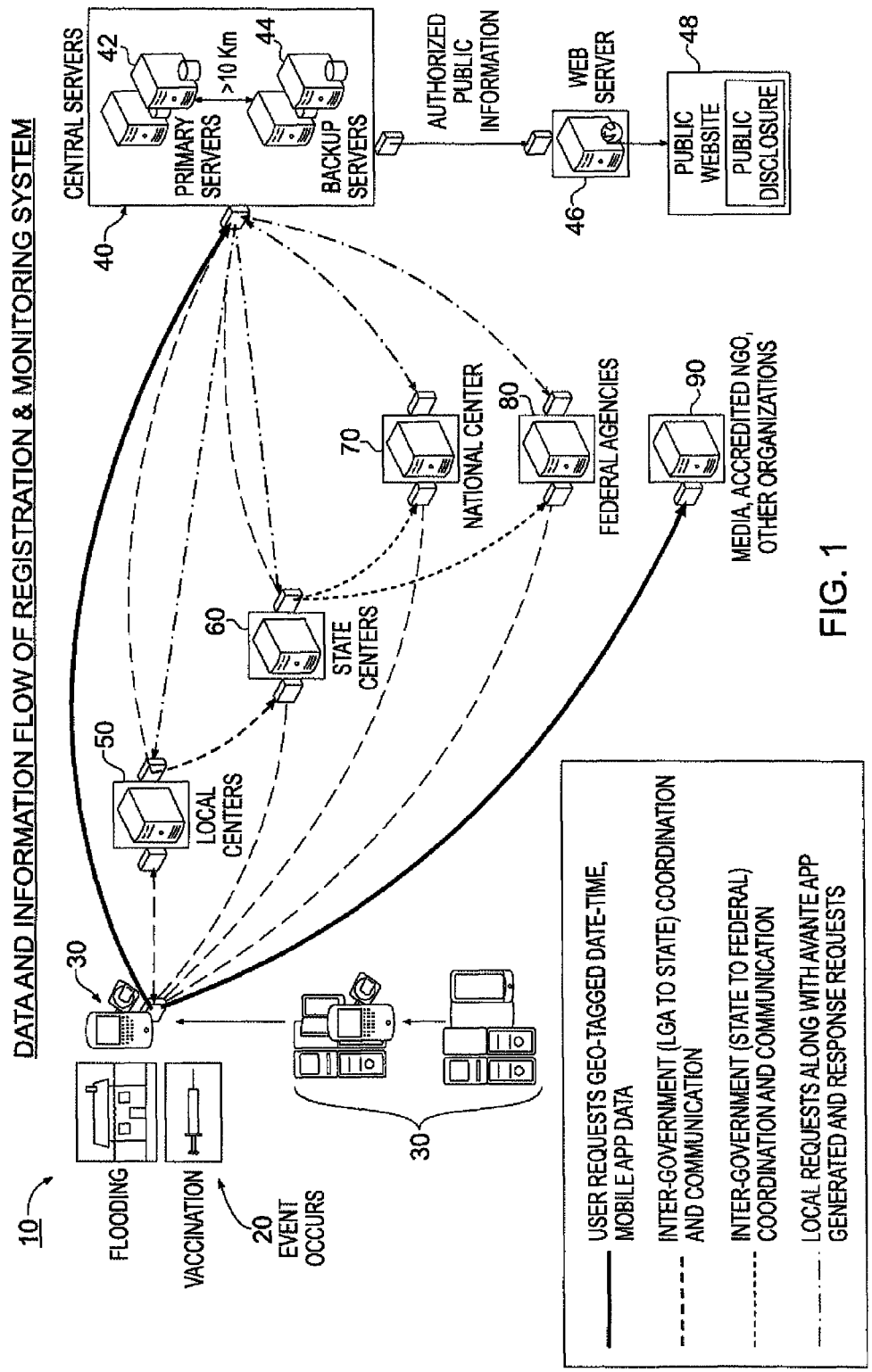
FIG. 1 is a schematic flow diagram illustrating the flow of information and data in an example embodiment of a registration and monitoring system and method according to the present arrangement.

In the Drawing, where an element or feature is shown in more than one drawing figure, the same alphanumeric designation may be used to designate such element or feature in each figure, and where a closely related or modified element is shown in a figure, the same alphanumerical designation primed or designated "a" or "b" or the like may be used to designate the modified element or feature. According to common practice, the various features of the drawing are not to scale, and the dimensions of the various features may be arbitrarily expanded or reduced, and any value stated in any Figure is given by way of example only.

DESCRIPTION OF THE PREFERRED
EMBODIMENT(S)

By way of introduction, events affecting large numbers of people and/or widespread geographic areas occur almost daily, and may extend across a substantial period of time and a substantial geographic area. One example is a vaccination program that may be for a nation, province, state, county and/or large city, wherein many teams and sites are employed to provide medical service to a large and dispersed population. Management of such an endeavor is a gigantic undertaking and requires the gathering of information and data (e.g., registration) regarding all aspects of the program, e.g., teams, supplies, equipment, personnel, persons vaccinated, records and status of vaccinations of such persons, conditions experienced by personnel, supplies and equipment, inventories of supplies and equipment, the locations of all of the foregoing, as well as any other data useful and/or helpful to the manager and/or sponsoring entity.

Such management is made more difficult as the geographic area of such program increases and as the number of participants, e.g., both personnel and persons served, increases, and the degree of difficulty is further increases as the infrastructure of the geographic area involved becomes less modern. For example, consider even in a modern place such as New York State or California, which have modern infrastructure and a largely registered population through driver licenses, tax rolls and voting registration records, how the diversity of concentrated populations in cities and dispersed populations in small towns and rural areas present different tracking and management issues and challenges. And then consider how much more difficult the challenge becomes where the infrastructure is less developed and the population less known, such as in Nigeria, Kenya or India, or where the infrastructure is damaged, such as after a storm or other natural disaster.

While a planned program such as a vaccination program is conducted largely under normal conditions, whatever those may be, consider the complications introduced where there is disruption and/or damage, such as following a flood, hurricane, tornado, earthquake, tsunami or other significant disruptive event. Population can be displaced and moving, infrastructure can be damaged, damaged structures may be being razed and debris removed, and normal geographic markers may be disturbed, all of which serve to complicate the registration and tracking or monitoring of conditions and responses thereto.

The present registration and management system is arranged, structured and configured to register people, sites, structures, objects and events in a way that tends to not be affected by their movement and/or being changed, and to make collected (e.g., captured) information and data (hereinafter, the term "data" is employed to refer to all forms and formats of information and data) readily available in connected and traceable and related ways that facilitate management of whatever is being monitored and/or managed. This end is enabled by the correlating of the data to other data that are generally not affected by changes in events and/or time, the other data including, e.g., biometric identifying data, geographic identifying data, and date and time data, and in particular one or more unique identifiers that are associated with particular participants, locations and/or events. Further, where changing conditions can affect the effectiveness of the program, e.g., the handling of vaccines and relief supplies, the razing and removal of damaged structures and debris, data representative of the conditions at defined locations and times is collected and is correlated to other related data, so that an accurate representation of various locations, conditions and situations can be registered and monitored, and managed, wherein the unique identifiers provide at least one linking basis for such correlation.

Figure 1A:
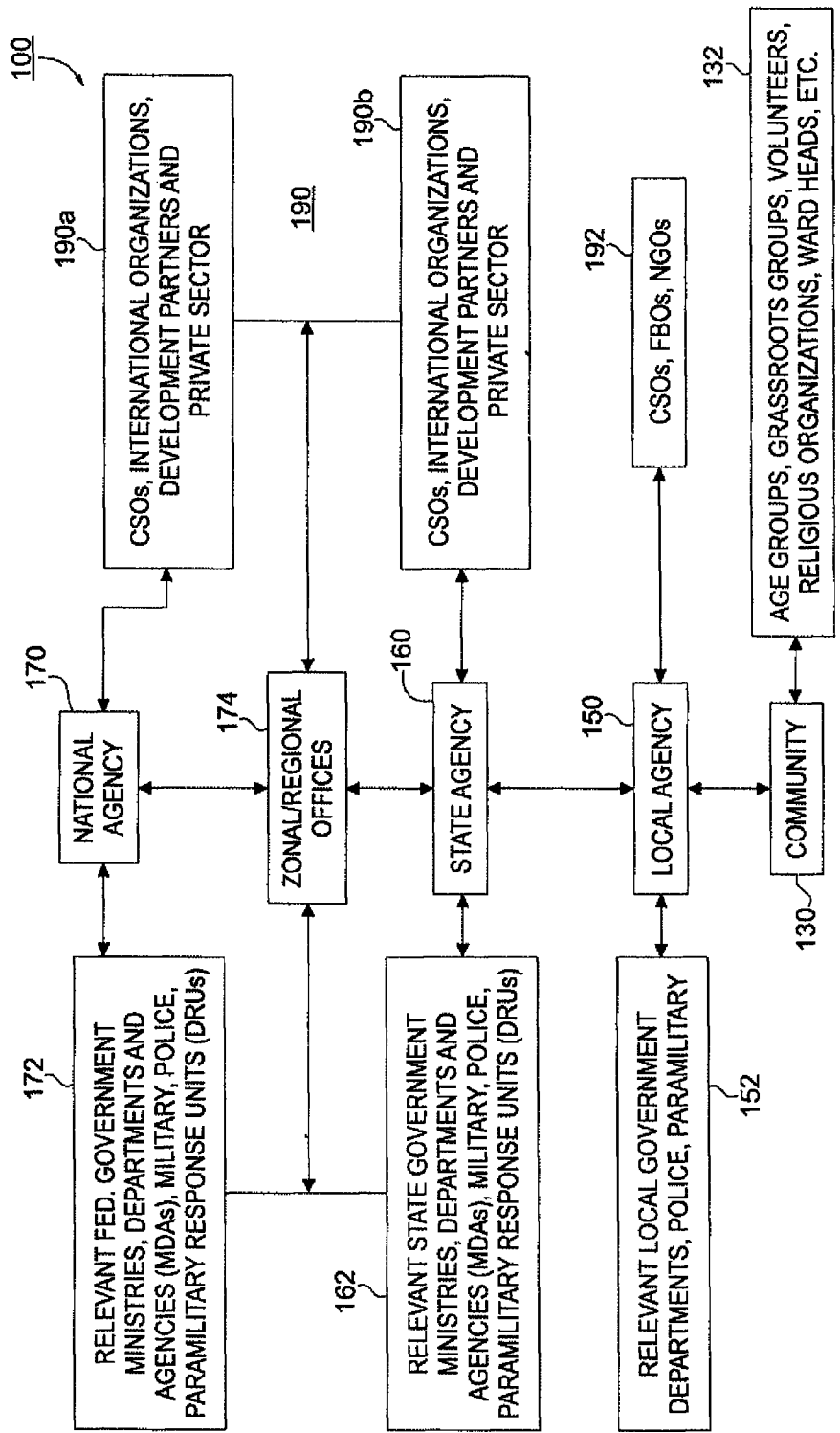
FIG. 1A is a schematic diagram of an example national organizational structure with which the registration and monitoring system of FIG. 1 may be utilized.

FIG. 1 is a schematic flow diagram 10 illustrating the flow of information and data in an example embodiment of a registration and monitoring system 10 and method 10 according to the present arrangement, and FIG. 1A is a schematic diagram of an example national organizational structure 100 with which the system and method 10 of FIG. 1 may be utilized. System and method 10 acquires event 20 data at various locations 30 and, after relating that data to both local and standard data markers, and particularly to respective unique identifiers, transmits the data to various agencies and locations 40, 50, 60, 70, 80, 90 whereat it may be evaluated and or otherwise processed to register, monitor and/or manage the event or events to which the data pertains. Certain processed data and/or certain selected data may be made available to other agencies 90 and/or to the public 48, e.g., via a web site or broadcast.

Data capture and/or collection is typically provided by plural portable digital electronic devices 30 that are deployed with personnel in the field. The events 20 that occur may include may planned and unplanned situations, such as a vaccination program or a flood, hurricane, tornado, earthquake, tsunami or other natural disaster. Data collected and captured by electronic devices 30, which may include biometric data, geographic data, location data, personal data, image data, entered data and other data, and a unique identifier, is communicated to central servers 40 as well as to one or more local centers 50, which may be owned, controlled and/or operated by or for one or more local governments or their agencies, to one or more regional or state centers 60, which may be owned, controlled and/or operated by or for one or more county, state or provincial governments or their agencies, to one or more national or federal centers 70, 80, which may be owned, controlled and/or operated by or for one or more national or federal governments or their agencies. Typical agencies may include health departments and emergency management agencies at any and/or all governmental and/or organizational levels, as well as by non-governmental organizations, publically owned entities and/or private entities. Various centers 50-80 may also be owned, controlled and/or operated by or for private or corporate organizations, non-governmental organizations (NGOs), and/or other entities.

Data communicated from one or more of centers 50, 60, 70 and 80 to one or more of electronic devices 30 may include applications software (sometimes referred to as an "app" or as "apps") as well as confirmations of data received, date-time stamps, hashing and other encrypting data, requests for data and/or reports and/or actions, coordination of tasks, and the like. Data communicated between and among centers 50, 60, 70, 80 typically includes coordination and communication in addition to requests, responses to requests, actual data relating to an event or events as previously described. All data and communication is preferably hashed and/or encrypted, digitally signed, and date-time stamped, e.g., for security and privacy, and preferably includes the unique identifiers associated therewith.

The correlation of geographic and/or location and/or other data with an actual location or place may be referred to as "geo-tagging" or a "geo-tag" and the correlating of data with a known accurate date and time may be referred to as "time stamping" or a "time stamp." Preferably each item of data is both geo-tagged and time-stamped at its source, and both the geo-tag and time-stamp are maintained with that data wherever it may be used and stored. Preferably, the unique identifier is likewise associated with and maintained with such data.

Electronic devices 30 may include, e.g., electronic devices 30 issued by entities that are involved in addressing the situations and/or events in view, and/or may include electronic devices 30 that belong to the people who are affected by the situations and/or events in view, victims of disasters, and the like and persons being vaccinated and the like. Because the arrangement of system 10 and method 10 is independent of any particular type or kind of electronic device 30, common devices such as smart phones, tablet computers, portable computers and the like, may all be utilized, thereby to provide both flexibility and an adaptability for system 10 and method 10 to operate in a wide variety of situations and circumstances without the need for specialized field equipment and/or centralized issuing and control thereof, although either may be utilized when and where desired.

Similarly, the unique identifier which serves as the linking identifier relating various data relating to a particular person and/or location and/or event may be centrally provided, e.g., such as by unique identifiers that are contained on data collection forms (e.g., on optically scannable and/or readable forms, such as registration forms and/or reporting forms) as described below, that may be acquired by electronic devices 30 capturing an image of such unique identifier, or may be generated in the operation of system and method 10 in the field, e.g., such as by generating a unique identifier from data relating to the location, situation, event and/or persons involved. In the latter instance, geo-tagging data, date-time stamp data and/or individual personal data may be combined and or otherwise employed to generate unique identifiers. The generation of unique identifiers may be a function provided by, e.g., application software that is downloaded to electronic devices 30.

Central servers 40, preferably including both primary servers 42 and one or more backup servers 44, are employed to receive the data communicated from electronic devices 30 and from centers 50, 60, 70 and 80, and under control of governing authorities, authorized public information may be released via one or more web servers 46 to one or more public web sites where it is disclosed and available to the public, e.g., via the Internet, communication networks, wireless devices, and the like.

An example national organizational structure 100 may include, e.g., both vertical and horizontal organizational and communication connections. For example, structure 100 may include a national agency 170 that may include e.g., relevant federal government ministries, departments and/or agencies, (MDAs) 172, military, police, and/or paramilitary response units (DRUs) 172, a state agency 160 that may include, e.g., relevant state government ministries, departments and/or agencies, (MDAs) 162, military, police, paramilitary response units and/or other disaster and relief entities (DRUs) 162, and/or relevant local agencies 150 that may include, e.g., relevant federal government ministries, departments and/or agencies, (MDAs) 152, military, police, paramilitary response units and/or other disaster and relief entities (DRUs) 152. National agency 170 may include various zonal, provincial and/or regional offices 174, and various state or provincial and/or regional agencies 160 may likewise include zonal, provincial and/or regional offices.

National agencies 170 and/or state agencies 160 may be in communication with and interface with various other organizations including, e.g., community service organizations (CSOs), international organizations, non-governmental organizations (NGOs), development partners and private sector entities 190, 190a, 190b. Local agencies 150 may be in communication with and interface with CSOs, community based organizations (CBOs), faith-based organizations (FBOs) and/or NGOs 192. Local agencies 150 also may be in communication with and interface with their community or communities 130 which may include, e.g., various age groups, grassroots groups, volunteers, volunteer organizations, religious organizations, ward heads, other local leaders, and the like 132.

Figure 2:
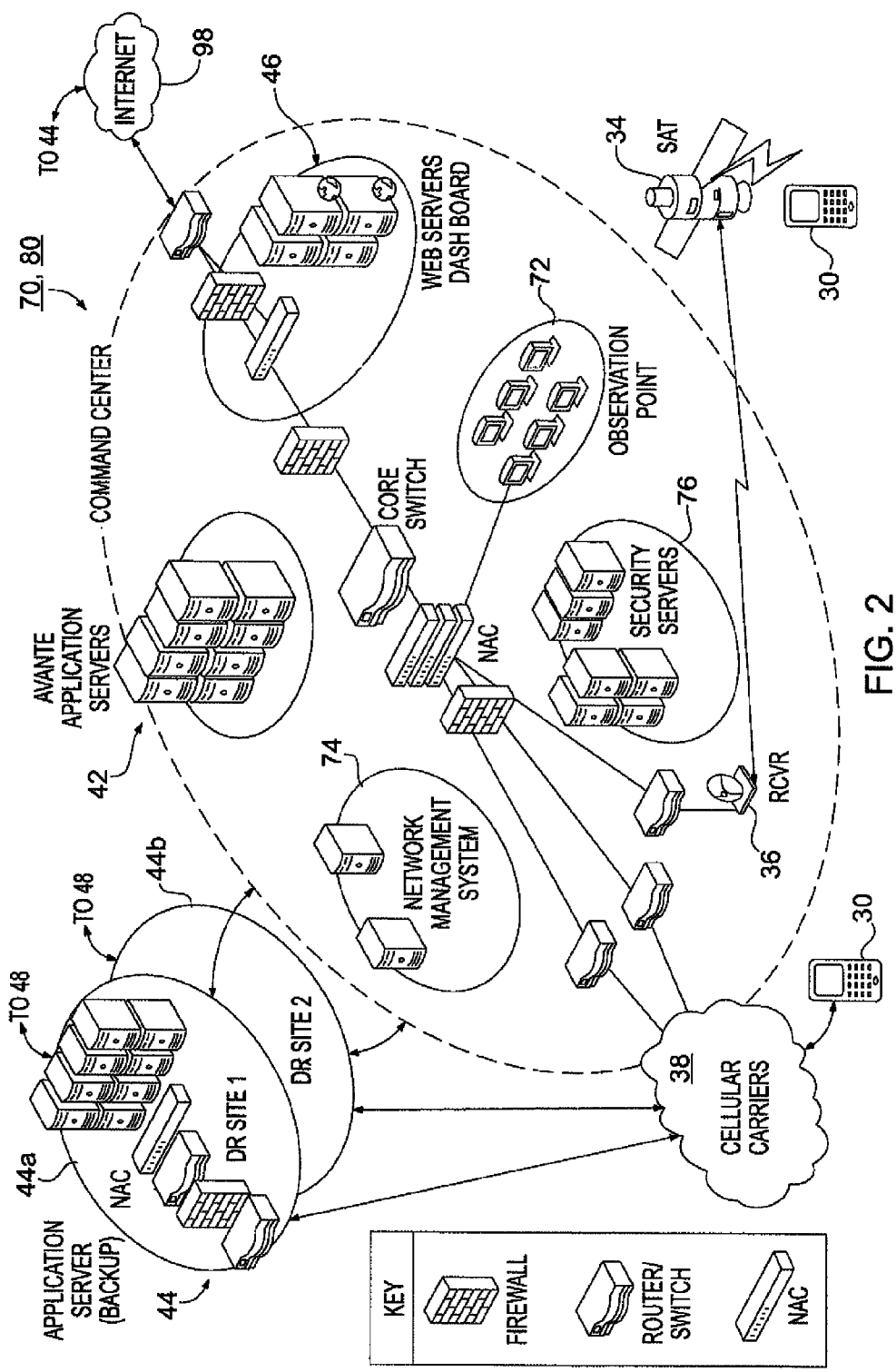
FIG. 2 is a schematic diagram illustrating an example embodiment of a registration and monitoring system data center according to the present arrangement.

FIG. 2 is a schematic diagram illustrating an example embodiment of a registration and monitoring system data center 70, 80 according to the present arrangement. The command center 70, 80 includes, e.g., application servers 42, backup servers 44, 44a, 44b which preferably are located at one or more separate sites, web servers 46, observation point 72, network management servers 74, security servers 76 and satellite receiver/transmitter 36, along with various routers, switches, fire walls and network access controls (NACs).

Command center 70, 80, typically at or near the highest levels of the system 10 structure, provides communication with and via the Internet 98 and cellular carriers 38 via a core switch, respective NACs, routers, switches and fire walls as illustrated, as well as with electronic devices 30 via a satellite receiver and transmitter 36 and satellite 34. The NAC feeds one or more observation points 72 where any and all of the data may be displayed, monitored, reviewed and utilized for ordering an action or actions be taken. Web servers 46 implement the interface with the Internet 98 and security servers 76 implement the hashing, encryption/decryption and other security functions. The command center 70, 80 and its internal elements and external communication links are managed by the network management system 74.

Command centers 70, 80, preferably include applications software that maintain overall control of the situations and/or events being registered, monitored and managed. Such operating software operates in conjunction with the web-based relational database, e.g., via application servers and back up servers 40, 42, 44, to monitor follow up and completion of the process being undertaken for each individual and/or location involved. Communication within command center 70, 80 is typically via an intranet, ethernet, WAN, LAN, optical fiber, or other suitable network, and communications between command center 70, 80 and back up application servers 40 may be via direct and/or network connections, via the Internet 98, via optical communication, via wireless communication, e.g., a microwave or other radio link, via a satellite link, or via any other suitable communication link, or via any combination of the foregoing.

The applications software may be of predetermined type and kind, e.g., one directed to managing a planned program, such as a vaccination program, or an unplanned situation or event, such as a natural or man-made disaster. Preferably the application software includes one or more operational modules that provide functionality and one or more situation modules that provide data relating to particular types and kinds of situations and/or events. Such situation modules may be configured as relational data bases that are preprogrammed for particular situations and events (e.g., as templates, look-up tables, and/or shells) and/or are programmable for particular situations and/or events, or are a combination thereof.

The functional modules utilize the data in the situation modules, e.g., databases, to monitor data entered into the relational database in relation to particular persons, locations, situations and/or events, to generate a schedule of follow up actions and/or follow up events that should be undertaken in response to the particular persons, locations, situations and/or events reported, and then to provide notifications of such follow up actions and/or follow up events to the personnel involved in responding to such particular persons, locations, situations and/or events, or to the particular persons involved, so that required and/or desired follow up can and does occur. The functional modules also monitor the updating of information in the relational database to verify that prescribed follow up has occurred (or at least been reported as having occurred), and to then provide notifications and monitoring of any additional and/or supplemental and/or alternative follow up that may be required and/or desired, and to likewise monitor same for completion.

In this manner, system and method 10 provide for and facilitate the acquisition of data necessary to address and monitor any particular program, situation and/or event, as well as actively and automatically providing specific direction to those who are to provide follow up actions and or services, while monitoring the performance and completion thereof. Throughout the foregoing operations, complete data as to conditions in the filed, actions taken and to be taken, follow up and status thereof is provided to those charged with monitoring and managing the particular situations and/or events, Advantageously, the web-based database automatically generates and communicates action-driven requests, alerts and instructions to operating and field personnel, and to victims, participants and clients, via any and/or all available communications paths, e.g., SMS, MMS, E-mail, facsimile (fax) and/or computer-generated telephone calls, e.g., directly to electronic devices 30, e.g., to the electronic devices 30 of the involved operating and field personnel, and to victims, participants and clients. The foregoing may be referred to as a push or push-based notification, and may require a certain response and within a predetermined time. Each communication may include a required response and time for action, thereby to aid in assisting and reporting of relevant status data. In addition, any or all such communications may also be directed to any one or more of the involved centers 50, 60, 70, 80, for their monitoring, and/or follow up, and/or management activities.

Figure 3:
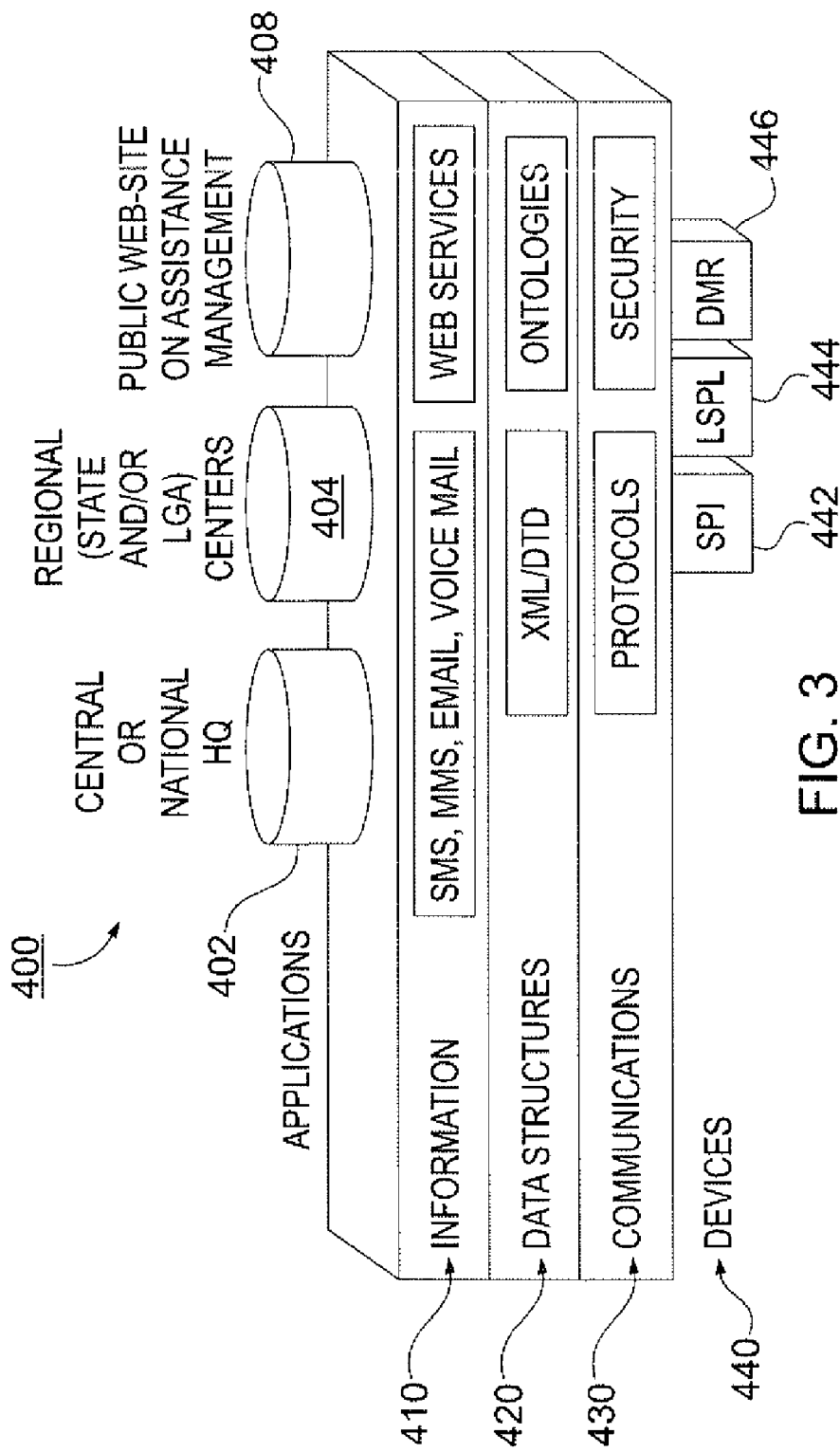
FIG. 3 is a schematic diagram of a communication and data structure associated with the example registration and monitoring system and method according to the present arrangement.

FIG. 3 is a schematic diagram of a communication and data structure 400 associated with the example registration and monitoring system and method 10 according to the present arrangement. Communication and data structure 400 includes an information layer 410, a data structure layer 420, a communications layer 430 and a devices layer 440, for providing two way secure communication among and between various authorized locations 402, 404, 408 and various equipment utilized in the system 10 and method 100 as described.

Information layer 410 is the layer that directly interfaces with and provides communication among and between various authorized locations and/or facilities and/or centers 402-408, some of which may be at the same location or nearby locations and some of which may be at one or more remote locations. Information layer 410 may provide information via various means including but not limited to Short Message Service (SMS), multi-media message service (MMS), e-mail, voice, voice mail and/or via web based (e.g., Internet and/or other network) services).

The facilities may include a headquarters 402, e.g., a central or national headquarters 402 where registration and management is conducted at a central or national level or a regional, e.g., provincial, headquarters 402 where registration and management is conducted at a state or provincial level. The facilities may also include one or more regional centers, e.g., a state or local government (LGA) or provincial center 404 where registration and management is conducted at a national level or a county or district center 404 where registration and management is conducted at a state or provincial level. The facilities may also include one or more local centers (LGA) 404, e.g., a county, district or municipal center 404 where registration and management is conducted at a state or provincial level.

Data structures layer 420 organizes data into standardized structures, e.g., eXtensible Markup language (XML) files with or without Document Type Definition (DTD) files, and provides for ontologies that track the nature of data that exists or may have existed at a particular place and time, e.g., as in events logging and data compilation as the system 10 is operated and the method is performed, whereby transparency, verification and auditability may be provided.

Communications layer 430 provides communication paths and links for communicating structured data between various devices 440 and the various locations 402-406. Communications layer 430 defines and applies the communication protocols by which data is transmitted and received data is interpreted, and further provides security for the data communicated. Preferably data is hashed and encrypted when stored and when communicated, both for security in transmission and against alteration and/or corruption, whether accidental or intentional.

Device layer 440 includes various devices by which data and information may be communicated between communication and data structure 400 and various equipment employed in the operation and use of system 10. An example thereof may include an Internet Protocol (IP) based bar code scanner 442 (either 1D or 2D), preferably including an embedded Global Positioning System (GPS) or other geographic locating device, which may be employed for scanning bar coded data of worker cards and/or badges, of personal identification cards and/or identification documents, of registration and/or emergency or support equipment and parts thereof, containers and other packaging therefor, and the like. Another example thereof may include an Internet Protocol (IP) based RFID reader and/or encoder 444 which may be employed for reading RFID devices of personal or worker cards and/or badges, of registration or identification cards and/or identification documents, of registration and/or emergency or support equipment and parts thereof, of containers and other packaging therefor, and the like, and/or for encoding data to such RFID devices. One preferred type of RFID reader operates in the UHF frequency band. Another example thereof may include an Internet Protocol (IP) based active RFID monitoring reader that operates with active RFID tags and devices, e.g., personal or worker cards and/or badges, registration cards and/or identification documents, registration and/or emergency or support equipment, containers and other packaging therefor, and parts thereof, and the like, and/or for encoding data to such active RFID devices. Other devices 440 may provide WiFi, Bluetooth and/or other wireless and/or radio connections.

Figure 4:
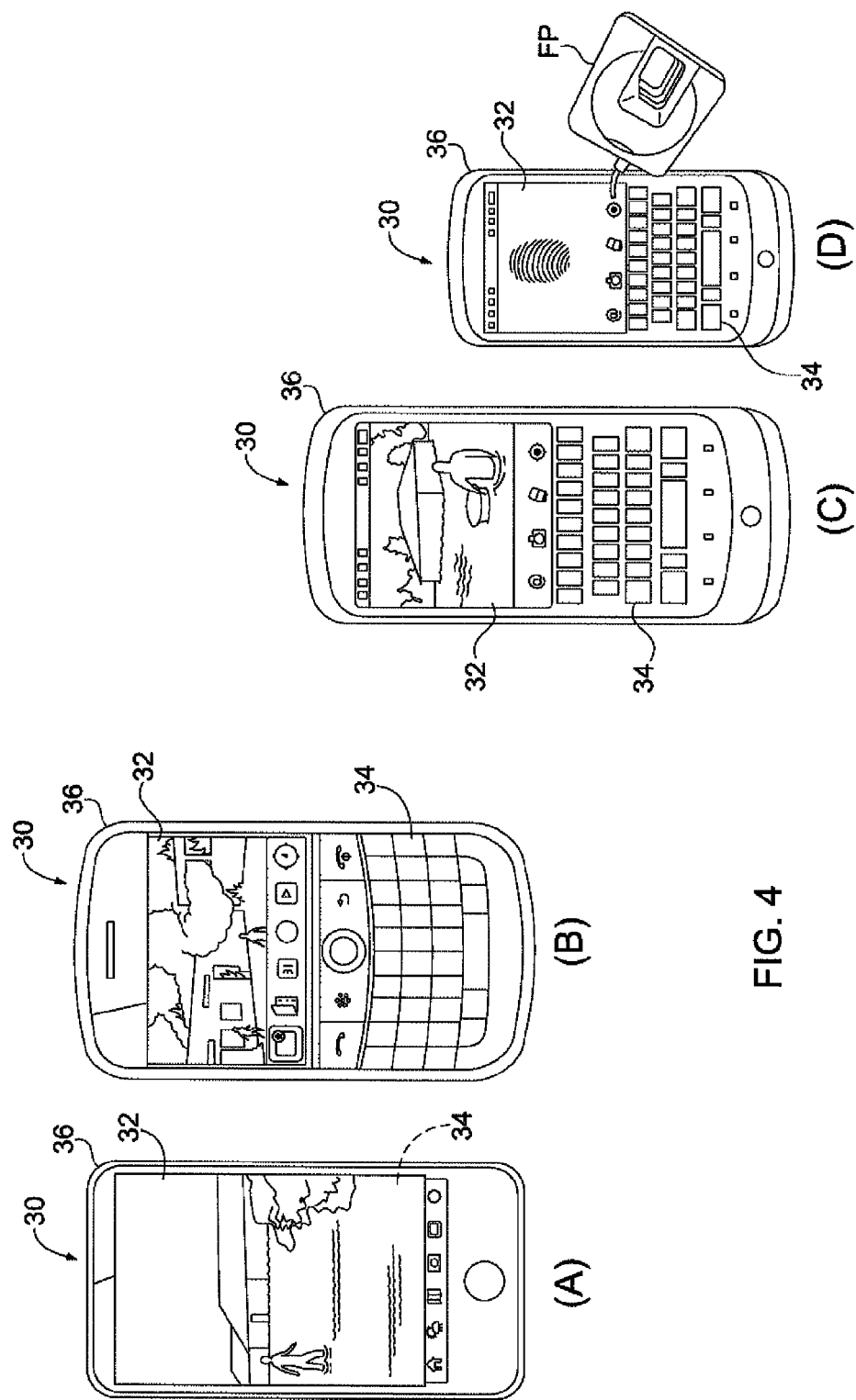
FIG. 4 is a schematic diagram illustrating various example embodiments (A), (B), (C) and (D) of digital electronic devices suitable for use with the registration and monitoring system and method of the present arrangement.

FIG. 4 is a schematic diagram illustrating various embodiments (A), (B), (C) and (D) of digital electronic devices 30 suitable for use with the registration and monitoring system and method 10 of the present arrangement. Each digital electronic device 30 is portable and includes a source of electrical power for its operation over a suitable period of time, and preferably is rechargeable for extending its operating time. Each portable electronic device 30 also includes a display 32, a data entry device 34, and an imager 36 which typically is located on the opposite surface of device 30 and so is not visible in FIG. 4. Display 32 and data entry device 34 may be physically separate as in embodiments (B) and (D) or may be integrated as a "virtual" keyboard 34 which is displayed on the touch screen display 32, 34, or a device 30 may include both a separate physical data entry device 34 as well as one integrated with a touch screen 32, 34. Imager 36 may provide for capturing one or more still images, a sequence of still images and/or video images that can be transmitted by device 30 to a remote location, either contemporaneously or at a later time.

Electronic device 30 includes communication capability, such as by WiFi, Bluetooth, cellular telephony and/or satellite telephony, including for voice communication, image transmission, text messaging, and data transmission and reception. Electronic device 30 also includes a device locating capability that can determine the physical location of device 30, such as, e.g., a global positioning system (GPS) device, a triangulation device, an interactive locator provided by a cellular or other communication system, or another position determining device or feature, whether a physical device or software implemented. Electronic device 30 also includes at least one capability for capturing biometric identifying data, such as a facial image captured by imager 36, a fingerprint captured by touch screen 32, 34, a digitized signature captured by touch screen 32, 34, or biometric identifying data captured by a separate device, e.g., by a fingerprint scanner FP. Device 30 further includes a source of accurate, reliable and trusted date and time data, e.g., by communication with an external source such as a cellular telephone system, a server, or a satellite system such as a communication satellite or a GPS satellite, or a precision internal clock or an internal clock that is synchronized at least periodically and/or regularly to such accurate, reliable and trusted external source of date and time data.

The example electronic device 30 illustrated in (A) resembles a touch screen smart phone such as, e.g., an iPhone® smart phone or an iPad® tablet computer available from Apple, or a Galaxy® smart phone or tablet computer available from Samsung or another smart phone or tablet computer. The example device 30 illustrated in (B) may be a smart phone such as, e.g., a Blackberry® phone, which has a physical keyboard. The example electronic device 30 illustrated in (C) may be an ANDROID® phone which has a physical keyboard 34. The example electronic device 30 illustrated in (D) may be a smart phone which has a physical keyboard and a connected fingerprint scanning device FP.

In the context of a disaster and/or emergency registration and management system 10, electronic device 30 may preferably be employed as a camera to capture images relating to an event associated therewith, e.g., to a flood event as illustrated on display 32 of devices (A) and (C), or to a fire event as illustrated on display 32 of device (B), or to confirm the capturing of a fingerprint by scanner FP as illustrated on display 32 of device (D). The captured image is associated with a particular event, e.g., a flood, fire, vaccination, and the like, and is also associated with the location of the electronic device 30 that captured the image when the image was captured, biometric identifying data captured by device 30, e.g., a fingerprint or facial image of a victim or claimant or patient, and related data entered via data entry device 34, e.g., personal identifying data such as name, address, cell phone number, driver's license, and the like, the location of the damage or fire, date and time, identity and/or authority of the data collector or official, and the like.

While the portable electronic devices 30 may employ smart phones or tablet computers as described, custom and/or dedicated devices may be provided that have the needed capabilities of data gathering, image capture, geographic location determination, biometric data capture, and communication. For example, the working parts of a relatively basic cellular or satellite telephone could be interconnected with a camera, GPS receiver, and fingerprint scanner, to provide the desired capabilities.

Figure 5:
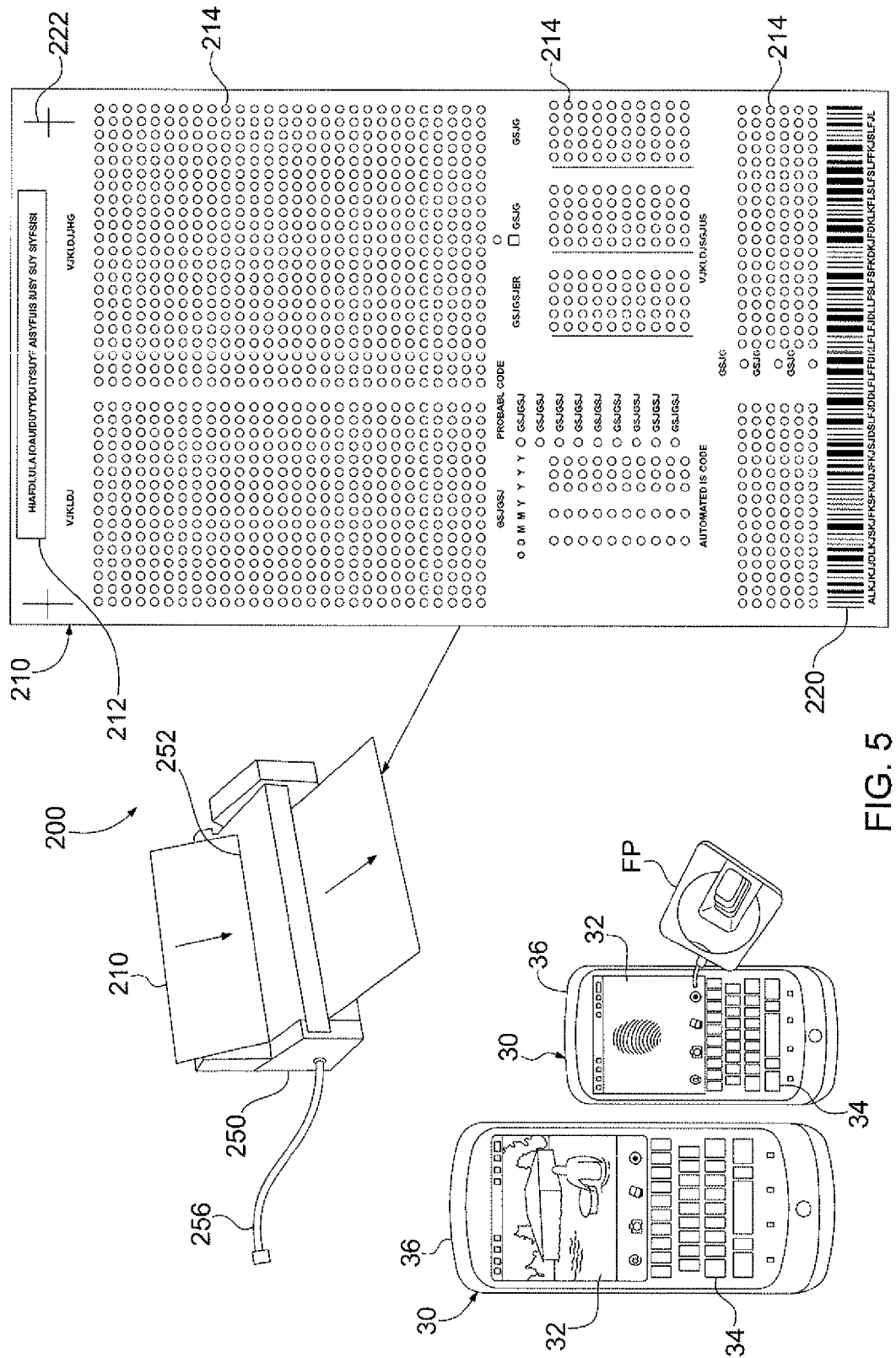
FIG. 5 is a schematic diagram illustrating examples of digital electronic devices and a data acquisition form and a scanner for use with the registration and monitoring system and method of the present arrangement.

FIG. 5 is a schematic diagram illustrating examples of digital electronic devices 30 and a data acquisition form 200, 210 and a scanner 200, 250 for use with the registration and monitoring system 10 and method 10 of the present arrangement. Electronic devices 30, e.g., as described above in relation to FIG. 4, are the primary data acquisition elements associated with system 10 that are employed for acquiring data relating to the event and/or occurrence being registered and to be monitored or managed, in conjunction with certain detailed related information that may be acquired by device 30 or via a paper form 210 filled in by a person seeking service or otherwise using system 10.

Each device 30 includes a keyboard or other data entry device for entering data as well as a camera 36 or other imager 36 for capturing images of a site, structure, person or other item or thing being registered, including biometric identifying data, such as a facial image captured by imager 36, a fingerprint captured by touch screen 32, 34, a digitized signature captured by touch screen 32, 34, or biometric identifying data captured by a separate device, e.g., by a fingerprint scanner FP. While detailed data, e.g., a unique identifier, personal data relating to a registrant or site or structure, can be entered via keyboard or data entry device 36, that would require use of a device 30 for a significant time, thereby limiting the number of persons, sites, structures and the like that could be registered in any given period of time. Preferably, device 30 is utilized more efficiently to acquire the data that it can most effectively acquire, such as image data and related geographic location data, and personal and other detailed data may be acquired by a parallel method.

To that end, and preferably, a parallel data acquisition element 200 is provided for acquiring such data. Data acquisition element 200 typically includes a form 210, e.g., a paper form, and a scanner 250 for scanning the form 210 for acquiring the data indicated thereon. Form 210 typically includes a title section 212 wherein the purpose of form 210 may be indicated and a plurality of data entry regions 214 having spaces wherein data may be entered, e.g., mark sense spaces as illustrated. Form 210 may include a one or more fiducial marks 222 in an asymmetrical pattern from which the orientation of form 210 may be determined, e.g., as when form 210 is scanned.

Form 210 may include, and preferably does include a region 220 wherein a unique identifier is provided, e.g., in a bar code and/or digitally readable font or representation, that can be decoded from a scanned image of the form 210. Bar codes 220 may be one dimensional (1-D) or two dimensional (2-D) bar codes, depending, e.g., upon the amount of data to be encoded in the bar code. While the unique identifier may be provided from a central source, e.g., a central center 50, 60, 70 or 80, and entered into device 30 via keyboard 34 and onto form 210, e.g., by marking mark sense spaces 214 thereon, it is preferred that the unique identifier be provided via form 210 and from there be associated with the data acquired by device 30.

While the unique identifier may be entered manually via data entry device 34 of electronic device 30, it is preferred that the unique identifier 220 be acquired by device 30 imaging the bar code or other representation 220 including the unique identifier using its imager 36, and then decoding the unique identifier from the image of representation 220, which is expected to be both faster and more accurate. Forms 210 may then be later correlated with related data that is acquired by electronic devices 30.

Forms 210 may be completed by a person registering, by a person associated with the agency conducting the registration or by both, or by others, as may be suitable and convenient in any given situation. It is preferred that at least the unique identifier 220 from form 210 be electronically acquired by the electronic device 30 that is acquiring data relating to that registrant, e.g., by imaging the identifier 220 using the imager 36 thereof, or by an ancillary device associated with the device 30, so that the data acquired by electronic device 30 can be associated with the data from form 210 by the unique identifier 220.

While unique identifier 220 of form 210 may typically include a bar code in many instances, other forms and devices may be employed, e.g., an RFID device may be affixed to form 210 that may be read by a near field reader of electronic device 30 or an encoded magnetic stripe may be disposed on form 210 that may be read by a magnetic stripe reader associated with electronic device 30, and/or any other suitable form of identifier.

Scanner 250 has an input 252 wherein a form 220 may be fed for being passed through an internal sensing arrangement for imaging and decoding the data printed and marked on form 210, including the unique identifier 220. The digital representation of form 210 and of the data thereon may be stored by scanner 250, may be decoded and stored by scanner 250 and/or may be stored and/or decoded and stored by scanner 250. The scanned data and/or the stored data may be communicated to an external facility, e.g., via a cable 256, either in real time (e.g., as scanned) or later in time.

Scanner 250 may be taken into the field and the forms 210 competed in the field may be scanned in the field, or, as probably is more likely and efficient, the forms 210 may be accumulated and transported to a central location, e.g., a center 50 or 60, and thereat scanned and decoded, thereby relieving personnel in the field from the scanning and data communication functions, and allowing them to work with registering more people during a given period of time. The forms 210 that are scanned and decoded at a central location, e.g., at a center 50 or 60, and the data therefrom are linked or related to data that was acquired via electronic devices 30 by the unique identifier that is associated with the forms 210 and with the data acquired by electronic devices 30.

The foregoing described real-time, geo-tagging system 10 for reporting and assessing situations relating to various types and kinds of programs, situations and/or events, provides the elements that facilitate a complete and timely response to whatever the program, situation and/or event may be. Data acquisition is simple, fast and accurate, utilizing commonly available electronic devices 30 and an "app" downloaded to such device 30, and centers upon one or more common actions, e.g., capturing an image, geo-locating and the like utilizing such devices 30, and on doing so at one or more times to capture not only specific data at a particular time, but also a chronological history of conditions, situations and/or events and one or more locations. Sources of data are verifiable and authenticatable using the unique identifiers, biometric identifiers, e.g., fingerprint, facial images, facial recognition, and the like, geographic locating, thereby to not only promote the accurate delivery of resources and services, but also to reduce false, inaccurate and/or fraudulent reports and/or claims.

For example, exact physical locations are acquired using latitude and longitude determined by GPS or other geo-locating of a specific location, event and/or person (participant and/or victim), real time and time lapse still and video images document and record actual conditions, identifications and the like. Communication is provided to victims and/or participants directly or to their representatives and/or contact person both to communicate data to the system database and to communicate status information and instructions in return, including real-time alerts of needs and/or situations or conditions that threaten health, life and/or property. Records are produced in real time and linked to particular persons and/or locations by a unique identifier, an optional biometric identifier, and/or a geo-tagged location, thereby minimizing incorrect identification and increasing the likelihood of detecting duplicate and/or fraudulent claims. Both lack of response and duplication of reporting and/or response may be monitored and at least minimized if not essentially eliminated, e.g., by verifying data basing actions on the unique identifier, optional biometric identifier, and/or geo-tagged location. Updating of data and provision of resources and actions is automatically coordinated in real time, thereby to speed response and improve the delivery of resources and services while reducing waste. The fully automated generation and delivery of "push" notifications to all appropriate responsible personnel and/or entities, e.g., via SMS, MMS, e-mail and/or telephone, can improve response quality and shorten response time. End to end detailed tracking of all reported data and responses, including of documentation do results, also can improve performance and efficiency, and can reduce waste. And appropriate and relatively wide role-based access to database data, status and responses, with appropriate privacy and security controls, helps to mobilize resources quickly and efficiently and to allow widest appropriate participation by involved persons, entities and the public in supporting and participating in the assistance and relief efforts.

Another positive feature is the use of uniquely identified optically scannable forms to acquire data in the field that can be later entered into the system 10 and its relational database and linked to data from other sources by the unique identifier, whether it be predetermined, e.g., printed on the forms, or generated in the field, e.g., by the smart phone 30 application. These forms preferably require minimal participation by official personnel, e.g., they can be largely or completely completed by victims and/or other participants, or by other non-official personnel, and thereby free official personnel and their equipment, e.g., electronic devices 30, to be utilized for the functions that must be performed by such devices.

Figure 6:
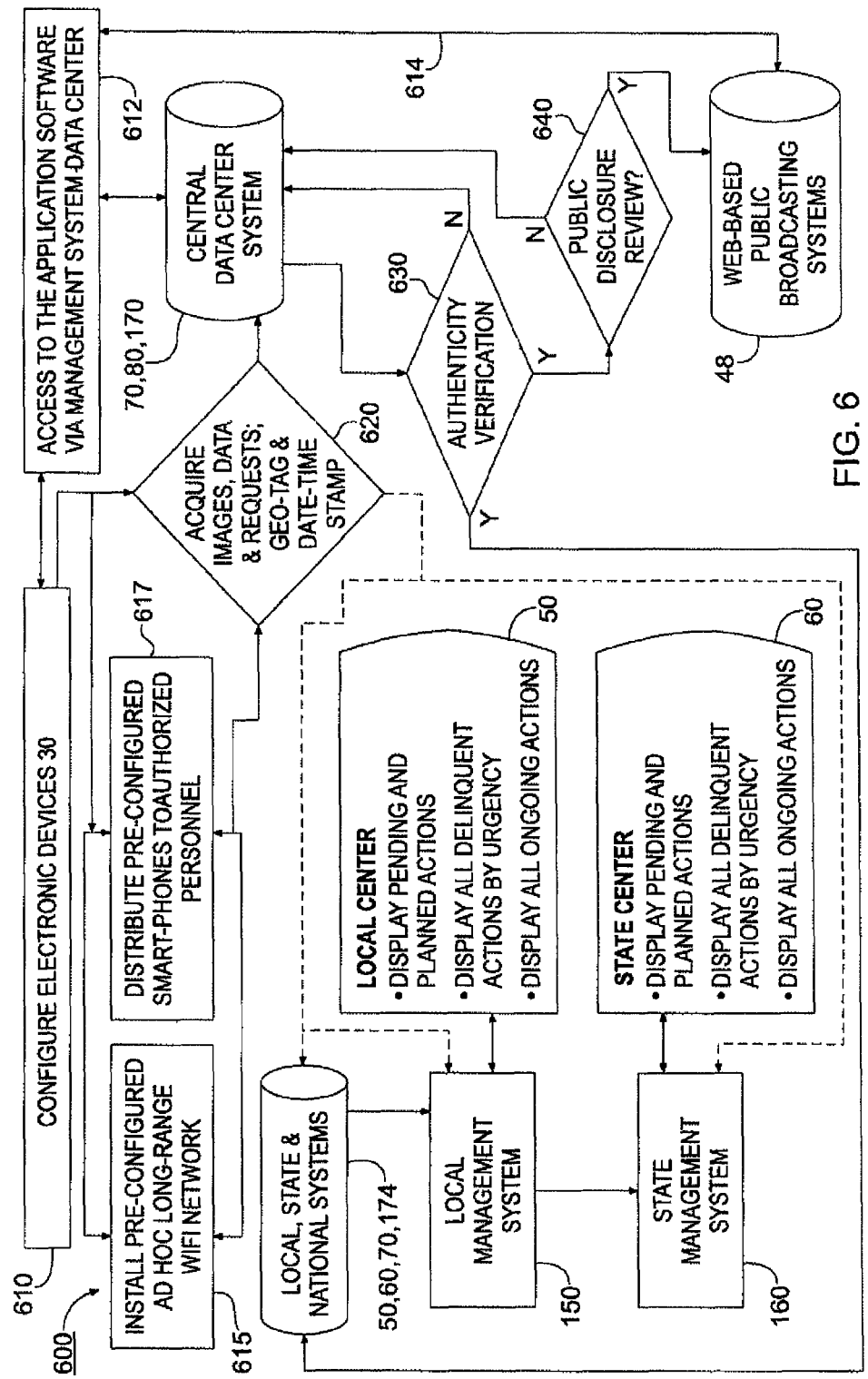
FIG. 6 is a schematic diagram illustrating the operational functionality of the registration and monitoring system and method of the present arrangement.

FIG. 6 is a schematic diagram illustrating the operational functionality 600 of the registration and monitoring system and method 10 of the present arrangement. By way of example and/or for convenience, the functionality or method 600 may be described herein, in the context of an emergency and/or disaster registration and management context, although the same functionality and method 600 is suitable for and may readily be employed in other contexts as well.

Electronic devices 30 may be configured 610 for use in registration and monitoring system and method 10 when needed or in advance of need whichever may be convenient. Configuration 610 may include, e.g., the downloading and/or installation 612 of application software in conventional smart phones, tablet computers and/or other personal electronic devices 30, or dedicated electronic devices 30 intended for use in system 10. Such devices 30 may be electronic devices 30 that are issued by an authorized agency, e.g., a federal, state and/or local authority or agency, and/or personal devices 30 that will be authorized for use in gathering and acquiring data. Ancillary and/or auxiliary devices, e.g., fingerprint scanners FP and/or cameras or other imagers may be provided and/or configured in like or similar manner.

Downloading and/or installation 612 of application software is typically via a central source, e.g., a central system data center 50, 60, 70, 80, and typically from a higher level data center such as central and/or federal system data center 80. Access 612 to such software is preferably limited to those personnel who are and/or devices that are authorized to receive the application software, e.g., based on their roles relative to seeking and/or acquiring data, or other relationship and/or association with an involved agency or entity.

In order to provide 615 sufficient communication infrastructure, e.g., where the existing communication infrastructure is inadequate and/or has been damaged and/or is not functioning as may occur in a large-scale disaster or emergency, pre-configured ad hoc network WiFi devices may be distributed for quickly establishing a suitable communication infra-structure that links to a communication hub or terminal, thereby to establish suitable communication with places both inside and outside the area affected by whatever event has occurred. Alternatively and/or additionally, configured electronic devices 30, e.g., smart phones 30, may be distributed 617 by local, state, federal, national and/or other entities to authorized personnel, e.g., employees, volunteers, community representatives, and the like in areas affected by the event and/or in nearby areas and other areas, and/or to others as may be necessary and convenient.

Users of electronic devices 30 acquire 620 images, data, position data, demographic data and other data, and the data acquired is geo-tagged 620, e.g., is associated with geographic data such as local images, GPS and/or other location data, and is date-time stamped 620, e.g., associated with a known accurate date and time such as that acquired via communication with a data center, web server and/or a communication service. The geo-tagged date-time stamped data is communicated 620 to one or more data centers 50, 60, 70, 80, although a higher level data center such as a federal or national data center 80 may be preferable. In the preferred arrangement 600 illustrated, data acquired 620 by electronic devices 30 is preferably communicated to a central or federal data system center 70, 80 whereat it may be categorized 170 by location and/or governmental entity and from which it may be distributed 170 to the appropriate lower level data center 50, 60. In the illustrated example, data communicated 620 to the central data center 80, 170, 172 or a federal data center 70, 170, 172 is communicated therefrom to regional or state data centers and agencies 60, 70, 174 and thereby to local and state centers and agencies 50, 150, 60, 160, although direct communication between the federal and/or central data center 70, 80 and lower level data centers and agencies 50, 150, 60, 160.

The receiving data center, e.g., central or federal center 70, 80 verifies 630 and/or authenticates 630, and preferably verifies 630 and authenticates 630, the received data before the data is communicated 630-Y to other entities and centers. Among the criteria for authentication and/or verification 630 may be verifying the international mobile equipment number (IMEI) or other unique identifier of the electronic device 30 that acquired the data, the Internet protocol (IP) address of the electronic device 30 that acquired the data, correlating the GPS location and the communication system determined location of the electronic device 30 that acquired the data, authenticating hashing and/or encryption indicators, and other criteria.

Data that has been verified and/or authenticated 630-Y may then be distributed to regional, state, local centers and/or entities, and to other entities, 60, 70, 150, 160, 174, 48, that have a need for the data and/or may use the data, in accordance with rules of operation (e.g., "business rules") established and implemented by the applicable data center. Distribution of data, and access to data, is therefore controlled according to the role of the personnel and/or entity receiving and/or seeking such data. Data that is not authenticated 630-N and/or not verified 630-N is notified back to the central and/or national data center 70, 80 which in accordance with the established rules for data distribution, may either not distribute the data until it is verified and/or authenticated 630, or may distribute the data with a notification that it has not been verified and/or authenticated 630, as the case may be.

Data that has been verified and/or authenticated 630-Y may then be released for distribution 640 to the public, e.g., via the Internet, web sites, news agencies, community organizations, and the like. Public disclosure review 640 applies rules, e.g., regarding the privacy of individuals and entities, security, public safety, policy factors, and the like to determine whether the data is releasable 640-Y to publically accessible means 48 or is not releasable 640-N in which case its not-releasable status is communicated 630-N to central data center 70, 80. Thus, it is likely that some, but not all of the verified and/or authenticated data will be publicly available.

Among the data that may be made available on public broadcasting systems 48, whether via the Internet, web sites, radio wave broadcast, or other means, may be a relational data base of current and past data including some or all of images, geo-position data, chronological data, categorized data, action requests, responses thereto, volunteer listings and/or activities, organization activities, and the like. The data available preferably includes data relating to the current event, program and/or situation, e.g., natural disaster, vaccination program and/or emergency, as well as similar data from previous situations of the same and/or different kinds. All of the foregoing data may be searched, accessed and retrieved, e.g., by category, chronology, date and time, location, geo-position, and the like, with successive and revisable search criteria so that a searcher may "drill down" to access the specific data desired.

Among the data that may be made available on public broadcasting systems 48 may be a data from the relational data base of current data including "push" notifications which are notifications relating to follow-up actions that are automatically forwarded, i.e. are "pushed," to the appropriate personnel, e.g., to their electronic devices 30, for follow up action and/or consideration. For example, push notifications relating to a mass vaccination program can include schedules for secondary vaccinations and/or booster shots, and push notifications relating to a natural disaster can include verifying that relief applications have been filed, processed and/or otherwise acted upon.

Preferably, all authenticated and/or verified data 630-Y is pushed out (e.g., transmitted) to appropriate local, state and regional entities and/or systems 50, 60, 70, 150, 160, 174, for monitoring and action, e.g., to local, state and national government agencies, local, state and national emergency management entities, local, state and national emergency management systems, military and other disaster response units (DRUs), and the like, where the data preferably is automatically entered into their respective relational databases. From such relational databases such agencies and entities may search, access and retrieve the data relating to their respective areas of responsibility for responding to and managing whatever situation may be encountered, and each relational database preferably includes similar data searching, accessing and retrieving capability as that described above. Each data base is preferably web-based and access controlled by need and/or role or position.

Relational databases of higher level entities preferably include all data relating to all entities and/or areas within their jurisdiction and/or responsibility, e.g., a state database includes at least all data relating to every jurisdiction and entity in that state, although data for geographically nearby and/or adjacent areas may be included, e.g., where conditions in one area may affect those in nearby locations, e.g., where flooding and flooding potential extends across political and/or entity jurisdictional boundaries. The searching of databases preferably enables operators to drill down to the lowest level of data, e.g., to access and retrieve data relating to an individual and/or specific geographic location and/or structure.

Information contained, e.g., stored, in such relational databases is available for display, either according to predetermined criteria or manual selection, and preferably includes both geo-tagging data and date-time stamp data, as well as all actions taken and assistance provided. Also preferably, a complete listing of all actions and their respective status is displayable and may easily be separated according to status, e.g., open items (being and/or to be acted upon), items being acted upon, items completed, items partially completed and needing follow up, delinquent items, and the like, and each is preferably easily selected, e.g., by clicking on an icon, according to status and responsible agency, entity, and/or personnel.

In addition, data relating to necessary or desired follow up response and/or action is preferably automatically pushed out (e.g., transmitted) to personnel and or agencies and/or entities that are responsible for implementation and/or management of such follow up activities. Such pushed data is preferably automatically communicated to the electronic devices 30 of the responsible personnel for their action and reporting of status and completion.

Among the advantages of the foregoing arrangement are that different agencies and entities, both governmental and non-governmental, can easily and efficiently locate and act on and coordinate actions on relevant data. The types and kinds of data with which such system and method may be employed is not limited by the system and/or method, and may include, e.g., medical issues such as triage processes, austere and other medical care, casualty staging and clearing, victim identification, mortuary services, patient reception and processing, assessment of health and/or medical needs. Further, data accumulated and available via the described system and method may also be employed for reviewing and evaluating the operation, efficiency and effectiveness of existing management organizations processes and for considering needs and potential improvements thereof.

Among the uses of the described system and method are, e.g., environmentally triggered events such as climate conditions, droughts, floods, storms, hurricanes, typhoons, cyclones, tornados, landslides, forest fires, storm surges, and the like, geologic conditions such as volcanic eruptions, earthquakes, tsunamis and the like, man-made conditions such as socio-economic, technologic, industrial, and terrorist threats and events, transport spills and accidents, poisonings, sabotage, and the like, and biologically triggered events such as epidemics, pandemics, disease, infestations of people, livestock, agriculture, wildlife, invasive species, and the like, and for assisting planning and training relating to any of the foregoing.

Figure 7:
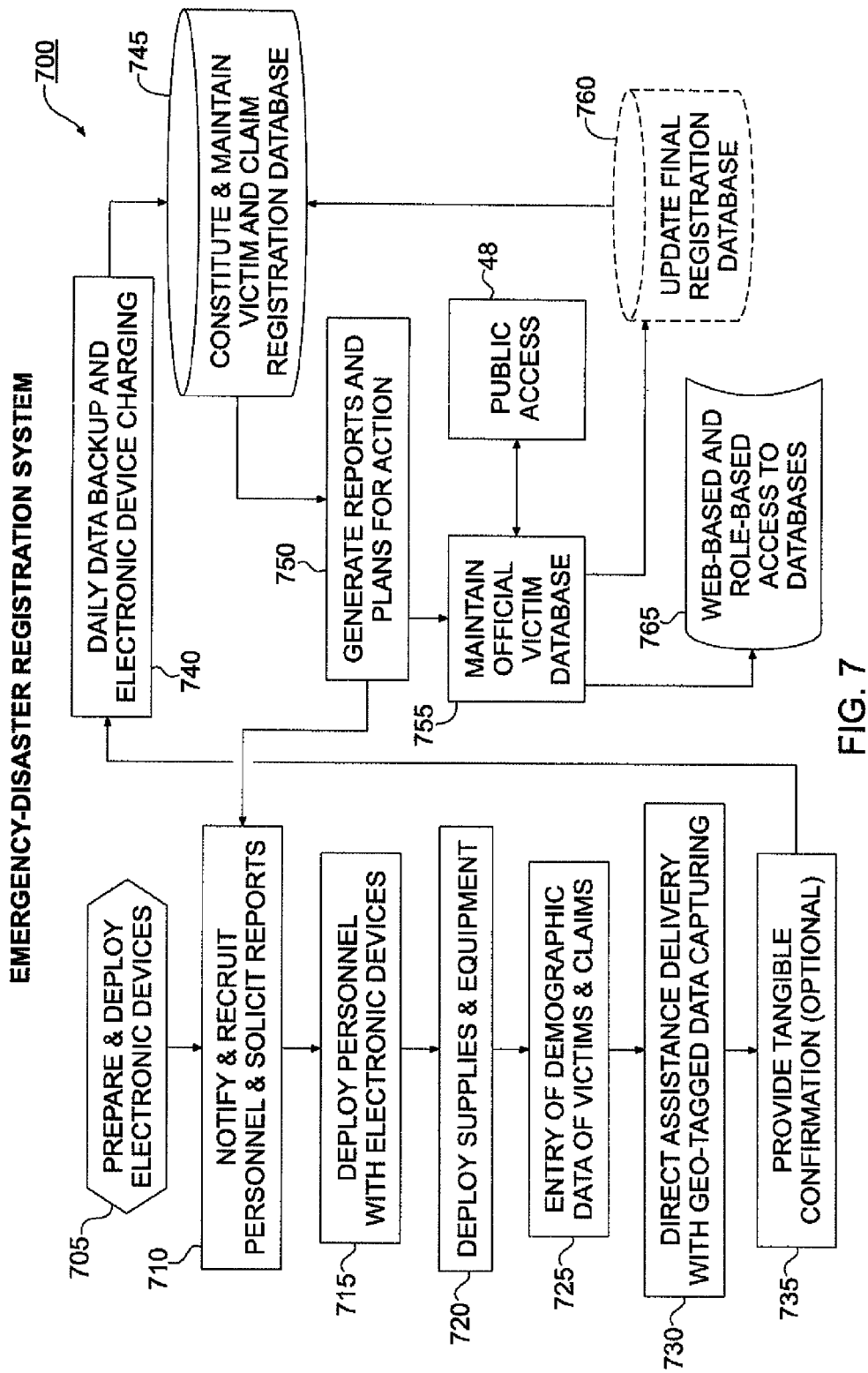
FIG. 7 is a schematic diagram illustrating additional operational functionality of the registration and monitoring system and method of the present arrangement.

FIG. 7 is a schematic diagram illustrating additional operational functionality of the registration and monitoring system and method 10, 700 of the present arrangement. System and process 700 commences with the preparing and deploying 705 of electronic devices 30 which may include, e.g., preparing, testing, certifying, assigning and/or delivering electronic devices 30, e.g., smart phones 30, from a central facility to regional and local facilities. Each electronic device 30 has a software application for performing the data gathering, unique identifier capture, biometric identifier capture, image capture, geo-tagging, and/or date-time stamping of data, and the encryption and/or hashing of data transmissions. Biometric date capture may be provided via the imager and/or touchscreen of device 30, e.g., for facial image capture, facial recognition and/or fingerprint capture, and may also have an associated fingerprint capture device FP as described. By way of preference and not requirement, electronic devices 30 may be recorded in an asset management system, e.g., an asset management database, that may be interconnected with registration and management system 10 and the databases thereof, thereby to advance efficiency, security, monitoring and/or accountability in operation.

Personnel are recruited and notified 710 and/or are solicited 710, as is reporting 710 of conditions, events and the like from persons engaged in operating system 10 as well as persons other than those engaged in operating system 10. Such notification and recruiting is seen to advance the documenting, and reporting of conditions and events of interest in operating system 10 and in registering persons to participate in system 10, e.g., for their own benefit or the benefit of others, at least some of whom may be related to, acquainted with or otherwise connected to the person documenting and reporting.

Personnel and their electronic devices 30 are deployed 715 to seek out and provide assistance and service to persons at or near their assigned locations and/or areas, and to obtain and report data, images, location and other data useful in providing services and/or assistance. Supplies and equipment, such as may be needed by and/or useful to deployed personnel, containers and other packaging therefor, are deployed 720 to predetermined locations, e.g., staging or supply depot areas, from where they are distributed according to needs as determined, e.g., from the data captured and reported by deployed personnel and their electronic devices 30, or from direct requests from such personnel.

Demographic data and other data of persons, e.g., subjects and/or victims, is entered 725 as is data relating to damage, conditions, claims and/or other needs, as part of registration. In data entry 725, a unique identifier is acquired to uniquely identify the person and/or location and/or claim involved. The unique identifier may be generated by the application software of electronic device 30, may be acquired from a national identification card, passport, or other reliable, e.g., government issued, identification, or may be acquired from a data entry e.g., a form 210, that is completed by the person registering. Preferably, but optionally, authorized personnel may assist and review the data entered manually on data entry forms 210 to improve the readability, completeness and accuracy thereof, either in real time or subsequent to the capturing of data using electronic device 30. Optionally limited sufficient to identify the person may be captured from the data entry e.g., a form 210, using the imager of device 30 so as to provide back up in case the data entry e.g., a form 210, is lost before it can be returned to a central location and optically scanned.

While the unique identifier may be entered manually, it is preferred that the unique identifier be captured 725 electronically using the imager of electronic device 30 to capture the unique identifier 220 printed on the data entry form 210, as a readable font, 1D or 2D barcode or the like. Preferably the data entry form 210 includes the unique identifier 220 in a form readable by electronic devices 30 and is an optically scannable form so that the data entered on the form by the person may subsequently be read and captured by an optical document scanner and be associated with image data, biometric identifying data, geographic location data and other data acquired by electronic devices 30 using the unique identifier 220 that is associated with both the optically readable data entry form 210 and the data captured by electronic device 30.

Direct assistance and/or delivery 730 of supplies and/or services may be provided in conjunction with the capturing of geo-tagged data by electronic device 30, thereby to provide necessary assistance both accurately and speedily. Electronic device 30 preferably is utilized to record at least two images: an image of the person assisted and the condition and/or damage being addressed (e.g., preferably in a single image) and an image of the supplies provided and the person receiving those supplies (e.g., preferably in a single image) and the image is geo-tagged and date-time stamped so as to be associatable with (e.g., relatable to) the database records for that person and location. Optionally, the person's fingerprint or other biometric identifier can be captured by electronic device 20 and associated, e.g., by geo-tagging and date-time stamping, and preferably by the unique identifier, with the preceding two images.

Optionally, a tangible confirmation is provided 730a. The tangible confirmation may be by a paper receipt or other tangible record can be produced and provided 730a to the person registering contemporaneously with registering so that the person will have a complete and accurate record of having registered and of the data provided as well as of their unique identifier. This is preferably accomplished by using an optically readable data entry form 210 that has a second sheet which records via physical pressure the marks made on the first sheet thereof, e.g., as by "carbon paper" or "carbonless" copy forms, as are well known.

Data back up 735 and electronic device recharging 735 is preferably performed regularly, e.g., one or more times daily, as personnel check in after their assignments, so that the data captured by electronic devices 30 during such assignments is transferred 740 to more permanent storage devices, e.g., communicated to one or more of local and/or central facilities 50-80 and stored on redundant servers 40, whereby the data therefrom is backed up and database records are created, supplemented and/or otherwise updated, and so that electronic devices 30 are prepared for further use. Electronic devices 30 may be recharged or may receive a replacement battery. In the latter instance, fully or partially depleted batteries are removed from devices 30 and are replaced by fully charged batteries, and the depleted batteries are placed in charging devices for being recharged for future use, e.g., on a like replacement basis.

As part of the regular process 735, the optically readable data collection forms 210 can be received and may be scanned so that the data entered thereon, including the unique identifier 220, is transferred 740 to more permanent storage devices, e.g., communicated to one or more of local and/or central facilities 50-80 and stored on redundant servers 40, whereby the data from forms 210 is backed up and database records are created, supplemented and/or otherwise updated. In scanning data entry forms 220, the data therefrom may be examined for completeness and/or compared to other records, e.g., cross checked with registration records, voting records, driver's license records, and the like, for verifying the data thereon, detecting differences in the data and/or creating follow up tasks to obtain complete and/or corrected data.

Data received as part of the daily or other regular process 735 may be stored on a local computer or server and communicated to a center 50-80 either contemporaneously with the data being received or on a delayed and preferably regular and/or periodic basis, as may be necessary or convenient given the conditions under which the data is being acquired, received and communicated, including the time urgency of creating and updating databases. In an application where rapid assessment and management and response is required, e.g., a flood, tornado or other natural disaster, data reception and communication 735, 740 is preferably more rapid and the time intervals between transmissions, if any, is preferably as short as possible, whereas in less urgent situations, e.g., a vaccination program, they need not be so quick.

Also as part of the regular return 735 process for electronic devices 30, data regarding their use and condition, and of the personnel turning the devices 30 in and the personnel receiving the devices 30 can be entered into an asset management system where such system is employed. Personnel identity may be verified and/or captured by examining and/or scanning personnel badges, ID cards or another identifying item, e.g., as part of the check in and check out process.

Data transfer 740 is employed to communicate data, e.g., data from electronic devices 30 and/or data entry forms 210, to local and/or central facilities 50-80 and servers 40 for constituting and/or maintaining 740 (e.g., updating) databases of persons, e.g., victims, claimants and other registrants, of claims and or other events, and of conditions, e.g., damage, flooding and the like. Communication and transfer of data for constituting and/or maintaining 740 the various databases may occur through transmission of data by electronic devices, contemporaneously with acquisition of the data and/or at delayed regular or irregular intervals, where communication between devices 30 and at least one local or central facility 50-80 is available. Where communication between devices 30 and at least one local or central facility 50-80 is not available, communication and transfer of data for constituting and/or maintaining 740 the various databases may occur when electronic devices 30 are presented for maintenance 740.

In each of the foregoing instances, a date-time stamp will be associated with the data being communicated even if the data already includes a geo-tag and/or date-time stamp, e.g., as will data acquired by an electronic device 30. In addition, and optionally, a data acquisition device identifier may be associated with the data when captured and/or communicated, e.g., an identifier of an electronic device 30, of an optical scanner 250, of a receiving server and/or center, and/or of another device so employed.

Reports and plans are generated 750 from the one or more databases constituted and maintained 740, 745. Generated 750 reports provide information to management personnel for use in planning and managing the responses to the conditions and/or situations, e.g., of personnel, supplies and equipment, whereas generated 750 plans define what should be done in response, e.g., the tasks, personnel, supplies and equipment, and containers and other packaging therefor, that should be deployed. The generation 750 of both reports and plans includes processing data of different types, and possibly from different databases, for defining an integrated and as complete a set of data relating thereto as the data captured in the databases will permit.

Generated 750 reports include tasks and/or actions to be taken and are communicated to electronic devices 30 as notifications 710 to, e.g., personnel in the field, to initiate a suitable response thereto. Because electronic devices 30 have unique device identifiers, e.g., an IMEI, generated 750 communication can be directed to the electronic device that captured data relating to the person and/or location needing assistance and/or further follow up. Similarly, the unique identifier, geographic location and/or personal data relating to the person and/or location needing assistance can also be used in directing generated 750 follow up messages.

Thus, the generating 750 may compare and correct and/or identify any omissions, duplications and/or other discrepancies in the data residing in the databases, thereby to make management personnel aware of potential issues and/or set tasks for personnel to verify and/or correct such data. The data checking may include, e.g., comparing addresses with geo-tag data, comparing names with known accurate data, e.g., verified official government data, and the like. It is noted that plans not only involve direct responses to conditions, but also to identifying geographic areas and/or sites that have not been served, resolving data inconsistencies, to remind personnel of future actions needed and/or needing to be followed up and/or completed, and the like.

System and method 10, 700 may also create and maintain 755 an official database 755 of persons served and/or considered victims. Database 755 preferably is constituted from verified accurate data after errors, omissions and other uncertainties have been resolved, e.g., through completion of generated 750 plans and comparisons of the data with other known complete and accurate records, e.g., one or more verified official government databases, including e.g., voter or other registration, driver's license, social benefit, census and/or other kinds of records.

Updating 755 of databases preferably includes, e.g., mapping of Geographic Information System (GIS) based records, comparison and integration of system 10 database data with other governmental records, e.g., voter registration, census data, driver's license records, and the like. GIS mapping facilitates the correlation and analysis of data that relates to a particular geographic area by overlaying such data on a map of the geographic region to which the data relates, the result generally being a graphic representation on a map. Updating 745, 755 of all databases is preferably performed substantially continuously as new and/or additional and/or updated data is received, and preferably involves updating at all database locations, e.g., facilities 50-80 and servers 40, although all may not necessarily be updated on a real time basis and/or contemporaneously. Optionally, public access 48 may be provided to certain records relating to the program or event being monitored and managed, such as positively verified records of persons affected, as described above.

Web based and role based access 765 is preferably provided to authorized government and non-government personnel with user ID and password protection, preferably with different levels of access commensurate with the need to know of such personnel. Thus, central, national, federal, state, regional, and/or local monitoring is provided, as well as access to data relating to plans, remedies and actions recommended and to be taken, status of plans, remedies and actions, and to reminders and other follow up messages pertaining to them selves and other personnel, thereby facilitating monitoring, accountability, and management of the event and/or occurrence involved.

Figure 8:
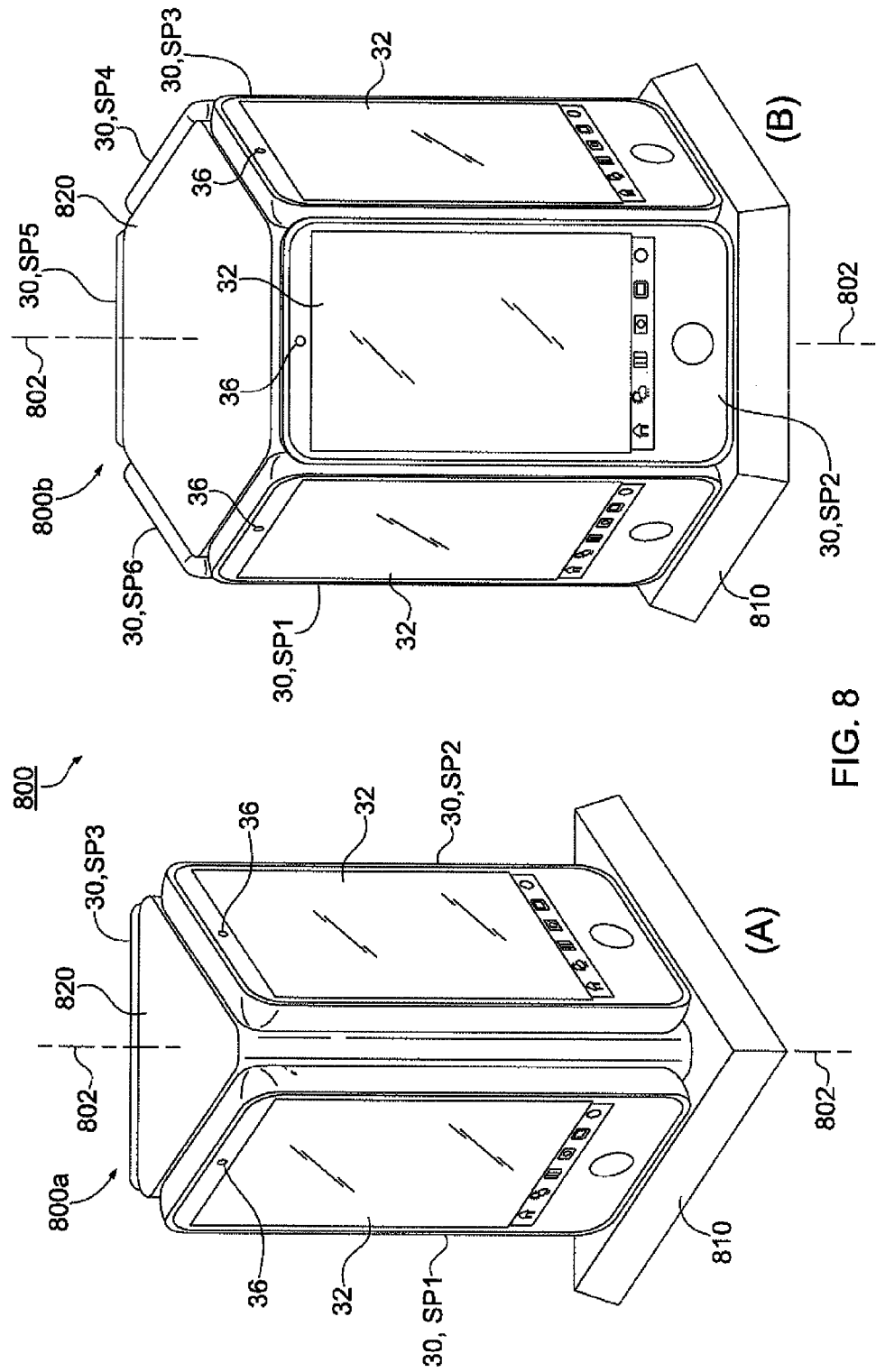
FIG. 8 is a schematic diagram illustrating two example embodiments (A) and (B) of a geographical locating device employing plural electronic devices and suitable for use with the present arrangement.

FIG. 8 is a schematic diagram illustrating two example embodiments (A) and (B) of a geographical locating device 800, 800a, 800b employing plural electronic devices 30 and suitable for use with the present arrangement 10. Geographical locating device 800, also referred to as mapping device 800, preferably may include three to six electronic devices 30, preferably smart phones SP1-SP3 to SP1-SP6, that are mounted to a structure 820 supported by a base 810. While a greater or lesser number of electronic devices 30 may be employed, three devices 30 are seen to provide substantially 360° image coverage with three images with insignificant gaps between images and six devices 30 provide 360° image coverage with six images having overlap between adjacent images.

The selection of the number of imaging electronic devices 30 can be made giving consideration to the use to which the image data will be put and the amount of data capacity, both in transmission and in processing, that is required to process a greater number of images. In addition, and generally, the quantity and accuracy of position locating data will increase as the number of electronic devices 30 increases, which may also influence the number of devices 30 employed. Employing a number of devices 30 greater than six is seen to provide additional images and data that are redundant and that do not contribute substantially to the operation of system 10, and that may even degrade that operation, e.g., by unnecessarily using limited communication capacity and resources.

When base 810 is maintained substantially horizontal or otherwise positioned substantially horizontally, axis 802 is substantially vertical, and each of devices 30, SP1-SP6 is positioned with its face 32 in a substantially vertical plane with its imager 36 pointed radially outwardly in a substantially horizontal direction, thereby to provide a desirable image viewing orientation. Preferably, base 810 includes a device for positioning mapping device 800 in a desired orientation or to an object. For mounting and/or attaching mapping device 800 to a surface, base 810 may include, e.g., a magnet or one part of a hook and loop fastener, e.g., a VELCRO® patch, which is useful for attaching mapping device 800 to a vehicle, e.g., to a hood or roof thereof, or to the hat or helmet worn by a person. Base 810 may also have a recess, e.g., a blind cylindrical opening extending upward along vertical axis 802 thereof, which is useful for placing mapping device 800 onto a pole or stick, e.g., as may be carried by a person or attached to a cart, bicycle or other vehicle.

Devices 30, SP1-SP6 are positioned to be substantially evenly spaced in radial angle about vertical axis 802 of mapping device 800, 800a, 800b, e.g., separated by an angle of 360°/N where N is the number of devices 30. Thus, the three devices SP1-SP3 of device 800a are pointing in radial directions spaced apart by about 120° and the six devices SP1-SP6 of device 800b are pointing in radial directions spaced apart by about 60°. If four devices 30 were employed, their imagers would point in radial directions about 90° apart. Greater or lesser numbers of devices 30 may be utilized, however, with lesser numbers of devices 30 there may be gaps between the scenes captured by their respective imagers 36 and with a greater number of devices, there would be substantial overlap in the scenes captured by their respective imagers thereby producing additional and largely redundant data that would have to be processed and stored with little or no improvement in accuracy and possibly causing a reduction in performance.

In the arrangement (A), mapping device 800a includes three smart phones SP1-SP3 and in the arrangement (B), mapping device 800b includes six smart phones SP1-SP6 that are mounted to a housing 820 so as to be directed in evenly spaced apart radial directions, In operation, each device 30 is operating and is controlled to either periodically capture an image or to capture video images, whereby together the plural devices 30 produce a 360° scene view at each given instant of time.

At the same time, one or more of devices 30 are controlled to acquire the geographical position of mapping device 800, whereby data representing a 360° scene view and a simultaneous geographic location are acquired, e.g., utilizing the GPS capability of one or more of devices 30, thereby to geo-locate the scene views captured by the images. The geo-tagging of image data provides physical location data useful in evaluating on the ground conditions accurately, for sending relief supplies and personnel to the proper location, and for returning to the proper location with relief services and supplies, thereby improving the efficiency of response operations. Thus, the physical location data is preferably employed for geographic information system (GIS) mapping of sites and needs for supplies and personnel.

The rate at which GPS and image data is captured may be fixed, e.g., once per second or other convenient interval given the capacity of system 10 to communicate and process data, or may be variable, e.g., once per second to once per minute, so as to be selectable and/or controllable in consideration of the utilization of mapping device 800. A lower data capture rate, e.g., longer interval, would produce acceptable data coverage where mapping device 800 is be carried on a pole by a person, e.g., once per 30 seconds or once per minute might be adequate, whereas a faster rate would be preferred where the person rides a bicycle or drives a vehicle to which mapping device 800 is mounted. For geo-routing and/or geo-fencing, e.g., of relatively slowly moving people or groups of people as part of a mass movement or pilgrimage, longer intervals, e.g., up to about 5 minutes, or less, might be suitable.

In addition, devices 30 may, and preferably does, date-time stamp the data, so that the substantially simultaneous scene views and geographic (e.g., GPS) location are further particularized to a specific date and time, wherein the date-time stamp is provided by a known accurate source of date and time data, e.g., a communication system or a server. Images may be captured at predefined intervals, with shorter intervals being used when device 80 is attached, e.g., to a motor vehicle, and longer intervals when it is carried by a person on foot or by a bicycle or other slowly moving object.

Accordingly, the scene views, geographic location and specific date and time, may be correlated to other data acquired, e.g., by other devices 30 as described above, to provide a more complete data set representing the condition and situation at a particular place and time. This correlation may be utilized to verify the accuracy of data otherwise collected, and to more accurately connect persons (participants and/or victims) to such locations when they may know or may not be confident of where they are. It is particularly useful when system and method 10 is employed in situations involving natural and man-made disasters where normal location references, e.g., street signs and other landmarks, have been damaged, changed and/or destroyed.

Housing 820 preferably provides more than just support for the plural devices 30, and so may house a battery or other power source for providing back-up or operation-extending power for the plural devices 30. Housing 820 may also have an electrical cable extending therefrom, which may be removable by disconnecting an electrical connector, for obtaining power from an external source, e.g., a power pack or a vehicle. Electrical connections between devices 30 and housing 820 may be provided by connectors at the bottom of housing 820 or on the top of base 810 that mate with connectors of devices 30, e.g., in like manner to when a device 30 is placed into a charger, communication interface or other mounting base device.

Plural device 30 may be controlled to operate substantially independently, e.g., each one determining its own geographic location and timing its own image capture, or devices 30 may be controlled by an external device to operate cooperatively, e.g., in the timing of image capture and/or in having one or two devices 30 determine their geographic location for all of devices 30. Devices 30 may be controlled to operate in a prescribed manner via an external communication link, or by a controller circuit which may be located in housing 820, and the data acquired thereby may be transmitted in real time and/or delayed time, e.g., by the communication facility of devices 30, directly or indirectly to the appropriate center 50-80 where it is to be processed for providing registration and management data. Communication between such controller device and devices 30 may be via a wireless, e.g., WiFi or Bluetooth, link.

Thus, mapping device 800 employs plural electronic devices 30, e.g., common smart phone devices 30, that are controlled by a downloaded application to perform a relatively precise locating and documenting function that can greatly enhance in quality and quantity the data available relating to an event, condition and/or situation and the management of whatever condition and/or situation may be encountered. Data captured by mapping device 800 provides a geo-tagged, date-time stamped record of GPS positions and images captured thereat so that the complete route and timing of personnel and of the supplies and/or equipment they carry, and/or containers and other packaging therefor, and the registration process and its status can be reviewed, monitored, audited and managed.

Figure 9:
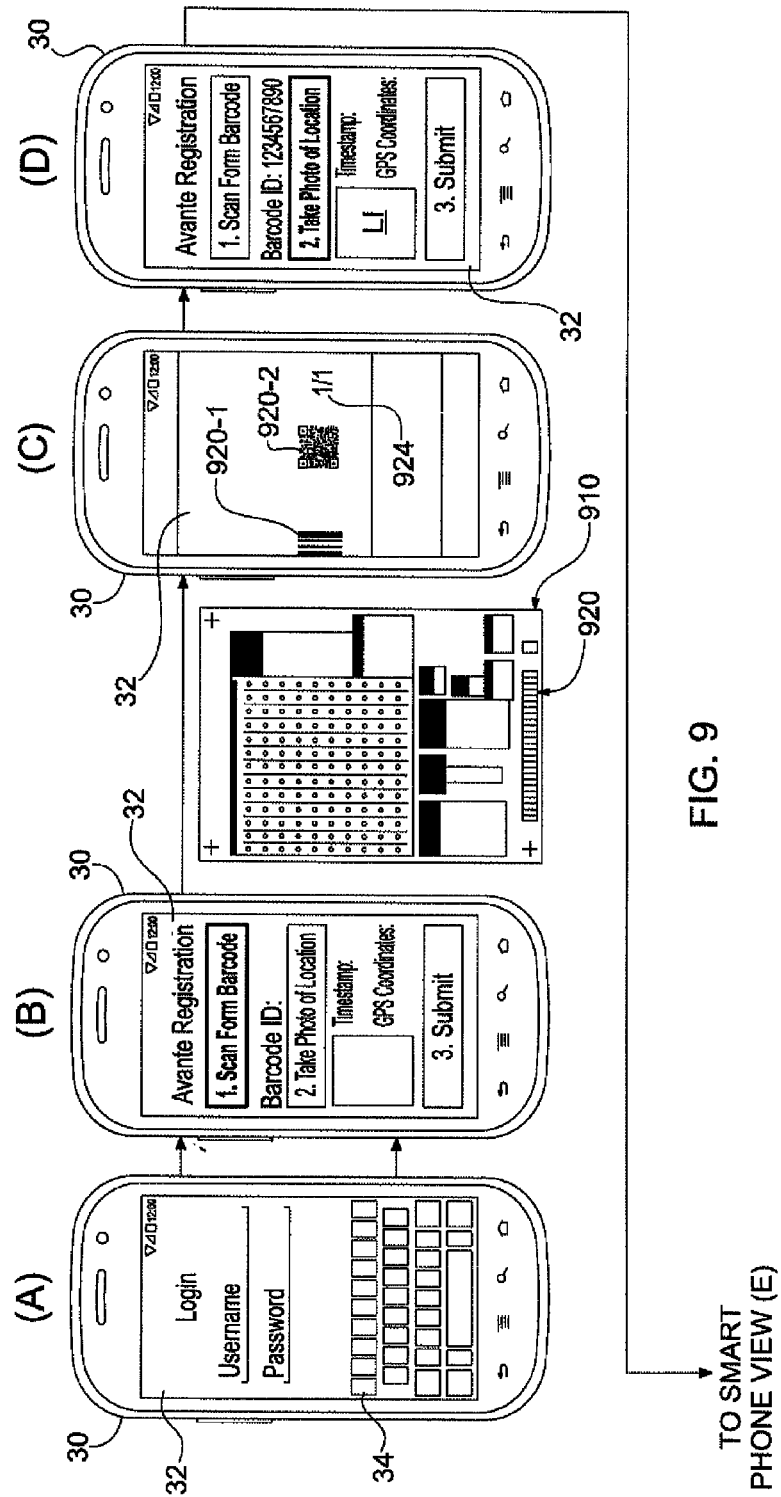
FIG. 9 is a schematic diagram illustrating in a sequence of views of an example registration data entry operation utilizing an example electronic device.
Figure 9:
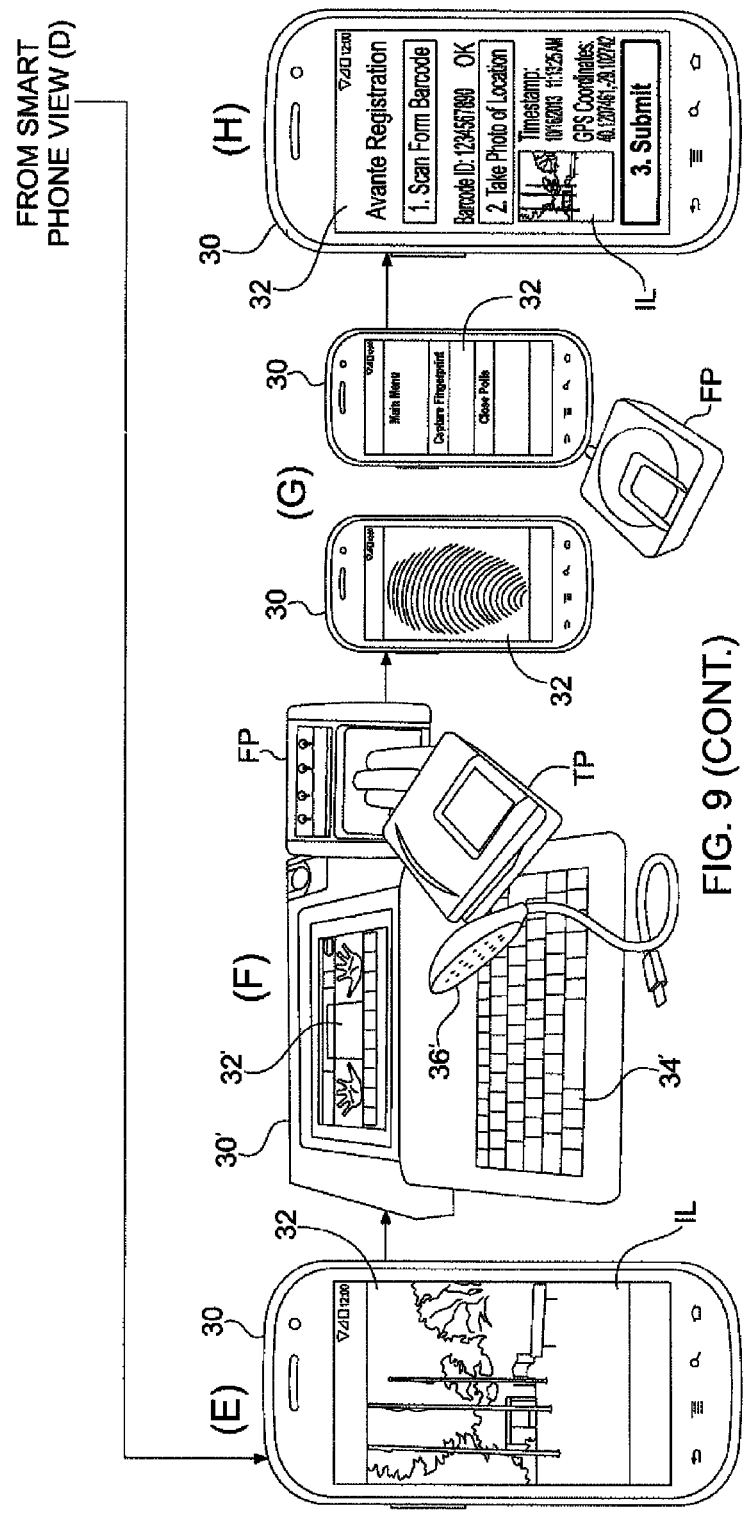
Figure 10A:
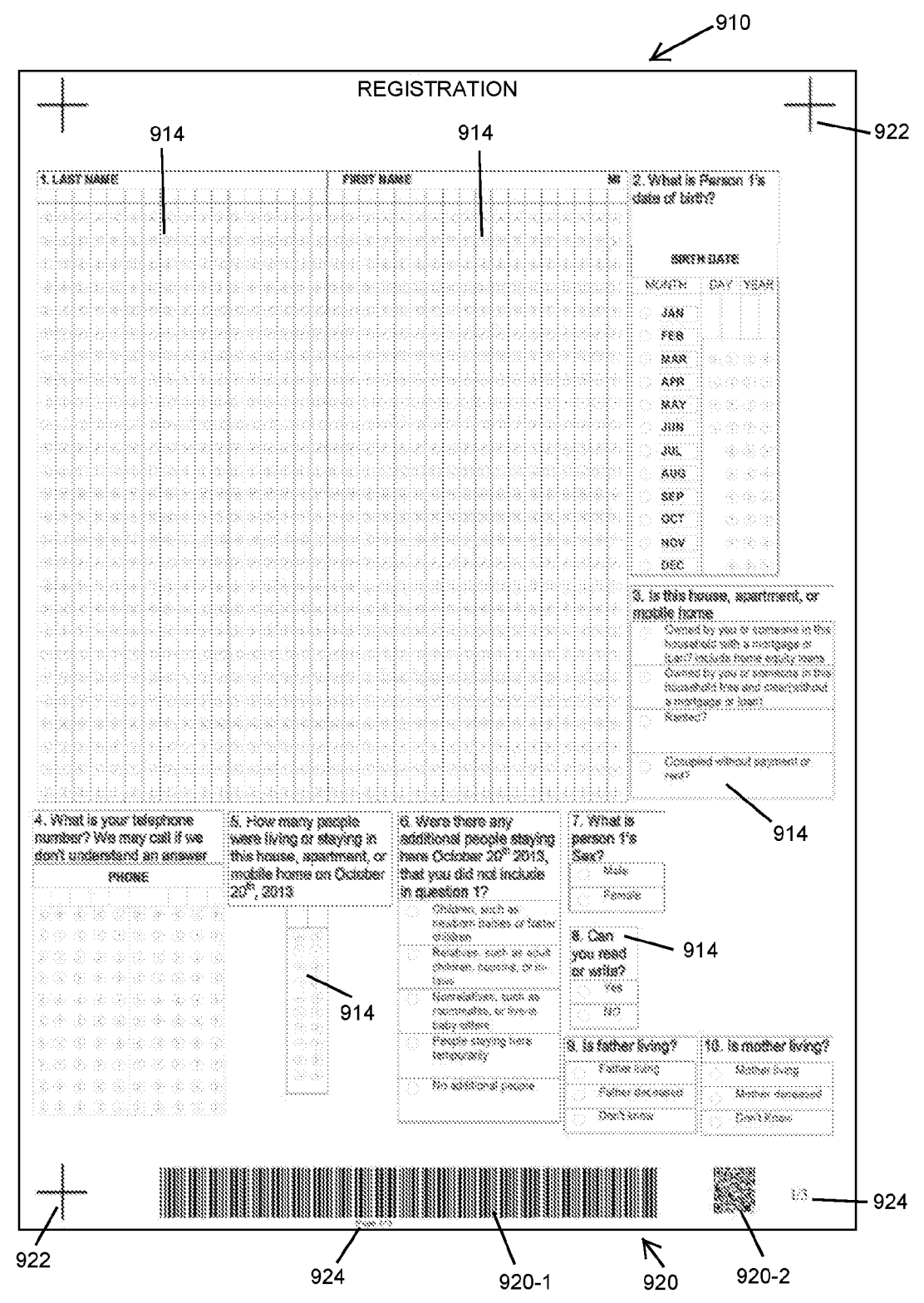
Figure 10B:
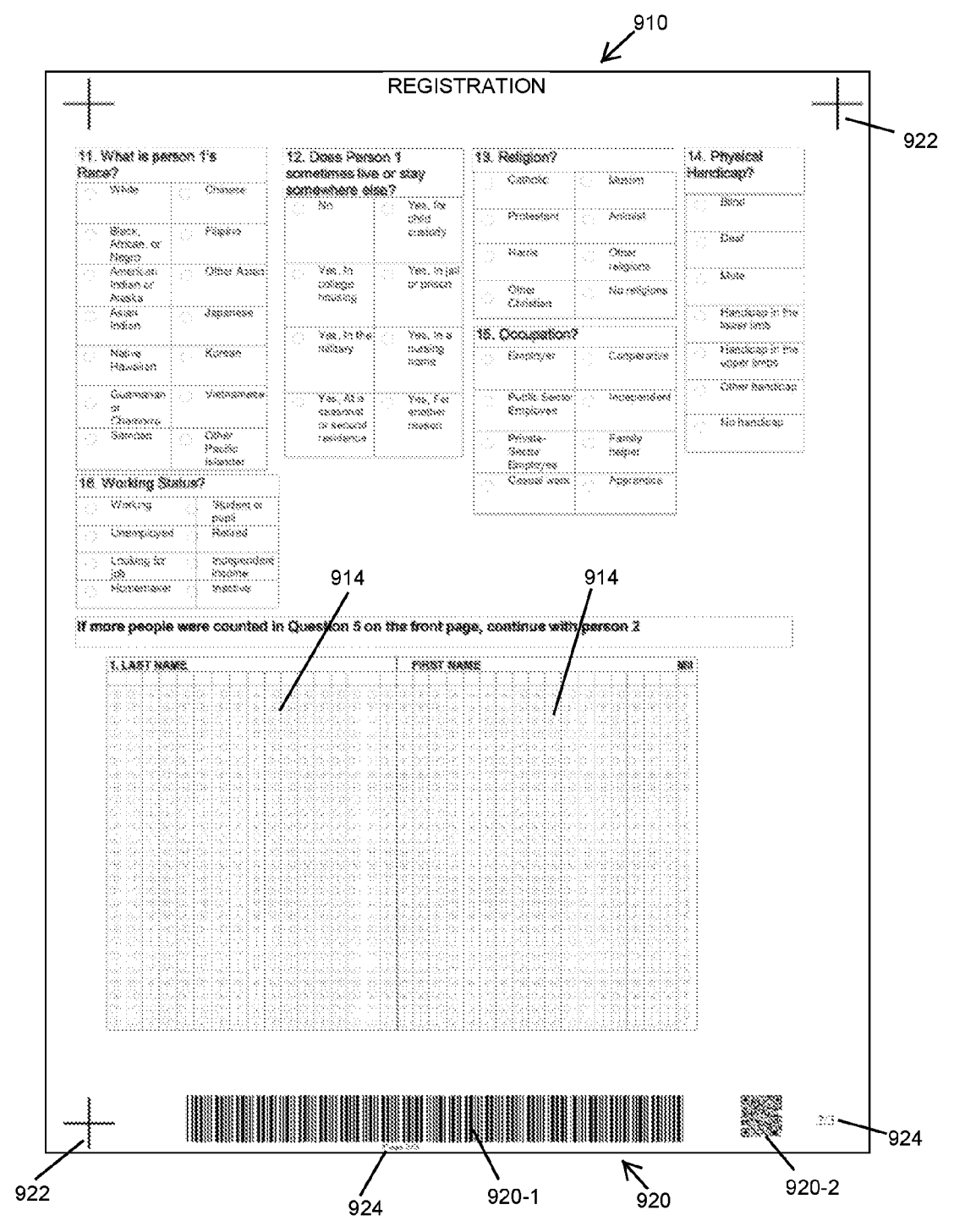
Figure 10C:
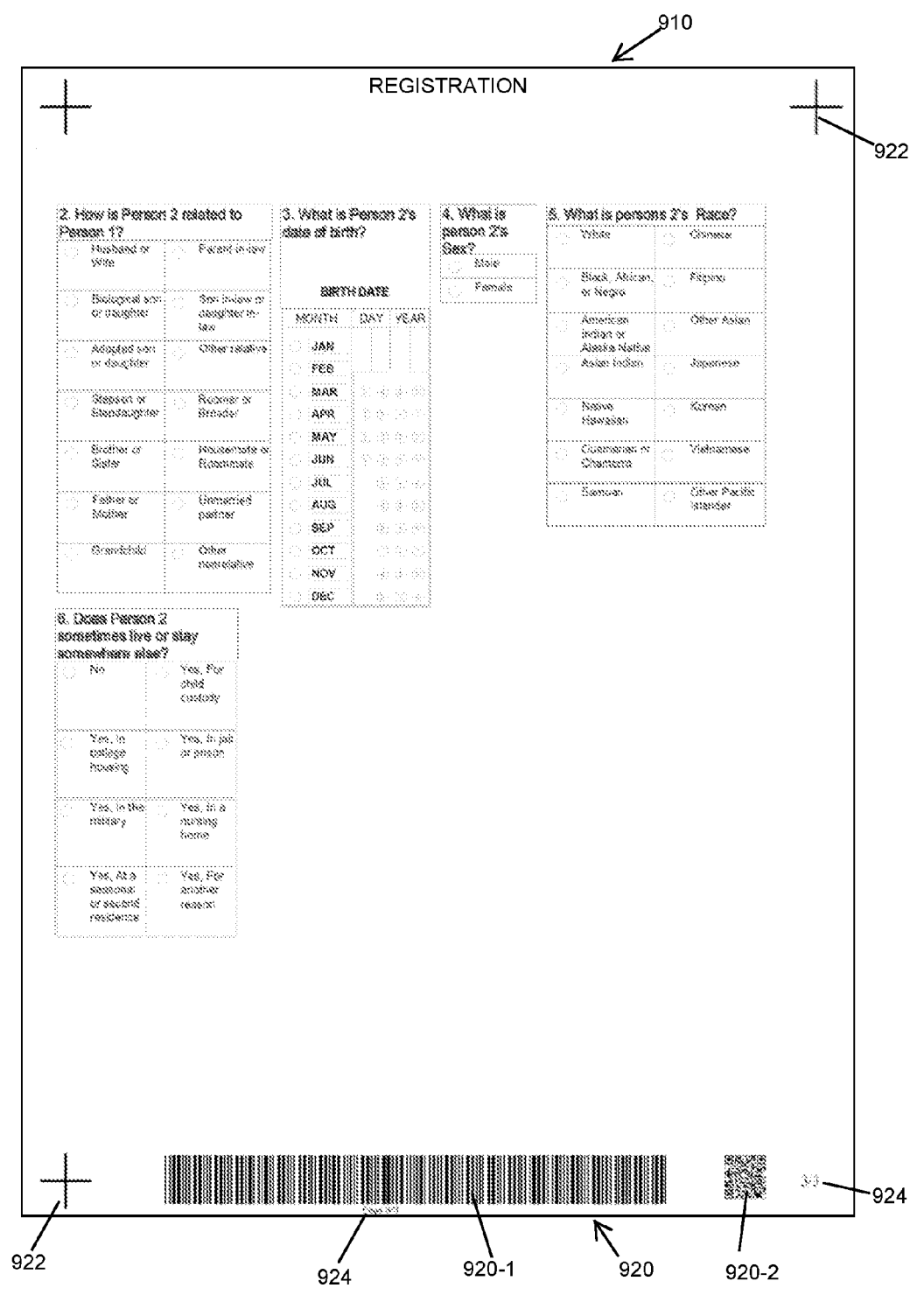

FIG. 9 is a schematic diagram illustrating in a sequence 900 of views (A) through (H) of an example registration data entry operation utilizing an example electronic device 30, and FIG. 10 is an illustration of an example of a data entry form 910 suitable for use with the present arrangement and includes FIGS. 10A, 10B and 10C which illustrate three sheets 910 thereof. The registration operation sequence 900 commences (A) with logging in ("Login") to the registration and management "app" of electronic device 30, e.g., a smart phone 30, by entering a user name, e.g., an identifier for a particular user, and a password via a representation of a keyboard 34 displayed on touch screen display 32 thereof. Upon successful log in, the first registration screen entitled "Avante Registration" representing the program or project is displayed (B) which sets forth the major steps, e.g., here, three steps, in the sequence of the registration operation 900. Data entry and selection among boxes and/or steps is preferably accomplished by touching the appropriate region (e.g., box) on touch screen display 32 to cause the registration "app" to move to that function or feature, as is common in using apps for so-called smart phones and other so-called "smart" devices. In parallel, a registrant has entered data in or enters data in a registration data entry form 910, an example of which is shown in FIG. 10.

Data entry form 910 is preferably an optically scannable sheet or sheets, e.g., here, three sheets, that have a plurality of data entry fields 914 in which identification data, demographic data and other data can be entered, e.g., by marking the mark space regions (e.g., encircled alpha-numeric characters) that spell out the data to be entered. Examples of fields 914 may include, e.g., name (last, first and/or middle), address (street and number, apartment, town, city, state and/or postal (e.g., "ZIP" code), telephone, data relating to personal and/or location related facts, contact information (e.g., telephone, cell phone, e-mail address), and the like.

Each data entry form 910 includes a unique identifier 920 which is printed thereon, e.g., as a barcode 920 (e.g., a one-dimensional (1-D) barcode 920-1 and/or a two-dimensional (2-D) barcode 920-2), in an optically readable font, and/or in a human-readable font. In illustrated example data entry form 910, both 1-D and 2-D bar codes 920-1, 920-2 are printed at the bottom of each sheet of data entry form 910. Where a data entry form 910 includes plural pages, the page number 924 of each page is preferably printed thereon, e.g., "Page 1 of 3" or Page 1/3, etc., in an optically readable form and may also be encoded into the barcode 920. One or more optically readable fiducial marks 922 or other orientation indicating marks 922 are preferably provided so that the orientation of data entry form 910 may automatically be determined when form 910 is optically scanned and read (decoded).

In step (B) the first step "1. Scan Form Barcode" is highlighted, colored, brightened, and/or otherwise made evident on display 32 (indicated in the drawing by a bold line box) so as to identify the action required and to lead the user through the registration operation sequence 900 on a step-by-step basis, thereby to reduce the level of skill necessary to perform the operation and to improve the likelihood that the operation will be completed properly and successfully. Below the highlighted step a region may be provided for displaying the identity, e.g., title, of the data to be captured, e.g., "Barcode ID" and once the data is captured, which in the case of the barcode involves capturing an image of the barcode 920 using the imager 36 of electronic device 30, the captured data image is displayed (C) on display 32 to verify to the user that the image has been captured and is decoded by the registration "app" and the decoded data is displayed (D) in alphanumeric form with the title thereof.

Upon successful capture of data in any step, e.g., capture of the unique identifier data as above, the highlighting or other emphasis of the first step is removed and the region indicating the next step is similarly highlighted or otherwise made evident (indicated in the drawing by a bold line box). In registration operation sequence 900 the next step (D) is "2. Take photo of location" which becomes highlighted and again involves capturing an image using the imager 36 of electronic device 30. A box LI with wording Location Image or similar is provided to receive the image. When an image is captured, the captured image IL, e.g., of a location and/or person, is displayed (E) on display 32 for review by the user. If the image is acceptable, e.g., indicated by touching an icon on screen 32, the image may be reduced to a thumbnail IL and displayed below the highlighted step (H); if not acceptable, another image may be taken. The location of device 30 at the time the location image is captured (E) is obtained by the registration "app" from the location identifier feature of electronic device 30, e.g., a GPS locator, and/or a date-time stamp may be obtained from a known accurate source of time and date data. and one or both may be displayed (H) adjacent to the thumbnail image.

At this point the mandatory data capture may be considered complete and the highlighting or other emphasis changes from the present step, e.g., the Barcode scan (D) step, to the next step, e.g., the "3. Submit" step (H) box. Touching the submit box causes the registration "app" to store the data entered into and captured by electronic device 30 in a memory of device 30 and/or to transmit the data entered into and captured by electronic device 30 to a data collection entry location, e.g., a local and/or central command center 50-80, for storage, association with data obtained by scanning and decoding data entered on a data entry form having the same unique identifier associated therewith, and storing such data in a relational database from where it may be accessed, e.g., for review, monitoring and/or management purposes, and processed, e.g., for generating, implementing, and following up on actions, tasks, supplies, equipment and the like as may be appropriate in responding to the event, events and/or conditions that have been reported.

Each data transmission from an electronic device 30 preferably not only has the unique identifier matching the unique identifier from data entry form 210 associated therewith, but also has an identifier of electronic device 30, e.g., an IMEI or other device identifier, associated therewith, whereby the transmitted data is not only relatable to other data by the unique identifier from form 210, but is also relatable to a particular electronic device 30, which facilitates follow up communication, e.g., requests for missing and/or additional data, tasks and/or actions needing to be taken, provision of supplies and/or equipment, being transmitted via the one or more electronic devices 30 that were involved with capturing and reporting the data upon which such follow up is based.

Follow up actions are generated automatically from the verifiable database data reports and are automatically transmitted to the appropriate entities and responders, and to sources of supplies and/or equipment, and of containers and other packaging thereof, all in accordance with the web-based database for predetermined responses to reported verifiable conditions. Moreover, all of the captured data, images, reports, provision of supplies, equipment and/or services, generated task and action orders, data relating to the status, partial fulfillment and/or completion thereof, inventories of supplies and equipment and of containers and other packaging therefor, and the like are all accumulated and available in the relational databases for review, planning, revising, auditing and otherwise monitoring and managing whatever events, conditions and/or responses have occurred.

Optionally, biometric identifiers may be captured during the registration process 900 as thus far described. To that end, biometric identifying data, e.g., a facial image or a fingerprint, may be captured and associated with the unique identifier and thereby with the other data captured. Facial images and fingerprints may be captured (F) by an electronic device 30' provided for the purpose of capturing such data, e.g., a laptop, tablet or other portable computer 30', that either includes the necessary devices, e.g., an imager and/or touch pad, or that has associated devices, e.g., a touch pad TP, fingerprint scanner FP, imager 36' and/or other device, suitable for capturing the desired data. Preferably in most instances, facial images and fingerprints may be captured (G) directly by electronic device 30, e.g., by the imager thereof, by the touch screen thereof, by an accessory device FP, or other suitable device. In either case, it is preferred that the captured data, e.g., an image and/or fingerprint, be displayed on a display device 32, 32' of electronic device 30, 30', for review and confirmation, e.g., that its quality is acceptable.

Following registration and where supplies, equipment, services and/or any other response is to be provided, the provision thereof is preferably documented in similar manner to the initial registration and preferably includes utilizing electronic device 30 to, e.g., capture geo-tagging data and image data of the places and/or persons receiving supplies, equipment, services and/or other response, provide a date-time stamp thereof, capturing biometric data identifying the recipient, and capturing image and other data useful for updating previously captured data relating to the condition and/or event and/or the person(s) involved. Such updating is preferably generated by personnel who are acting in response to tasks and/or other actions generated by system 10 from the data in the one or more databases thereof and communicated to such personnel via electronic devices 30 or other means.

Figure 11:
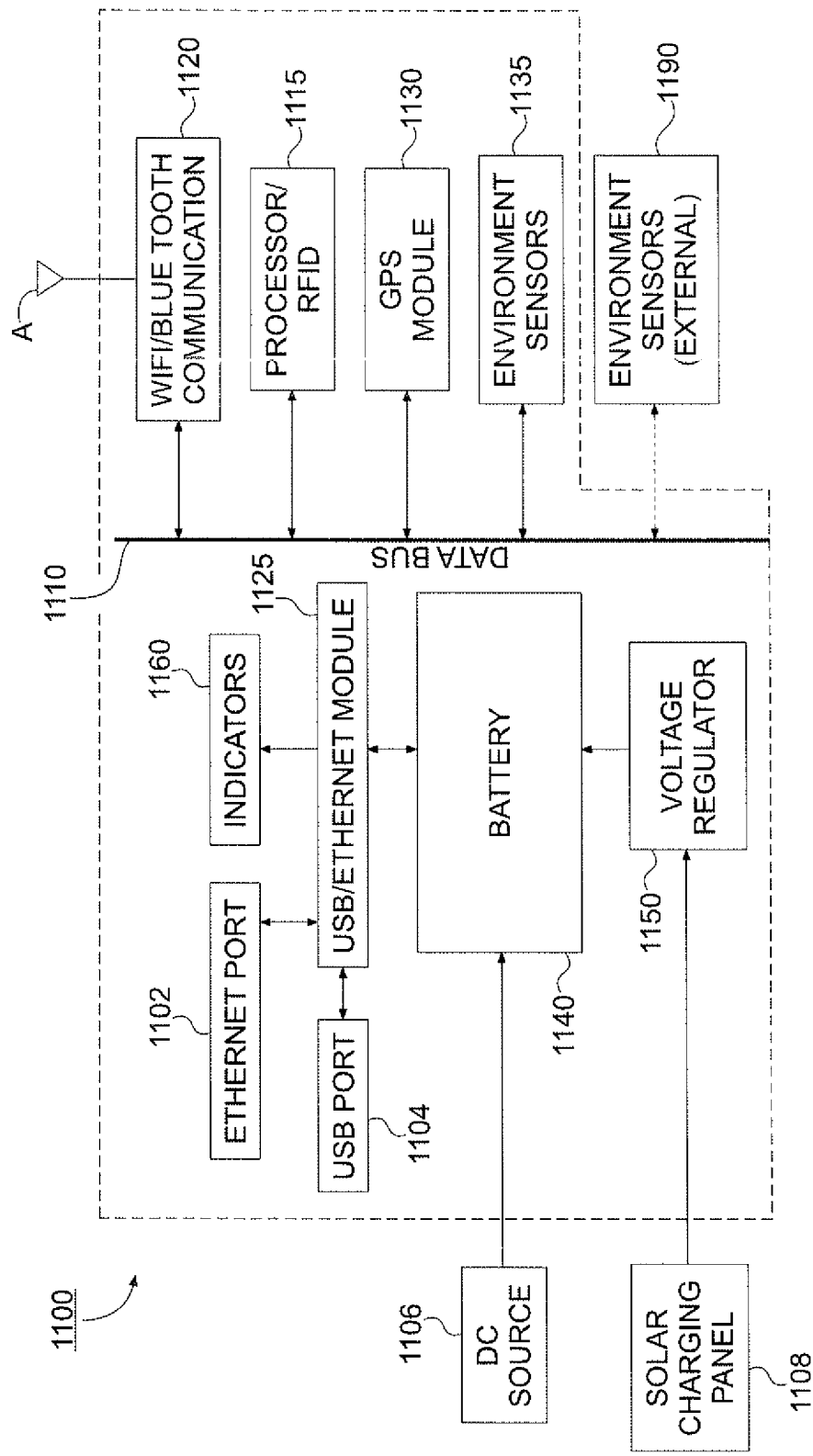
FIG. 11 is a schematic diagram of an example electronic device that can operate with RFID devices in the example registration and management system and method.

FIG. 11 is a schematic diagram of an example electronic device 30 that can operate with RFID devices in the example registration and management system and method 10. Certain articles may have limited useful lifetimes and/or may be subject to deterioration and spoilage that depends upon not only time, but also the environment and conditions to which they are exposed. In the context of the present system 10 being employed for responding to a disaster or emergency, e.g., a natural disaster or a man-made disaster or emergency, food and medical supplies may need to be delivered while still fresh and/or may be required to be refrigerated or kept in a dark place to reduce and/or retard deterioration and spoilage. In the context of system 10 being employed for property management, e.g., of inventory, equipment, containers, packages, inventory and/or other supply chain items, vehicles, files and/or other movable property, finding the property after it has been moved, especially if a substantial time has passed, presents an additional problem, e.g., in that the articles of property preferably should be able to respond if necessary to facilitate their being located. In the context of system 10 being employed for a mass vaccination or other medical mission, vaccines and medications may need to be refrigerated and/or kept in the dark to preserve efficacy and/or avoid degradation and/or spoilage. This problem is particularly acute where such mission is performed under "primitive" conditions, e.g., where refrigeration is provided by cold packs and insulated containers rather than modern actively controlled refrigeration. In such situations and conditions, system 10 is advantageously provided with devices that monitor and report data relating to, e.g., various environmental and/or other conditions, and location.

One preferred device includes an RFID device that includes or is connectable to sensors of the parameters of concern, e.g., sensors of temperature and/or humidity and/or light, and that communicates with electronic devices 30 or other communication facilities for transmitting the data values monitored to various entities and/or agencies, such as those described above. A RELAYER™ RFID module 1100 includes the various devices, elements and functions needed to perform the monitoring and reporting operations described. Communication among and between the various elements of module 1100 is via an internal data bus 1110 which is connected to such elements for the transmission of data therebetween.

External communication with module 1100 is principally via ethernet connection 1102 and/or USB port 1104, which interface with databus 1110 via USB/Ethernet interface device 1125, and/or antenna A. Antenna A may be, e.g., a 2.4 GHz ceramic antenna, for external communication between external WiFi and/or Blue Tooth networks and WiFi and/or BlueTooth interface module 1120 which can transmit, e.g., data received thereby via databus 1110, and receive instructions and/or programming for module 1100.

Internal to RFID module 1100 are an RFID processor 1115 that communicates and processes RFID signals and related data, e.g., responding to inquiries and transmitting data packets when appropriate, e.g., to establish and maintain a network connection and/or transmit data and/or alarms. GPS module 1130 determines the location of device 1100 and environment sensor 1135, e.g., temperature, humidity and light sensor 1135, monitors and stores sensed values of environmental parameters, e.g., temperature, humidity and/or light, which are time-stamped, e.g., using a time-date standard that is received from a known accurate external source or is periodically synchronized to such source. Environmental and/or condition data from sensing module 1135 and/or similar data from optional external temperature, humidity and light sensor 1190 is communicated via databus 1110 and is stored and/or communicated as described.

Module 1100 receives operating electrical power from an internal source 1140, typically a battery 1140, and preferably a rechargeable battery 1140. A preferred battery in one embodiment includes a rechargeable 3.3 volt Lithium battery, which may be recharged, e.g., by an external 5-16 v. DC source 1106 or from an external solar panel 1108 which are interfaced with battery 1140 by a charging voltage regulator 1150 which cooperates with protective circuitry of battery 1140 to reduce and/or convert the incoming voltage, e.g., 5-16 volts from source 1106 or up to 12 v. from solar panel 1108, to proper voltage and current levels for safely charging battery 1140. Alternatively, a supplemental battery 1106 and/or solar panel 1108 may be provided as part of device 1100, internally thereto.

One or more LED indicators 1160, e.g., eight LEDs 1160, may be provided for indicating the status and/or other operating condition of device 1100, and/or its connection or lack of connection to one or more external communication links, e.g., WiFi, Ethernet, Internet and the like. It is noted that a substantial part of RFID device 1100 may be provided using the operating parts from a smart phone and/or other wireless communication device, e.g., an internal circuit board, that includes a substantial number of the described elements of device 1100, e.g., battery control circuitry, wireless network and/or USB interfaces, GPS locating circuitry, environment sensing devices, and the like.

The RELAYER™ RFID module 1100 which by virtue of its various external communication capabilities can serve as a relay station for simpler RFID devices typically may operate in conjunction with such RFID devices, sometimes referred to as ZONER™ RFID devices. The ZONER™ RFID devices are RFID tags that include one or more sensors, e.g., temperature, humidity and/or light sensors, that are placed, e.g., on medication containers, for monitoring and storing data relating to the medication contained by such containers, including the transmitting of data to alert personnel that the medication has been exposed to an out of limit environment. One example of an out of limit environment might occur when a cold packed insulated container remains open for too long a time so that the temperature of the contents thereof (and the RFID tag thereon) rises above a predetermined threshold, and often the circumstances thereof can be determined from correlating data from another sensor, e.g., a light sensor, which may indicate that the cover was completely off or was not tightly closed.

In such vaccination or environment sensitive application, data entry forms 210 may be used and are tailored to capture information relating to the vaccination and/or the person or persons being vaccinated, which may include entering data for related persons on the same form, all of which is related to images, geo-tagged location data, date-time stamp data, RFID data and RFID sensor data captured by electronic device 30 by the unique identifier printed on data entry form 210 and captured by the imager of electronic device 30. Preferably minors are registered with their parent or guardian or other responsible adult, e.g., using the same data entry form 210 and the unique identifier associated therewith and captured by imaging the data entry form 210 using electronic device 30.

Preferably, the RFID tag serves as or is included in a label for the medication container and has an identifying number and/or barcode printed thereon which is also imaged by device 30 for every dose dispensed, thereby to further improve quality, auditability and accountability, e.g., by enabling doses of degraded and/or ineffective medications to be identified and follow up actions to be generated and communicated, e.g., so that re-vaccination with an efficacious dose may be ordered and administered. Coupled with such data being correlated with the geo-tagged and date-time stamped data stored in the system 10 database, e.g., using the unique identifier thereof, also facilitates identifying the person who received the ineffective dose and their location, thereby enabling the re-dosing action order to be generated and communicated to personnel in best position to actually carry out the administering of the follow up dose, even where the locating and identifying of the person may be difficult.

Preferably, an image, and also preferably another biometric identifier, of the person being vaccinated and/or otherwise being treated is captured and in addition an image of the administration of the vaccination and/or treatment is captured by electronic device 30 for verification of the delivery of the vaccination and/or other medical service, and for quality control, auditability and accountability. Such data and the data provided via module 1100 may be utilized for generating and maintaining accurate information regarding the progress and thoroughness of the vaccination program, as well as the quality thereof, and is all related by the unique identifier, thereby to produce a complete and relatable record in the one or more relational databases of system 10.

Further, personnel may be provided with an RFID identification card or badge that can be read by the RELAYER™ RFID module 1100 and/or another RFID scanner for being associated with the data captured by an electronic device 30 and personnel location, and/or their equipment may likewise be provided with an RFID tag or label by which it can similarly be associated with data captured, personnel and/or location, whereby virtually complete monitoring and tracking of events and the response thereto may be accomplished, including an inventory of personnel and equipment, and containers and other packaging therefor.

Still further, data from the RFID labels associated with perishable supplies can be monitored and utilized, e.g., by a central location 50-80, to determine and monitor, essentially in real time, the condition of such supplies. Data from the labels thereof may be captured by one or more RFID readers, e.g., an RFID device 1100 and/or an RFID reader associated with an electronic device 30, or by scanning the label barcode or capturing an image of the label, e.g., using the imager of device 30, which data is then associated at least with the device 30, 1100 and thus the location, e.g., via the GPS data or other location data.

Where such supplies have or may soon be expiring, losing efficacy or otherwise becoming spoiled, e.g., as a result of the passing of time and/or exposure to temperature, humidity, light or other condition, a follow up action is generated and forwarded to the one or more proper electronic devices 30 advising personnel to discontinue using the degraded or otherwise undesirable supplies and to obtain and/or use replacements therefor. The one or more proper electronic devices 30 are determined using the unique identifier, the identifier of the device 30, GPS or other location, and/or other data that has been communicated to a central location 50-80 and is resident in the one or more databases thereof.

It is also noted that the periodic determining and reporting of physical location, e.g., GPS locating and geo-tagging of data, of personnel, of electronic devices 30, and of supplies and equipment, and containers and other packaging therefor, also permits geo-tracking of their locations so that coverage of particular routes, areas and/or regions, of personnel and equipment, may be monitored and managed, and so that any appropriate tasks, actions and/or supplies may be ordered and dispatched, and/or reminders and other follow up instructions may be sent.

Figure 12:
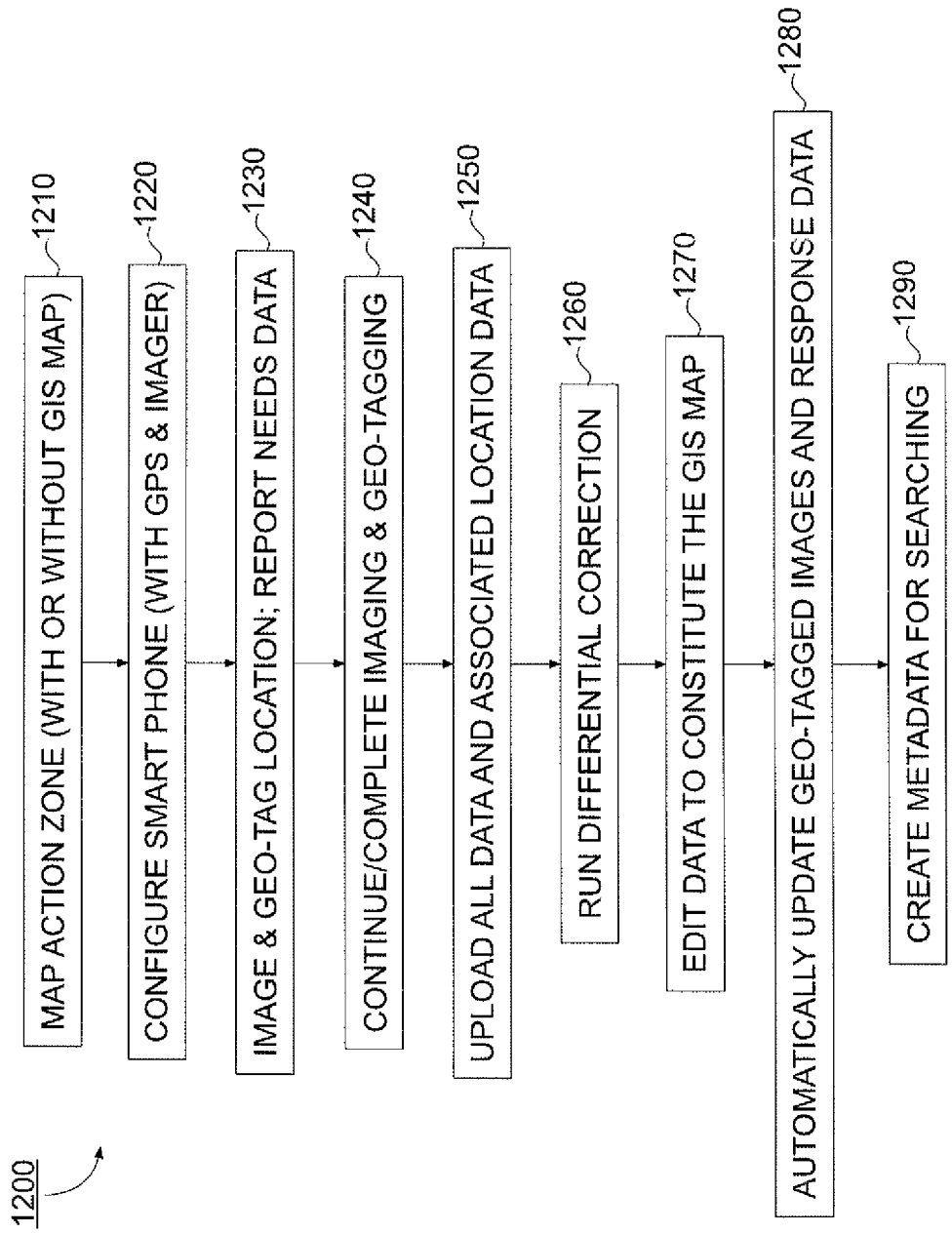
FIG. 12 is a schematic flow diagram illustrating the GIS mapping process associated with the example registration and management system and method.

FIG. 12 is a schematic flow diagram illustrating the GIS mapping process 1200 associated with the example registration and management system and method 10. Therein, process 1200 commences with mapping 1210 of the action zone, e.g., the geographic locale or region, wherein the registration or other action, e.g., census, vaccination, disaster relief and the like, utilizing registration and management system 10 is to take place whether or not a detailed GIS map has been completed. Local or regional or central staff is assigned 1210 to map the designated area, e.g., by a government or other entity, and proceed to receive one or more electronic devices 30, e.g., smart phones, tablet computers or similar devices 30. Electronic devices 30 each have an imager and a locator function, e.g., a GPS module, and that are configured 1220 to be easily transported through a region for capturing contemporaneous location images and GPS coordinates that are associated with the corresponding image and with a corresponding date-time stamp, e.g., as described above in relation to mapping device 800 which can be transported by a person or on a vehicle.

Preferably, mapping 1210, 1220 commences at a predetermined known location, e.g., an intersection of roads or a bridge or another distinctive physical object, or at predetermined known GPS coordinates, and proceeds as one or more mapping devices 800 are transported along one or more routes therefrom with mapping data, e.g., correlated images, GPS location and date-time stamp, captured periodically, e.g., at intervals of once per second, as may be suitable for a vehicle mounted device 800, or of once every 30-60 seconds, as may be suitable for a device 800 carried by a person. The foregoing mapping functionality may be and preferably is provided by smart phone application software (known as an "app") and may operate essentially continuously throughout the deployment of devices 800.

In addition, registration 1230 of individual people (e.g., in a census or vaccination program), actions (e.g., vaccination or damage reporting) and/or sites (census, vaccination and damage reporting) is performed by capturing an image 1230 and a geo-tagged location thereof, e.g., using an electronic device 30. In a vaccination program context, e.g., geo-tagged and date-time stamped images are preferably captured of the person to be vaccinated (of an individual or of a child with its parent or guardian), of the administering of the vaccination, of the vaccine container and label, and a geo-tagged date-time stamped biometric identifier of the person, e.g., a facial image and/or fingerprint, may also be captured.

While the electronic device 30 that is utilized to capture such images and data, e.g., of a person and vaccine, may be one of the devices 30 of mapping device 800, a separate electronic device 30 may be employed. In addition, if any need is identified, e.g., for medical supplies or treatment, for relief supplies and/or equipment, containers and other packaging therefor, and the like, such data concerning need is reported via device 30 via communication to a center 50-80 where it is entered into the database, processed and used to order and dispatch the needed personnel, actions, supplies and equipment.

Process 1200 continues 1240 with the imaging and geo-tagging of images and data 1230 at each location along the predetermined route, e.g., at each dwelling or residence or other building or structure, until the entire designated area or region is completed and the needs of all within such area or region have been captured in data, reported and processed. Typically, the route over which the registration and mapping personnel are assigned to travel ends at a predetermined known location or at predetermined known GPS coordinates. In primitive and remote regions, such locations could be a stream crossing, a village, a group of huts, a large rock, or a similar feature.

All data captured, all images and all related location data, including associated GPS geo-tagging and date-time stamps, is uploaded 1250 to a central facility 50-80 for storing in the one or more relational databases thereof, thereby to complete the capturing of data needed for a complete registration, census, vaccination program, disaster evaluation and relief effort, and the like. Inherent in such data is the data needed to generate tasks and actions for follow up, e.g., via the dispatching of personnel, supplies and/or equipment, and containers and other packaging therefor, along with geo-tagged data as to where such personnel, supplies and equipment is needed, and to communicate such tasks and actions to the appropriate personnel via their electronic devices 30.

Geo-tagged data is corrected 1260 by comparing the data captured with related data from other sources, e.g., a previous census, registration roll, driver's license registry, and the like. Such differential correction 1260 identifies differences both actual and due to data error, that can then be addressed, e.g., via follow up requests communicated to personnel via their electronic devices 30 to check the data or to capture additional (and hopefully) accurate data. Because the captured data is geo-tagged and date-time stamped, differential data correction may employ analytical software such as the GPSAnalyst extension of the ArcGIS software; ArcGIS software, and equivalents and substitutes therefor, can be downloaded via the Internet from many sources, including, e.g., Environmental Services Research Institute, Inc. of Redlands, Calif. and many other web sites.

Then, the data is edited 1270 to constitute one or more GIS maps, e.g., utilizing the ArcGIS software, that encompass all of the data captured 1230-1250 for the regions or regions involved and that are available via the central facilities for review, monitoring, analysis and management of the registration and service provision process 10.

As additional data is captured 1230-1250 and processed 1250-1270, the one or more data bases of centers 50-80 are automatically updated 1280 by the addition of further geo-tagged and date-time stamped images and other data, including response data captured in responding to tasks, actions and other follow up generated from the database records. One example of this is the continual updating of vaccination records which both assures that a complete vaccination sequence has been completed, that the vaccines used were efficacious, and that any booster or follow up action is generated and communicated for action.

As part of the updating 1280 or as a separate step, metadata is generated 1290 from the database records within the one or more web-based relational registration databases for facilitating the searching and sorting of such records, e.g., for review, analysis, and management purposes. In addition, such database records may be utilized for providing geo-routing and/or geo-fencing and/or otherwise monitoring for persons, personnel, supplies and/or equipment, containers and other packaging therefor, e.g., for follow up, inventory, accountability, analysis, and/or for future programs.

The system 10 and method 10 described herein finds useful application for a wide variety of purposes, situations conditions. As already mentioned above, system and method 10 may be utilized for responding to a wide variety of natural and man-made disasters, emergencies and other events, e.g., storms, earthquakes, tsunamis, tornadoes, hurricanes, typhoons, releases or leaks of toxic gases and other toxic materials, environmental contamination, and the like, and for various programs involving relatively large numbers of people, e.g., census, population registration, refuge relief and family association, mass vaccination programs, medical response situations, relief programs, mass pilgrimages, and the like.

Figure 13:
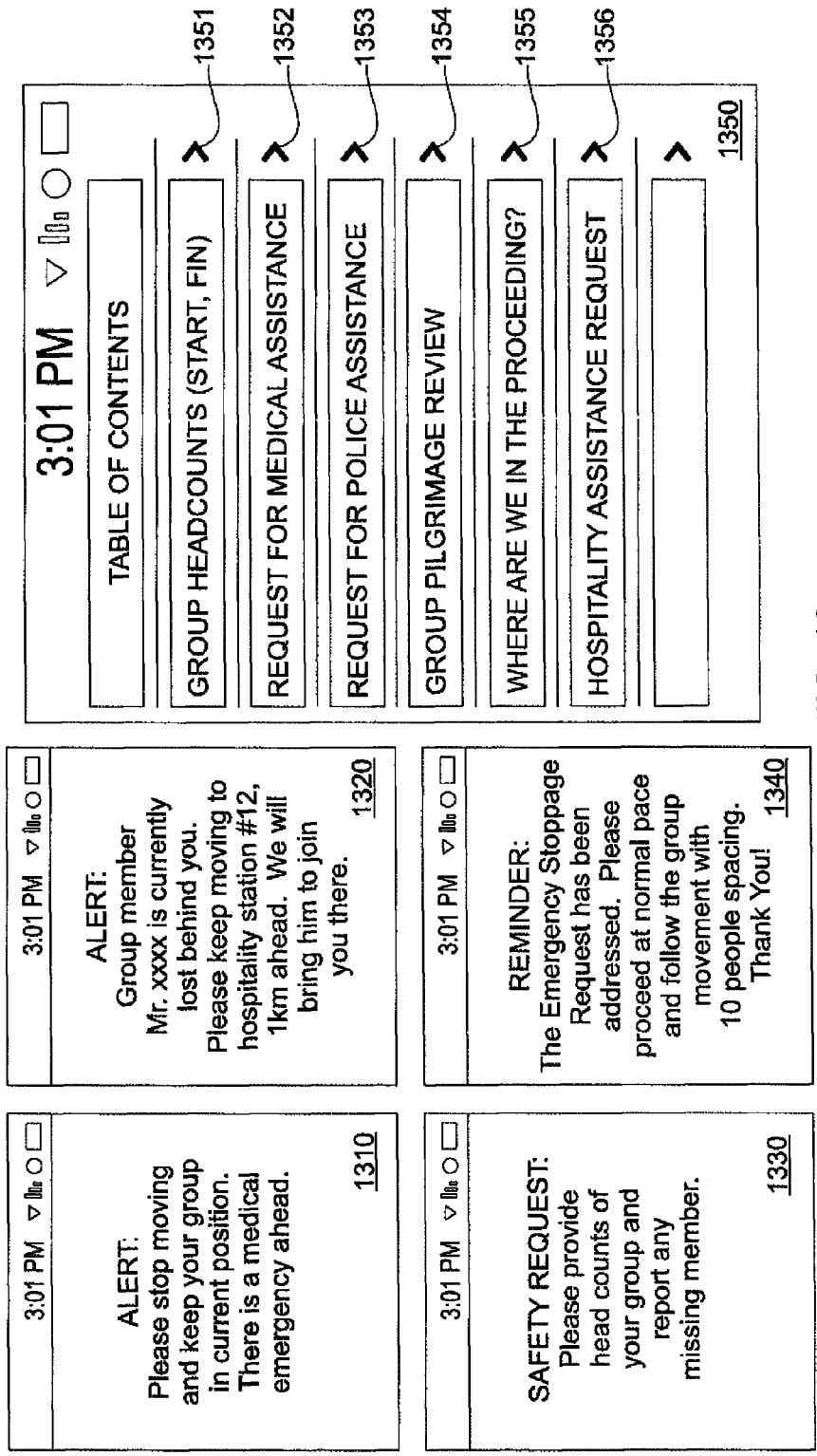
FIG. 13 is a schematic diagram illustrating example screen displays that may be provided by the present system and method.
Figure 14:
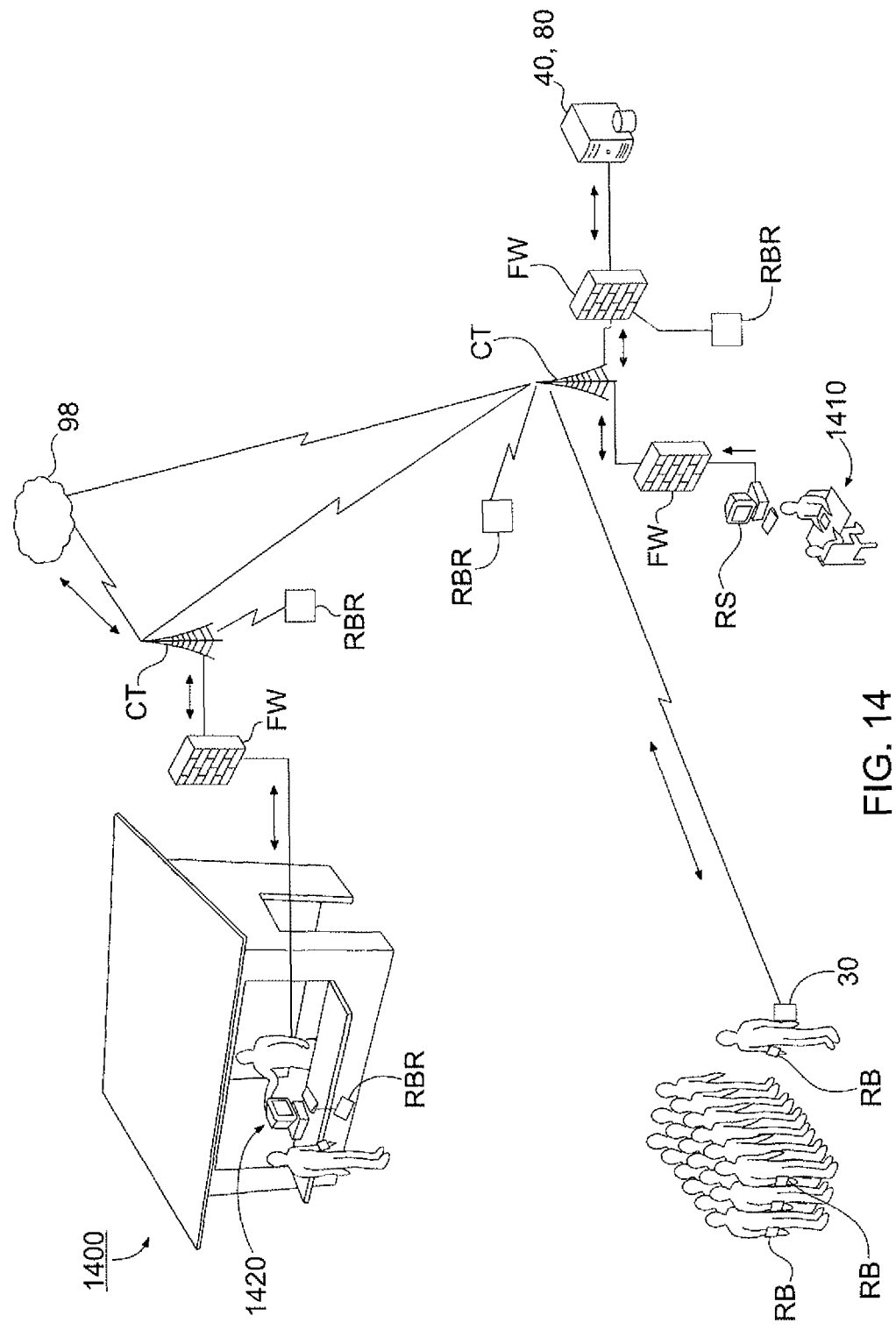
FIG. 14 is a schematic diagram of an application of the example system and method for a pilgrimage or other large gathering.

In addition, system 10 and method 10 may be employed in mass pilgrimages, and the like, where large numbers of people are involved that create potential need for locating particular persons and/or groups of persons, reuniting a lost person with a family or group, for providing directions and/or other instructions, for providing medical and other assistance, and the like. FIG. 13 is a schematic diagram illustrating example screen displays 1300 that may be provided by the present system and method 10, e.g., on the display of a smart phone 30 or other electronic device 30 as for a large event, and FIG. 14 is a schematic diagram of an application 1400 of the example system and method 10 for a pilgrimage or other large gathering.

In the present arrangement, one or more biometric identifiers, e.g., preferably fingerprint, but also facial images and/or facial recognition, obtained at registration 1410, may be employed for identifying individual persons and that identifying data is associated with a unique identifier, e.g., a unique identifier associated with a smart phone or other electronic device 30 that may be issued to or likely more commonly is already possessed by a person in the individual's family or group.

Registration 1410 upon arrival at and/or entry to the site of the mass program or pilgrimage includes issuing an electronic device 30 that has an installed software application ("app") as described above for capturing data and interfacing, or downloading or otherwise installing on any personal device 30 that is to be employed the software app so as to be completely functional and usable in conjunction with system and method 10, 1400. The software app may include, generate, capture or otherwise receive a unique identifier, e.g., from a data entry form 210 or from a kiosk or other computer registration device RS or by random generation thereof.

Personal identifying data and demographic data may be captured from data entry forms, e.g., data entry forms 210, or from entering data via a data entry device, e.g., a keyboard, at computer registration stations RS, e.g., kiosks, and/or from verifiable identification documents, e.g., preferably government issued ID such as national ID cards, driver's licenses, passports and the like. All such data is associated with a unique identifier, e.g., from a form 210 and/or from an electronic device 30, and once captured and communicated to a central data center location 40-80, may be verified against known data, e.g., data stored in one or more government databases relating to such documents.

Examples of tasks and/or actions 1310-1340 that can be automatically generated and communicated to ("pushed" out to) electronic devices 30 may include, e.g., alerts 1310 regarding present or dangerous conditions nearby or ahead, alerts 1320 regarding lost or separated group members and instructions as to where and when to find such person, safety checks 1330, requests and/or reminders 1340 regarding the presence and/or absence of any group members and/or instructions 1340 regarding where and when to proceed or otherwise participate, and other messages that may be necessary or advisable in the situation.

In addition, the software app also may provide one or more tools 1350 for assisting persons participating in the event or program, preferably in a form similar to that of a web site or a software help function. In one example, a Table of Contents 1350 or other entry screen display is provided through which various other functions and/or information sources may be accessed, e.g., by touching touch screen display 32 in the location of the icon or box therefor. Examples thereof may include, e.g., information relating to their registered family and/or group 1351, relating to where to find assistance 1352-1353, e.g., medical assistance 1352, police and security personnel 1353, relating to reviews and programs for the complete event 1354 or parts thereof, relating to orientation information 1355, e.g., such as where the family or group is in relation to geographic location and/or the program or event, relating to requesting various kinds of assistance, 1352, 1353, 1356, e.g., hospitality assistance 1356, and the like.

Additionally, and optionally, where very large groups of people, e.g., hundreds of thousands or millions of people, are expected to be present in relatively small venues or other locations, or to travel (e.g., walk) over various walks and/or paths, and/or to congregate in one or more central locations, e.g., as in Presidential inauguration or other large gathering on the grounds of the U.S. Capitol building and National Mall in Washington, D.C., or in the Hajj pilgrimage in Mecca, it is seen to be advantageous to utilize a common electronic device 30 for each family or group and to issue RFID wristbands RB or other RFID tags RB to each person in a family or group. Wrist bands, other bands and RFID tags are preferably of a type that is "tamper-evident" in that any attempt to remove or otherwise alter the device will be readily evident, e.g., upon visual inspection and/or by it becoming misfunctional or non-functional.

In this situation, registration 1410 of participants includes acquiring data as to the person and his identity, e.g., capturing identity data such as from a driver's license, national ID and/or passport, and capturing biometric data such as a facial image and/or fingerprint. The personal identifying data is related with the unique identifier of the RFID tags or bands RB issued to that person and are captured in the central relational database 40-80; this personal data for all members of a family or group and the unique RFID tag identifier are related to the unique identifier of the electronic device 30 that is registered to that family or group, likely a smart phone 30 belonging to one member thereof. Thus each individual family or group member is associated with a family or group and each group is registered 1410 by means including a smart phone or other electronic device 30, whereby every individual may be located for receiving assistance and/or being reunited with his family or group, while a more manageable number of electronic devices 30 are employed.

Various RFID readers RBR are provided at various locations within the area or venue so that the locations of RFID tags RB may be acquired as persons pass near to the RFID readers RBR and communicated to the central facility 50-80 to be stored in the relational database for being monitored. Long range RFID readers, e.g., under ISO18000-6C, which have a substantial reading range, e.g., about 10 feet (about 3.3 m) may be provided to cover walk ways and road ways, and/or portions of larger areas, while short range RFID readers, e.g., under ISO14443, which have a range of about 5 cm (about 2 inches), may be employed for secure wallet and access control. Where longer range is desired, e.g., beyond the typical range of about 2 feet to 20 feet (about 0.6 meter to 6.1 meters) of passive RFID devices, active RFID devices which may have a range of about 20-2000 feet (about 6.1-610 meters) may be employed, with compatible RFID readers.

Preferably, kiosks or other computerized access points 1420 are provided at locations throughout the venue and/or event so that persons being registered only by an RFID device RB (as well s persons registered by an electronic device 30) may use the kiosk 1420 to seek directions and/or other assistance, e.g., in locating and re-joining his family or group or in finding a particular location or service. Preferably each kiosk or access point 1420 has functionality similar to that described in relation to electronic devices 30, e.g., an assistance function 1350, as well as an RFID reader RBR so that a person using the kiosk or access point 1420 is automatically detected and identified, thereby to make obtaining directions and/or assistance easier, as would be necessary for a young child. An access point 1420 may or may not have a person thereat to provide assistance.

As reports of lost or separated persons are made, e.g., via a kiosk 1420 or smart device 30, data therefor is automatically communicated to the central computer database 40-80 which then monitors locations of RFID devices RB as reported by RFID readers RBR to identify the person reported missing, and to generate follow up notifications, e.g., "push" notifications, to the smart phone 30 for the lost person's family or group, thereby to quickly and efficiently assist in reuniting individuals with their family or group members.

Communication between and among registration station 1410, registration device RS, kiosks and access points 1420, RFID readers RBR, and central data center may be by cable, optical fiber and/or wireless link, e.g., an Internet protocol (IP) link, and each preferably includes a firewall FW for data security. Wireless communication may include various communication towers CT, microwave or other radio links and/or Internet links, as may be desirable in any given situation and location, and may include SMS texts, voice, data, and/or GPRS data transmissions. RFID wrist bands and/or other RFID devices RB may have a barcode thereon for providing another or a related unique identifier that is also captured upon registration 1410 and that may be read by a barcode scanner RBR which may be part of and/or separate from RFID reader RBR. Communication, particularly of data, and especially wireless and Internet communication, is preferably hashed and/or encrypted for privacy and security.

Examples of suitable relational databases include an SQL Server relational database available from Microsoft Corporation, an ASP.Net relational database available from Microsoft Corporation, or an Oracle Database 12c or MySQL relational databases available from Oracle Corporation, among other available databases. Other examples of software suitable for use with the foregoing may include, for example, the IBM "DB2" database software, and the Microsoft ".NET" (Dot-NET) software framework which can facilitate communication between various users and the computers of system 10 and can run with the Microsoft Server-2000 server software, and other database and Internet software that is available from Microsoft Corp., Oracle Corp., Sybase Corp., IBM Corp., and other sources. Various other suitable software is available from different sources known to those of ordinary skill in the art, e.g., for data capture, databases, data retrieval, networking, Internet interfacing, ad hoc networking and the like.

Fingerprint scanners and devices are preferably US FBI FIPS compliant devices FP that are compatible with commonly available electronic devices 30, e.g., smart phones such as ANDROID® or APPLE® operating system smart phones. Biometric fingerprint data produced by such fingerprint scanners is in format compatible for being verified by law enforcement and other government agencies, e.g., against government fingerprint databases, quickly and essentially in real time.

A method 10 for operating a registration and management system 10 may comprise: configuring 610, 705 an electronic device 30 having a device identifier and including an imager for capturing images and a geographic position locator for determining geographic location, the configuring 610, 705 including configuring 610, 705 the electronic device 30 for geo-tagging the captured images using the determined geographic location, for date-time stamping the geo-tagged captured images, and for receiving a unique identifier; causing 620 the date-time stamped geo-tagged captured images to be associated with the unique identifier; receiving 725 registration data relating to a registrant; associating 620 the unique identifier with the received registration data relating to a registrant; storing 70, 80, 170, 745 data including the unique identifier, the date-time stamped geo-tagged captured images associated with the unique identifier, the received registration data relating to a registrant associated with the unique identifier, and the device identifier of the electronic device 30, in a relational data base that is separate from the electronic device 30; repeating the foregoing steps for a number of registrants; retrieving 750, 765 from the relational database 40, 70, 80 stored data relating to a particular registrant using the unique identifier, or using a location of a geo-tagged captured image, or using the received registration data relating to the particular registrant, or using the device identifier, or using a combination thereof; generating 750 from the retrieved data from the relational database 40, 70, 80 relating to the particular registrant a response relating to the particular registrant; and communicating 48, 765 the response relating to the particular registrant to the electronic device 30 that captured data relating to the particular registrant using the device identifier of the electronic device 30 that captured the data relating to the particular registrant. The configuring 610, 705 may include providing a software application to the electronic device 30. Receiving the unique identifier may include imaging a barcode of a data entry form using the imager of the electronic device 30; and receiving registration data relating to a registrant may include scanning the data entry form. The unique identifier may be generated automatically and/or may be manually entered; or the unique identifier may be random or pseudo-random and/or taken from one or more sequences of numbers; or a combination thereof. The geographic location may include GPS coordinates and wherein the GPS coordinates are associated with captured images for geo-tagging the images. The configuring 610, 705 may include: configuring 610, 705 the electronic device 30 for capturing a biometric identifier; or configuring 610, 705 the electronic device 30 with one or more external devices for capturing a biometric identifier; or a combination thereof. The biometric identifier may include a fingerprint, a facial image, a digital signature, or a combination thereof, or the biometric identifier may be utilized for identification and/or for verification of identity; or the biometric identifier may include a fingerprint, a facial image, a digital signature, or a combination thereof, and may be utilized for identification and/or for verification of identity. The method for operating a registration and management system 10 may further comprise: associating an RFID device RB with a participant; associating the RFID device RB with an electronic device 30 relating to the participant and with the electronic device identifier thereof; storing an identifier of the RFID device RB and data relating to the participant in the relational database 40, 70, 80 in association with the device identifier of the electronic device 30 relating to the participant; providing one or more RFID readers RBR for locating the RFID device RB; and storing RFID device RB locating data from the one or more RFID readers RBR in the relational database 40, 70, 80, whereby the participant RFID device RB may be associated with the electronic device 30 relating to the participant. The registrant may include: a person, a family, a group of persons, a location, a structure, a natural feature, a tangible article, a movable tangible article, a container, a package, or a combination thereof. The method for operating a registration and management system 10 may further comprise employing the registration and management system 10 for conducting a census, for a vaccination program, for an emergency, for a natural disaster, for a man-made disaster, for property management, for geo-routing, for geo-fencing, for a supply chain, or for a combination thereof. The electronic device 30 may include a smart phone, a tablet computer, a portable computer, or a combination thereof.

A registration and management system 10 may comprise: an electronic device 30 having a device identifier and including an imager for capturing images and a geographic position locator for determining geographic location, the electronic device 30 being configured for geo-tagging the captured images using the determined geographic location, for date-time stamping the geo-tagged captured images, and for receiving a unique identifier; a computer processor 40, 70, 80 receiving date-time stamped geo-tagged captured images associated with the unique identifier, registration data relating to a registrant, and associating the unique identifier with the received registration data relating to a registrant; a relational database 40, 70, 80 storing data including the unique identifier, the date-time stamped geo-tagged captured images associated with the unique identifier, the received registration data relating to a registrant associated with the unique identifier, and the device identifier of the electronic device 30, wherein the relational data base may be separate from the electronic device 30; wherein the foregoing is repeated for a number of registrants; the computer processor 40, 70, 80 retrieving from the relational database 40, 70, 80 stored data relating to a particular registrant using the unique identifier, or using a location of a geo-tagged captured image, or using the received registration data relating to the particular registrant, or using the device identifier, or using a combination thereof; the computer processor 40, 70, 80 generating from the retrieved data from the relational database 40, 70, 80 relating to the particular registrant a response relating to the particular registrant; and a communication link 36, 38, 98, 400 communicating the response relating to the particular registrant to the electronic device 30 that captured data relating to the particular registrant using the device identifier of the electronic device 30 that captured the data relating to the particular registrant. The electronic device 30 may be configured by a software application. The unique identifier may be obtained by imaging a barcode of a data entry form 210 using the imager of the electronic device 30; and the registration data relating to a registrant may be obtained by scanning the data entry form. The unique identifier may be generated automatically and/or may be manually entered; or the unique identifier may be random or pseudo-random and/or taken from one or more sequences of numbers; or a combination thereof. The geographic location may include GPS coordinates and wherein the GPS coordinates are associated with captured images for geo-tagging the images. The electronic device 30 may be configured for capturing a biometric identifier; or the electronic device 30 may be configured with one or more external devices for capturing a biometric identifier; or a combination thereof. The biometric identifier may include a fingerprint, a facial image, a digital signature, or a combination thereof, or the biometric identifier may be utilized for identification and/or for verification of identity; or the biometric identifier may include a fingerprint, a facial image, a digital signature, or a combination thereof, and may be utilized for identification and/or for verification of identity. The registration and management system 10 may further comprise: an RFID device RB associated with a participant; the RFID device RB being associated with an electronic device 30 relating to the participant and with the electronic device identifier thereof; the relational database 40, 70, 80 storing an identifier of the RFID device RB and data relating to the participant in association with the device identifier of the electronic device 30 relating to the participant; one or more RFID readers RBR for locating the RFID device RB; and the relational database 40, 70, 80 storing RFID device RB locating data from the one or more RFID readers RBR, whereby the participant RFID device RB may be associated with the electronic device 30 relating to the participant. The registrant may include: a person, a family, a group of persons, a location, a structure, a natural feature, a tangible article, a movable tangible article, a container, a package, or a combination thereof. The registration and management system 10 may be employed for conducting a census, for a vaccination program, for an emergency, for a natural disaster, for a man-made disaster, for property management, for geo-routing, for geo-fencing, for a supply chain, or for a combination thereof. The electronic device 30 may include a smart phone, a tablet computer, a portable computer, or a combination thereof.

A method 10 for operating a registration and management system 10 may comprise: configuring 610, 705 an electronic device 30 having a device identifier and including an imager for capturing images and a geographic position locator for determining geographic location, the configuring 610, 705 including configuring 610, 705 the electronic device 30 for capturing a biometric identifier relating to a registrant, for geo-tagging the captured images using the determined geographic location, for geo-tagging the captured biometric identifier using the determined geographic location, for date-time stamping the geo-tagged captured images and the geo-tagged captured biometric identifier, and for receiving a unique identifier; causing 620 the date-time stamped geo-tagged captured images and date-time stamped geo-tagged captured biometric identifier to be associated with the unique identifier; receiving 620, 725 registration data relating to the registrant; associating 620 the unique identifier with the received registration data relating to the registrant; storing 70, 80, 170, 745 data including the unique identifier, the date-time stamped geo-tagged captured images associated with the unique identifier, the date-time stamped geo-tagged captured biometric identifier associated with the unique identifier, the received registration data relating to the registrant associated with the unique identifier, and the device identifier of the electronic device 30, in a relational data base that is separate from the electronic device 30; repeating the foregoing steps for a number of registrants; retrieving 750, 765 from the relational database 40, 70, 80 stored data relating to a particular registrant using the unique identifier, or using a location of a geo-tagged captured image, or using the captured biometric identifier relating to the particular registrant, or using the received registration data relating to the particular registrant, or using the device identifier, or using a combination thereof; generating 750 from the retrieved data from the relational database 40, 70, 80 relating to the particular registrant a response relating to the particular registrant; and communicating 48, 765 the response relating to the particular registrant to the electronic device 30 that captured data relating to the particular registrant using the device identifier of the electronic device 30 that captured the data relating to the particular registrant. Receiving the unique identifier may include imaging a barcode of a data entry form using the imager of the electronic device 30; and receiving registration data relating to a registrant may include scanning the data entry form. The biometric identifier may include a fingerprint, a facial image, a digital signature, or a combination thereof, or the biometric identifier may be utilized for identification and/or for verification of identity; or the biometric identifier may include a fingerprint, a facial image, a digital signature, or a combination thereof, and may be utilized for identification and/or for verification of identity.

A method 10 for operating a registration and management system 10 for a mass gathering event may comprise: configuring 610, 750 an electronic device 30 having a device identifier and including a device for capturing data selected from the group including an imager, a touch screen, a keyboard, or a combination thereof, including a communication device selected from the group including wireless communication, Bluetooth communication, WiFi communication, cellular communication, satellite telephony communication, and a combination thereof, and including a geographic position locator for determining geographic location, the configuring including configuring 610, 705 the electronic device 30 for geo-tagging captured data using the determined geographic location, for date-time stamping the geo-tagged captured data, and for receiving a unique identifier; receiving or providing 620, 725 a unique identifier associated with a group of registrants and a mass gathering event; causing the date-time stamped geo-tagged captured data to be associated 620 with the unique identifier; receiving 620, 705 registration data relating to the group of registrants; associating 620 the unique identifier with the received registration data relating to the group of registrants; storing 70, 80, 170, 745 data including the unique identifier, the date-time stamped geo-tagged captured data associated with the unique identifier, the received registration data relating to the group of registrants associated with the unique identifier, and the device identifier of the electronic device 30, in a relational data base that is separate from the electronic device 30; repeating the foregoing steps for a number of groups of registrants; retrieving 750, 765 from the relational database 40, 70, 80 stored data relating to a particular group of registrants using the unique identifier, or using a location of geo-tagged captured data, or using the received registration data relating to the particular group of registrants, or using the device identifier, or using a combination thereof; generating 750 from the retrieved data from the relational database 40, 70, 80 relating to the particular group of registrants a response relating to the particular group of registrants, wherein the response comprises a task to be performed, or an action to be taken, or a supply to be provided, or equipment to be provided, or a schedule for performing a task, or a schedule for taking an action, or a report of a task and/or an action, or a combination thereof; and communicating 48, 765 the response relating to the particular group of registrants to the electronic device 30 that captured data relating to the particular group of registrants using the device identifier of the electronic device 30 that captured the data relating to the particular group of registrants or to an electronic device 30 using the geographic location thereof, or to both. The configuring 610, 705 may include providing a software application to the electronic device 30. The receiving 620, 725 the unique identifier may include imaging a barcode of a data entry form using the imager of the electronic device 30; and receiving 620, 725 registration data relating to a group of registrants may include scanning the data entry form. The unique identifier may be generated automatically and/or may be manually entered; or the unique identifier may be random or pseudo-random and/or may be taken from one or more sequences of numbers; or a combination thereof. The geographic location may include GPS coordinates and wherein the GPS coordinates may be associated with captured data for geo-tagging the data. The configuring 610, 705 may include: configuring 610, 705 the electronic device 30 for capturing a biometric identifier; or configuring 610, 705 the electronic device 30 with one or more external devices for capturing a biometric identifier; or a combination thereof. The biometric identifier may include a fingerprint, a facial image, a digital signature, or a combination thereof, or the biometric identifier may be utilized for identification and/or for verification of identity; or the biometric identifier may include a fingerprint, a facial image, a digital signature, or a combination thereof, and may be utilized for identification and/or for verification of identity. The method 10 for operating a registration and management system 10 may further comprise: associating 620 an RFID device RB with at least one participant of the group of registrants; associating 620 the RFID device RB with the electronic device 30 relating to that group of registrants and with the electronic device 30 identifier thereof; storing 70, 80, 170, 745 an identifier of the RFID device RB and data relating to the at least one participant in the relational database 40, 70, 80 in association with the device identifier of the electronic device 30 relating to that group of registrants; whereby the participant RFID device RB is associated with the electronic device 30 relating to the group of registrants with which the at least one participant is associated. The configuring 610, 705 an electronic device 30 may include configuring 610, 705 the electronic device 30 for communication with an RFID device RB. The method 10 for operating a registration and management system 10 may further comprise: providing one or more RFID readers RBR for locating RFID devices RB; and storing 70, 80, 170, 745 RFID device RB locating data from the one or more RFID readers RBR in the relational database 40, 70, 80. The RFID device RB may include a wristband, or a tamper-evident wristband, or a combination thereof. The group of registrants may include: a person, a family, a group of persons, tangible articles, movable tangible articles, or a combination thereof. The electronic device 30 may include a smart phone, a tablet computer, a portable computer, or a combination thereof. The generated response may include: an alert, a safety check, a warning, a request, a reminder, an instruction, a report, a report of a participant who may be separated from the group of registrants, a report of a participant who may be lost, a follow up notification, information relating to the group of registrants, information relating to available assistance, information relating to reviews and/or programs, orientation information, information relating to hospitality assistance, information relating to medical assistance, information relating to police or security assistance, information relating to geographical location, or any combination thereof. The electronic device 30 may be employed to communicate a request to the relational data base, and wherein the generated response relates to the request and may be communicated to the electronic device 30 that communicated the request. The request communicated by the electronic device 30 may relate to medical assistance, police assistance, security assistance, location assistance, assistance relating to a participant in the group of registrants associated with that electronic device 30, assistance relating to a participant who may be separated from the group of registrants associated with that electronic device 30, or any combination thereof. The communicating 48, 765 the response may include communicating 48, 765 an instruction to plural electronic device 30s relating to their respective geographic locations. The communicating 48, 765 the response may include communicating 48, 765 an instruction to move, an instruction to not move, an instruction relating to a geographic location, a report, a notification, a warning, or a combination thereof.

A registration and management system 10 for a mass gathering event may comprise: an electronic device 30 having a device identifier and including a device for capturing data selected from the group including an imager, a touch screen, a keyboard, or a combination thereof, including a communication device selected from the group including wireless communication, Bluetooth communication, WiFi communication, cellular communication, satellite telephony communication, and a combination thereof, and including a geographic position locator for determining geographic location, the electronic device 30 being configured 610, 765 for geo-tagging the captured data using the determined geographic location, for date-time stamping the geo-tagged captured data, and for receiving 620, 725 a unique identifier; a computer processor 40, 70, 80 receiving or providing a unique identifier relating to a group of registrants and a mass gathering event, date-time stamped geo-tagged captured data associated with the unique identifier, registration data relating to the group of registrants, and associating the unique identifier with the received registration data relating to the group of registrants; a relational database 40, 70, 80 storing data including the unique identifier, the date-time stamped geo-tagged captured data associated with the unique identifier, the received registration data relating to the group of registrants associated with the unique identifier, and the device identifier of the electronic device 30, wherein the relational data base is separate from the electronic device 30; wherein the foregoing is repeated for a number of groups of registrants; the computer processor 40, 70, 80 retrieving from the relational database 40, 70, 80 stored data relating to a particular group of registrants using the unique identifier, or using a location of geo-tagged captured data, or using the received registration data relating to the particular group of registrants, or using the device identifier, or using a combination thereof; the computer processor 40, 70, 80 generating 750 from the retrieved data from the relational database 40, 70, 80 relating to the particular group of registrants a response relating to the particular group of registrants, wherein the response comprises a task to be performed, or an action to be taken, or a supply to be provided, or equipment to be provided, or a schedule for performing a task, or a schedule for taking an action, or a report of a task and/or an action, or a combination thereof; and a communication link 36, 38, 98, 400 communicating the response relating to the particular group of registrants and mass gathering event to the electronic device 30 that captured data relating to the particular group of registrants using the device identifier of the electronic device 30 that captured the data relating to the particular group of registrants or to an electronic device 30 using the geographic location thereof, or to both. The electronic device 30 is configured 610, 705 by a software application. The unique identifier may be obtained by imaging a barcode of a data entry form using the imager of the electronic device 30; and the registration data relating to a group of registrants may be obtained by scanning the data entry form. The unique identifier may be generated automatically and/or may be manually entered; or the unique identifier may be random or pseudo-random and/or may be taken from one or more sequences of numbers; or a combination thereof. The geographic location may include GPS coordinates and wherein the GPS coordinates are associated with captured data for geo-tagging the images. The electronic device 30 may be configured 610, 705 for capturing a biometric identifier; or the electronic device 30 may be configured 610, 705 with one or more external devices for capturing a biometric identifier; or a combination thereof. The biometric identifier may include a fingerprint, a facial image, a digital signature, or a combination thereof, or the biometric identifier may be utilized for identification and/or for verification of identity; or the biometric identifier may include a fingerprint, a facial image, a digital signature, or a combination thereof, and may be utilized for identification and/or for verification of identity. The registration and management system 10 may further comprise: an RFID device RB associated with at least one participant of the group of registrants; the RFID device RB being associated with the electronic device 30 relating to that group of registrants and with the electronic device 30 identifier thereof; wherein an identifier of the RFID device RB and data relating to the at least one participant is stored in the relational database 40, 70, 80 in association with the device identifier of the electronic device 30 relating to that group of registrants; whereby the participant RFID device RB is associated with the electronic device 30 relating to the group of registrants with which the at least one participant is associated. The electronic device 30 may be configured 610, 705 for communication with an RFID device RB. The registration and management system 10 may further comprise: one or more RFID readers RBR for locating RFID devices RB, wherein RFID device RB locating data from the one or more RFID readers RBR may be stored in the relational database 40, 70, 80. The RFID device RB may include a wristband or a tamper-evident wristband, or a combination thereof. The group of registrants may include: a person, a family, a group of persons, tangible articles, movable tangible articles, or a combination thereof. The electronic device 30 may include a smart phone, a tablet computer, a portable computer, or a combination thereof. The generated response may include: an alert, a safety check, a warning, a request, a reminder, an instruction, a report, a report of a participant who may be separated from the group of registrants, a report of a participant who may be lost, a follow up notification, information relating to the group of registrants, information relating to available assistance, information relating to reviews and/or programs, orientation information, information relating to hospitality assistance, information relating to medical assistance, information relating to police or security assistance, information relating to geographical location, or any combination thereof. The electronic device 30 may be employed to communicate a request to the relational data base, and wherein the generated response relates to the request and may be communicated to the electronic device 30 that communicated the request. The request communicated by the electronic device 30 may relate to medical assistance, police assistance, security assistance, location assistance, assistance relating to a participant in the group of registrants associated with that electronic device 30, assistance relating to a participant who may be separated from the group of registrants associated with that electronic device 30, or any combination thereof. The response may communicate an instruction to plural electronic device 30s relating to their respective geographic locations. The response may communicate 48, 765 an instruction to move, an instruction to not move, an instruction relating to a geographic location, a report, a notification, a warning, or a combination thereof.

As used herein, the term "about" means that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

It is noted that while data acquired and/or stored, e.g., in a database, may be referred to as "numbers," each may include numerical, alphabetic, alpha-numeric and other characters and symbols, conventional or arbitrary, as may be desired. Information is typically represented and/or stored in a memory in accordance with a predetermined formula or algorithm or other scheme, either on a character by character basis or on the basis of one or more combinations of the characters or values, for example, binary, binary coded decimal, hexadecimal, or any other digital coding representation thereof. A parity or check number or code, if any, may likewise be representative of the information represented or stored in accordance with a predetermined formula or algorithm or other scheme, either on a character by character basis or on the basis of one or more combinations of the characters or values stored. Suitable formula and algorithms therefor include, for example, binary, binary coded decimal, other digital coding representations thereof, parity checks or other parity representations, sum checks, field relationship checks or any other predetermined relationship between the stored data or information and the parity or check number or code.

The present arrangement can be and preferably is at least in part embodied as a computer implemented process or processes and/or apparatus for performing such computer-implemented process or processes, and can also be embodied in the form of a tangible storage medium containing a computer program or other machine-readable instructions (herein "computer program"), wherein when the computer program is loaded into a computer or other processor (herein "computer") and/or is executed by the computer, the computer becomes an apparatus for practicing the process or processes. Storage media for containing such computer program include, for example, floppy disks and diskettes, compact disk (CD)-ROMs (whether or not writeable), DVD digital disks, RAM and ROM memories, computer hard drives and back-up drives, external hard drives, "thumb" drives, and any other storage medium readable by a computer. The process or processes can also be embodied in the form of a computer program, for example, whether stored in a storage medium or transmitted over a transmission medium such as electrical conductors, fiber optics or other light conductors, or by electromagnetic radiation, wherein when the computer program is loaded into a computer and/or is executed by the computer, the computer becomes an apparatus for practicing the process or processes. The process or processes may be implemented on a general purpose microprocessor or on a digital processor specifically configured to practice the process or processes. When a general-purpose microprocessor is employed, the computer program code configures the circuitry of the microprocessor to create specific logic circuit arrangements. Storage medium readable by a computer includes medium being readable by a computer per se or by another machine that reads the computer instructions for providing those instructions to a computer for controlling its operation. Such machines may include, for example, a punched card reader, a magnetic tape reader, a magnetic card reader, a memory card reader, an optical scanner, as well as machines for reading the storage media mentioned above.

It is noted that various data, images, sensor values and other values may represent actual physical conditions of different places and/or different equipment and/or different parts of an installation, article, vessel and/or other place, e.g., generally local conditions, that may be transformed by the system and method described herein to provide a representation of the overall state and/or condition of the installation, article, vessel and/or place, e.g. a representation of the complete installation, vessel, article and/or place. That representation may be transformative of a representation of a nominal overall state and/or condition thereof, e.g., in a prior or different condition and/or time, to a representation of an actual overall state and/or condition thereof, e.g., in a present or more recent or otherwise different condition and/or time. Further, the system and method may generate tasks and commands that are executed to transform the installation, vessel, article and/or place into a different configuration, i.e. into a different installation, vessel, article and/or place, and a representation of that different configuration is provided or displayed, e.g., to human operators. The system described herein may include one or more general purpose and/or special purpose computers, or microprocessors or other processors, and the method described herein may be performed in part by one or more general purpose and/or special purpose computers, or microprocessors or other processors.

As used herein, image and/or information may be used interchangeably with respect to what is captured by an imaging device and/or displayed on a display device, and are intended to encompass any and all of the wide variety of devices that a user may desire, including, but not limited to, visual images and pictures, whether still or moving, whether captured and/or generated by a camera, computer or any other source, whether true, representative or abstract or arbitrary, whether or not including symbols or characters such as alphanumeric characters or mathematical notations, whether captured and/or displayed in black and white, monochrome, polychrome or full color.

While the present invention has been described in terms of the foregoing example embodiments, variations within the scope and spirit of the present invention as defined by the claims following will be apparent to those skilled in the art. For example, electronic devices 30 may be available smart phones as described or may be custom electronic devices that include the functionality as described. Thus all or part of the internal circuit board from a smart phone, and possibly its touch screen display may be employed as the main component of such device 30, with, e.g., a fingerprint scanner and web-cam being added thereto, and the electronic circuitry then being packaged into a convenient housing.

The unique identifier, which may be captured from a barcode or other tangible representation, may be generated automatically, e.g., in the production of data entry forms 210 or by the configuring software application for electronic devices 30 of by a computer at a data center, or may be manually entered, e.g., on a data entry form 210 or via an electronic device 30. Further, the unique identifiers may be random or pseudo-random, e.g., as generated by computer or by an electronic device 30 or by another pseudo-random number generator, or may be taken from one or more sequences of numbers, and in any instance some of the numbers may be designated to be representative of particular information, e.g., a political or other jurisdiction. A number may include numerical symbols, alphabetical symbols, other characters, and/or other symbols.

While example applications of the registration system and method 10 described herein are specifically set out as examples, the present system and method 10 as described and claimed is seen to be potentially applicable to a wide variety of other situations and applications.

In a property management application and/or a supply chain management application, and also in a disaster or relief response environment, articles registered (e.g., registrants) may include containers, packages, vehicles, rail cars, trucks, tractors, trailers, and the like. Registration thereof in the supply chain context may include capturing images of such articles, capturing images of barcodes or other unique identifiers marked on and/or associated with such articles, capturing images of the article and its location, capturing images and/or biometric identifiers of personnel, e.g., drivers, mechanics and other service personnel, whereby captured data by electronic devices 30 are communicated to the one or more data centers and stored in the one or more relational databases thereof, from whence they may be searched, accessed and utilized to generate reports and tasks and actions for follow up, as described.

In a property management application and/or a supply chain management application, RFID devices RB may be applied to items of property, including containers and/or packages therefor, and may include sensors for monitoring those items, e.g., environmental conditions, GPS location, and the like. In the case of physical items, e.g., files and other physical records, and containers, monitoring the opening and closing of containers in which such physical articles are disposed and their removal and transport, and the dates and times thereof. Captured images, e.g., of the locations at which the physical property is disposed can assist in locating the property and its location. In addition, captured images may be employed to identify particular items of property, e.g., works of art, jewelry, rare books, and the like.

In the case of written records, the captured images may include images of the actual records with sufficient resolution, e.g., at least 300 dpi or greater, so as to be readable and printable from the captured images, should that become desirable or necessary, e.g., as in a business recovery from a fire or other disaster. Alternatively and/or additionally, sheet records may be scanned to capture images thereof, with or without optical character recognition, to create electronic files that can be stored and accessed via the relational database of the present system and method 10.

In addition to RFID devices, e.g., in wrist bands and tags and/or on other physical property, a barcode may also be provided for further identifying the physical property. In such instance, barcode scanners may be provided to augment, complement and/or supplement RFID readers, whereby a mixed system of barcode and RFID identification may be employed.

Each of the U.S. Provisional Applications, U.S. Patent Applications, and/or U.S. Patents identified herein is hereby incorporated herein by reference in its entirety, for any purpose and for all purposes irrespective of how it may be referred to or described herein.

Finally, numerical values stated are typical or example values, are not limiting values, and do not preclude substantially larger and/or substantially smaller values. Values in any given embodiment may be substantially larger and/or may be substantially smaller than the example or typical values stated.

What is claimed is:

1. A method for operating a registration and management system for a mass gathering event comprising:
    configuring an electronic device having a device identifier and including a device for capturing data selected from the group including an imager, a touch screen, a keyboard, or a combination thereof, including a communication device selected from the group including wireless communication, Bluetooth communication, WiFi communication, cellular communication, satellite telephony communication, and a combination thereof, and including a geographic position locator for determining geographic location, the configuring including configuring the electronic device for geo-tagging captured data using the determined geographic location, for date-time stamping the geo-tagged captured data, and for receiving a unique identifier;

receiving or providing a unique identifier associated with a group of registrants and the mass gathering event;

causing the date-time stamped geo-tagged captured data to be associated with the unique identifier;

receiving registration data relating to the group of registrants;

associating the unique identifier with the received registration data relating to the group of registrants;

storing data including the unique identifier, the date-time stamped geo-tagged captured data associated with the unique identifier, the received registration data relating to the group of registrants associated with the unique identifier, and the device identifier of the electronic device, in a relational data base that is separate from the electronic device;

repeating the foregoing steps for a number of groups of registrants;

retrieving from the relational database stored data relating to a particular group of registrants using the unique identifier, or using a location of geo-tagged captured data, or using the received registration data relating to the particular group of registrants, or using the device identifier, or using a combination thereof;

generating from the retrieved data from the relational database relating to the particular group of registrants a response relating to the particular group of registrants, wherein the response comprises a task to be performed, or an action to be taken, or a supply to be provided, or equipment to be provided, or a schedule for performing a task, or a schedule for taking an action, or a report of a task and/or an action, or a combination thereof; and communicating the response relating to the particular group of registrants to the electronic device that captured data relating to the particular group of registrants using the device identifier of the electronic device that captured the data relating to the particular group of registrants or to an electronic device using the geographic location thereof, or to both.

2. The method for operating a registration and management system of claim 1 wherein said configuring includes providing a software application to the electronic device.

3. The method for operating a registration and management system of claim 1 wherein:
receiving the unique identifier includes imaging a barcode of a data entry form using the imager of the electronic device; and
receiving registration data relating to a group of registrants includes scanning the data entry form.

4. The method for operating a registration and management system of claim 1 wherein
the unique identifier is generated automatically and/or is manually entered; or
the unique identifier is random or pseudo-random and/or is taken from one or more sequences of numbers; or
a combination thereof.

5. The method for operating a registration and management system of claim 1 wherein the geographic location includes GPS coordinates and wherein the GPS coordinates are associated with captured data for geo-tagging the data.

6. The method for operating a registration and management system of claim 1 wherein the configuring includes:
configuring the electronic device for capturing a biometric identifier; or
configuring the electronic device with one or more external devices for capturing a biometric identifier; or
a combination thereof.

7. The method for operating a registration and management system of claim 6 wherein:
the biometric identifier includes a fingerprint, a facial image, a digital signature, or a combination thereof, or
the biometric identifier is utilized for identification and/or for verification of identity; or
the biometric identifier includes a fingerprint, a facial image, a digital signature, or a combination thereof, and is utilized for identification and/or for verification of identity.

8. The method for operating a registration and management system of claim 1 further comprising:
associating an RFID device with at least one participant of the group of registrants;
associating the RFID device with the electronic device relating to that group of registrants and with the electronic device identifier thereof;
storing an identifier of the RFID device and data relating to the at least one participant in the relational database in association with the device identifier of the electronic device relating to that group of registrants;
whereby the participant RFID device is associated with the electronic device relating to the group of registrants with which the at least one participant is associated.

9. The method for operating a registration and management system of claim 8 wherein:
configuring an electronic device includes configuring the electronic device for communication with an RFID device.

10. The method for operating a registration and management system of claim 8 further comprising:
providing one or more RFID readers for locating RFID devices; and
storing RFID device locating data from the one or more RFID readers in the relational database.

11. The method for operating a registration and management system of claim 8 wherein the RFID device includes a wristband, or a tamper-evident wristband, or a combination thereof.

12. The method for operating a registration and management system of claim 1 wherein the group of registrants includes: a person, a family, a group of persons, tangible articles, movable tangible articles, or a combination thereof.

13. The method for operating a registration and management system of claim 1 wherein the electronic device includes a smart phone, a tablet computer, a portable computer, or a combination thereof.

14. The method for operating a registration and management system of claim 1 wherein the generated response includes: an alert, a safety check, a warning, a request, a reminder, an instruction, a report, a report of a participant who is separated from the group of registrants, a report of a participant who is lost, a follow up notification, information relating to the group of registrants, information relating to available assistance, information relating to reviews and/or programs, orientation information, information relating to hospitality assistance, information relating to medical assistance, information relating to police or security assistance, information relating to geographical location, or any combination thereof.

15. The method for operating a registration and management system of claim 1 wherein the electronic device is employed to communicate a request to the relational data base, and wherein the generated response relates to the request and is communicated to the electronic device that communicated the request.

16. The method for operating a registration and management system of claim 15 wherein the request communicated by the electronic device relates to medical assistance, police assistance, security assistance, location assistance, assistance relating to a participant in the group of registrants associated with that electronic device, assistance relating to a participant who is separated from the group of registrants associated with that electronic device, or any combination thereof.

17. The method for operating a registration and management system of claim 1 wherein communicating the response includes communicating an instruction to plural electronic devices relating to their respective geographic locations.

18. The method for operating a registration and management system of claim 1 wherein communicating the response includes communicating an instruction to move, an instruction to not move, an instruction relating to a geographic location, a report, a notification, a warning, or a combination thereof.

19. A registration and management system for a mass gathering event comprising:
    an electronic device having a device identifier and including a device for capturing data selected from the group including an imager, a touch screen, a keyboard, or a combination thereof, including a communication device selected from the group including wireless communication, Bluetooth communication, WiFi communication, cellular communication, satellite telephony communication, and a combination thereof, and including a geographic position locator for determining geographic location, the electronic device being configured for geo-tagging the captured data using the determined geographic location, for date-time stamping the geo-tagged captured data, and for receiving a unique identifier;
    a computer processor receiving or providing a unique identifier relating to a group of registrants and the mass gathering event, date-time stamped geo-tagged captured data associated with the unique identifier, registration data relating to the group of registrants, and associating the unique identifier with the received registration data relating to the group of registrants;
    a relational database storing data including the unique identifier, the date-time stamped geo-tagged captured data associated with the unique identifier, the received registration data relating to the group of registrants associated with the unique identifier, and the device identifier of the electronic device, wherein the relational data base is separate from the electronic device;
    wherein the foregoing is repeated for a number of groups of registrants;
    the computer processor retrieving from the relational database stored data relating to a particular group of registrants using the unique identifier, or using a location of geo-tagged captured data, or using the received registration data relating to the particular group of registrants, or using the device identifier, or using a combination thereof;
    the computer processor generating from the retrieved data from the relational database relating to the particular group of registrants a response relating to the particular group of registrants, wherein the response comprises a task to be performed, or an action to be taken, or a supply to be provided, or equipment to be provided, or a schedule for performing a task, or a schedule for taking an action, or a report of a task and/or an action, or a combination thereof; and
    a communication link communicating the response relating to the particular group of registrants and the mass gathering event to the electronic device that captured data relating to the particular group of registrants using the device identifier of the electronic device that captured the data relating to the particular group of registrants or to an electronic device using the geographic location thereof, or to both.

20. The registration and management system of claim 19 wherein the electronic device is configured by a software application.

21. The registration and management system of claim 19 wherein:
    the unique identifier is obtained by imaging a barcode of a data entry form using the imager of the electronic device; and
    the registration data relating to a group of registrants is obtained by scanning the data entry form.

22. The registration and management system of claim 19 wherein
    the unique identifier is generated automatically and/or is manually entered; or
    the unique identifier is random or pseudo-random and/or is taken from one or more sequences of numbers; or
    a combination thereof.

23. The registration and management system of claim 19 wherein the geographic location includes GPS coordinates and wherein the GPS coordinates are associated with captured data for geo-tagging the images.

24. The registration and management system of claim 19 wherein:
    the electronic device is configured for capturing a biometric identifier; or
    the electronic device is configured with one or more external devices for capturing a biometric identifier; or
    a combination thereof.

25. The registration and management system of claim 19 wherein:
    the biometric identifier includes a fingerprint, a facial image, a digital signature, or a combination thereof, or
    the biometric identifier is utilized for identification and/or for verification of identity; or
    the biometric identifier includes a fingerprint, a facial image, a digital signature, or a combination thereof, and is utilized for identification and/or for verification of identity.

26. The registration and management system of claim 19 further comprising:
    an RFID device associated with at least one participant of the group of registrants;
    the RFID device being associated with the electronic device relating to that group of registrants and with the electronic device identifier thereof;
    wherein an identifier of the RFID device and data relating to the at least one participant is stored in the relational database in association with the device identifier of the electronic device relating to that group of registrants; whereby the participant RFID device is associated with the electronic device relating to the group of registrants with which the at least one participant is associated.

27. The registration and management system of claim 26 wherein:
the electronic device is configured for communication with an RFID device.

28. The registration and management system of claim 26 further comprising:
one or more RFID readers for locating RFID devices, wherein RFID device locating data from the one or more RFID readers is stored in the relational database.

29. The registration and management system of claim 26 wherein the RFID device includes a wristband or a tamper-evident wristband, or a combination thereof.

30. The registration and management system of claim 19 wherein the group of registrants includes: a person, a family, a group of persons, tangible articles, movable tangible articles, or a combination thereof.

31. The registration and management system of claim 19 wherein the electronic device includes a smart phone, a tablet computer, a portable computer, or a combination thereof.

32. The registration and management system of claim 19 wherein the generated response includes: an alert, a safety check, a warning, a request, a reminder, an instruction, a report, a report of a participant who is separated from the group of registrants, a report of a participant who is lost, a follow up notification, information relating to the group of registrants, information relating to available assistance, information relating to reviews and/or programs, orientation information, information relating to hospitality assistance, information relating to medical assistance, information relating to police or security assistance, information relating to geographical location, or any combination thereof.

33. The registration and management system of claim 19 wherein the electronic device is employed to communicate a request to the relational data base, and wherein the generated response relates to the request and is communicated to the electronic device that communicated the request.

34. The registration and management system of claim 33 wherein the request communicated by the electronic device relates to medical assistance, police assistance, security assistance, location assistance, assistance relating to a participant in the group of registrants associated with that electronic device, assistance relating to a participant who is separated from the group of registrants associated with that electronic device, or any combination thereof.

35. The registration and management system of claim 19 wherein the response communicates an instruction to plural electronic devices relating to their respective geographic locations.

36. The registration and management system of claim 19 wherein the response communicates an instruction to move, an instruction to not move, an instruction relating to a geographic location, a report, a notification, a warning, or a combination thereof.

37. A method for operating a registration and management system for a mass gathering event comprising:
configuring an electronic device having a device identifier and including a device for capturing data, including a communication device, including a geographic position locator for determining geographic location, the configuring including configuring the electronic device for capturing a biometric identifier relating to a group of registrants, for geo-tagging the captured data using the determined geographic location, for geo-tagging the captured biometric identifier using the determined geographic location, for date-time stamping the geo-tagged captured data and the geo-tagged captured biometric identifier, and for receiving a unique identifier;
receiving or providing a unique identifier associated with a group of registrants and the mass gathering event;
causing the date-time stamped geo-tagged captured data and date-time stamped geo-tagged captured biometric identifier to be associated with the unique identifier;
receiving registration data relating to the group of registrants;
associating the unique identifier with the received registration data relating to the group of registrants;
storing data including the unique identifier, the date-time stamped geo-tagged captured data associated with the unique identifier, the date-time stamped geo-tagged captured biometric identifier associated with the unique identifier, the received registration data relating to the group of registrants associated with the unique identifier, and the device identifier of the electronic device, in a relational data base that is separate from the electronic device;
repeating the foregoing steps for a number of groups of registrants;
retrieving from the relational database stored data relating to a particular group of registrants using the unique identifier, or using a location of geo-tagged captured data, or using the captured biometric identifier relating to the particular group of registrants, or using the received registration data relating to the particular group of registrants, or using the device identifier, or using a combination thereof;
generating from the retrieved data from the relational database relating to the particular group of registrants a response relating to the particular group of registrants wherein the response comprises a task to be performed, or an action to be taken, or a supply to be provided, or equipment to be provided, or a schedule for performing a task, or a schedule for taking an action, or a report of a task and/or an action, or a combination thereof; and
communicating the response relating to the particular group of registrants to the electronic device that captured data relating to the particular group of registrants using the device identifier of the electronic device that captured the data relating to the particular group of registrants or to an electronic device using the geographic location thereof, or to both.

38. The method for operating a registration and management system of claim 37 wherein:
receiving the unique identifier includes imaging a barcode of a data entry form using the imager of the electronic device; and
receiving registration data relating to a group of registrants includes scanning the data entry form.

39. The method for operating a registration and management system of claim 37 wherein:
the biometric identifier includes a fingerprint, a facial image, a digital signature, or a combination thereof, or
the biometric identifier is utilized for identification and/or for verification of identity; or
the biometric identifier includes a fingerprint, a facial image, a digital signature, or a combination thereof, and is utilized for identification and/or for verification of identity.

40. The method for operating a registration and management system of claim 37 wherein the generated response includes: an alert, a safety check, a warning, a request, a reminder, an instruction, a report, a report of a participant who is separated from the group of registrants, a report of a participant who is lost, a follow up notification, information relating to the group of registrants, information relating to available assistance, information relating to reviews and/or programs, orientation information, information relating to hospitality assistance, information relating to medical assistance, information relating to police or security assistance, information relating to geographical location, or any combination thereof.

41. The method for operating a registration and management system of claim 37 wherein the electronic device is employed to communicate a request to the relational data base, and wherein the generated response relates to the request and is communicated to the electronic device that communicated the request.

42. The method for operating a registration and management system of claim 41 wherein the request communicated by the electronic device relates to medical assistance, police assistance, security assistance, location assistance, assistance relating to a participant in the group of registrants associated with that electronic device, assistance relating to a participant who is separated from the group of registrants associated with that electronic device, or any combination thereof.

* * * * *